(12) United States Patent
Ella et al.

(10) Patent No.: US 9,844,588 B2
(45) Date of Patent: Dec. 19, 2017

(54) INACTIVATED CHIKUNGUNYA VIRUSES (CHIKV) COMPRISING AN E1-K211E MUTATION

(75) Inventors: Krishna Murthy Ella, Hyderabad (IN); Sumathy Kandaswamy, Hyderabad (IN)

(73) Assignee: BHARAT BIOTECH INTERNATIONAL LIMITED, Hyderabad (IN)

( * ) Notice: Subject to any disclaimer, the term of this patent is extended or adjusted under 35 U.S.C. 154(b) by 249 days.

(21) Appl. No.: 14/126,504

(22) PCT Filed: Jun. 18, 2012

(86) PCT No.: PCT/IN2012/000432
§ 371 (c)(1),
(2), (4) Date: Dec. 16, 2013

(87) PCT Pub. No.: WO2012/172574
PCT Pub. Date: Dec. 20, 2012

(65) Prior Publication Data
US 2014/0120125 A1    May 1, 2014

(30) Foreign Application Priority Data
Jun. 17, 2011 (IN) .......................... 2067/CHE/2011

(51) Int. Cl.
*A61K 39/12* (2006.01)
*A61K 39/00* (2006.01)

(52) U.S. Cl.
CPC ...... *A61K 39/12* (2013.01); *A61K 2039/5252* (2013.01); *A61K 2039/55505* (2013.01); *A61K 2039/55566* (2013.01); *A61K 2039/55583* (2013.01); *A61K 2039/70* (2013.01); *C12N 2770/24134* (2013.01); *C12N 2770/36121* (2013.01); *C12N 2770/36122* (2013.01); *C12N 2770/36123* (2013.01); *C12N 2770/36134* (2013.01); *G01N 2333/181* (2013.01); *G01N 2333/185* (2013.01); *G01N 2469/20* (2013.01); *G01N 2800/26* (2013.01)

(58) Field of Classification Search
CPC .......... A61K 39/12; C12N 2770/36123; C12N 2770/36122; C12N 2770/36121
See application file for complete search history.

(56) References Cited

FOREIGN PATENT DOCUMENTS

| WO | WO 2008/026225 A2 | 3/2008 |
|----|-------------------|--------|
| WO | WO 2008/030220 A2 | 3/2008 |
| WO | WO 2010/062396 A2 | 6/2010 |

OTHER PUBLICATIONS

Weaver, S. C., et al., 2012, Chikungunya virus and prospects for a vaccine, Exp. Rev. Vacc. 11(9):1087-1101.*
Deeba, F., et al., 2015, Chikungunya virus: recent advances in epidemiology, host pathogen interaction and vaccine strategies, Pathogens Dis. 74(3):1-10.*
Singh, P., et al., 2013, Current research and clinical trials for a vaccine against Chikungunya virus, Vacc: Devel. Ther. 3:35-46.*
Solignat, M., et al., 2009, Replication cycle of chikungunya: A re-emerging arbovirus, Virol. 393:183-197.*
International Search Report in connection with International Application No. PCT/IN2012/000432 dated Sep. 9, 2012.

* cited by examiner

*Primary Examiner* — Jeffrey Parkin
(74) *Attorney, Agent, or Firm* — Davidson, Davidson & Kappel, LLC

(57) ABSTRACT

A vaccine composition for prophylaxis and treatment of Chikungunya virus infections is disclosed which is capable of conferring immunity against any genotypic variants of the Chikungunya virus. More particularly the invention discloses particular nucleotide sequences and their translated proteins thereof, which may be expressed as Virus Like Particles which for use as a vaccine antigens against Chikungunya virus infections. The compositions disclosed in this invention are also protective against any genotypic variants of the Chikungunya virus which may be propagated by any suitable vector of the disease including *Aedis albopictus* and *Aedis aegypti*.

5 Claims, 2 Drawing Sheets

Figure-1

SEQUENCE LISTING

<160> NUMBER OF SEQ ID NOS: 22

<210> SEQ ID NO 1
<211> LENGTH: 3747
<212> TYPE: DNA
<213> ORGANISM: Chikungunya virus

<400> SEQUENCE: 1
atggagttca tcccaaccca aactttttac aataggaggt accagcctcg accctggact 60
ccgcgctcta ctatccaaat cattaggccc agaccgcgcc ctcagaggca agctgggcaa 120
cttgcccagc tgatctcagc agttaataaa ctgacaatgc gcgcggtacc ccaacagaag 180
ccacgcagga atcggaagaa taagaagcaa aagcaaaaac aacaggcgcc acaaaacaac 240
acaaatcaaa agaagcagcc acctaaaaag aaaccggctc aaaagaaaaa gaagccgggc 300
cgcagagaga ggatgtgcat gaaaatcgaa aatgattgta ttttcgaagt caagcacgaa 360
ggtaaggtaa caggttacgc gtgcctggtg ggggacaaag taatgaaacc agcacacgta 420
aaggggacca tcgataacgc ggacctggcc aaactggcct ttaagcggtc atctaagtat 480
gaccttgaat gcgcgcagat acccgtgcac atgaagtccg acgcttcgaa gttcacccat 540
gagaaaccgg aggggtacta caactggcac cacggagcag tacagtactc aggaggccgg 600
ttcaccatcc ctacaggtgc tggcaaacca ggggacagcg gcagaccgat cttcgacaac 660
aagggacgcg tggtggccat agtcttagga ggagctaatg aaggagcccg tacagccctc 720
tcggtggtga cctggaataa agacattgtc actaaaatca cccccgaggg ggccgaagag 780
tggagtcttg ccatcccagt tatgtgcctg ctggcaaaca ccacgttccc ctgctcccag 840 ccccccttgca cgccctgctg ctacgaaaag gaaccggagg aaaccctacg catgcttgag 900
gacaacgtca tgagacctgg gtactatcag ctgctacagg catccttaac atgttctccc 960
caccgccagc gacgcagcac caaggacaac ttcaatgtct ataaagccac aagaccatac 1020
ttagctcact gtcccgactg tggagaaggg cattcgtgcc atagtcccgt agcactagaa 1080
cgcatcagaa atgaagcgac agacgggacg ctgaaaatcc aggtctcctt gcaaatcaga 1140
ataaagacgg atgacagcca cgattggacc aagctgcgtt atatggacaa ccacatgcca 1200
gcagacgcag agagggcggg gctatttgta agaacatcag caccgtgtac gattactgga 1260
acaatgggac acttcatcct ggcccgatgt ccaaaagggg aaactctgac ggtgggattc 1320
actgacagta ggaagattag tcattcatgt acgcacccat ttcaccacga ccctcctgtg 1380
ataggtcggg aaaaattcca ttcccgaccg cagcacggta aagagctacc ttgcagcacg 1440
tacgtgcaga gcaccgccgc aactaccgag gagatagagg tacacatgcc cccagacacc 1500
cctgatcgca cattaatgtc acaacagtcc ggcaacgtaa agatcacagt caatggccag 1560
acggtgcggt acaagtgtaa ttgcggtggc tcaaatgaag gactaacaac tacagacaaa 1620
gtgattaata actgcaaggt tgatcaatgt catgccgcgg tcaccaatca caaaaagtgg 1680
cagtataact cccctctggt cccgcgtaat gctgaacttg gggaccgaaa aggaaaaatt 1740
cacatcccgt ttccgctggc aaatgcaaca tgcagggtgc ctaaagcaag gaaccccacc 1800
gtgacgtacg ggaaaaacca agtcatcatg ctactgtatc ctgaccaccc aacactcctg 1860
tcctaccgga atatgggaga agaaccaaac tatcaagaag agtgggtgat gcataagaag 1920
gaagtcgtgc taaccgtgcc gactgaaggg ctcgaggtca cgtggggcaa caacgagccg 1980
tataagtatt ggccgcagtt atctacaaac ggtacagccc atggccaccc gcatgagata 2040
attctgtatt attatgagct gtaccctact atgactgtag tagttgtgtc agtggccacg 2100

| | |
|---|---|
| ttcatactcc tgtcgatggt gggtatggca gcggggatgt gcatgtgtgc acgacgcaga | 2160 |
| tgcatcacac cgtatgaact gacaccagga gctaccgtcc ctttcctgct tagcctaata | 2220 |
| tgctgcatca gaacagctaa agcggccaca taccaagagg ctgcgatata cctgtggaac | 2280 |
| gagcagcaac ctttgttttg gctacaagcc cttattccgc tggcagccct gattgttcta | 2340 |
| tgcaactgtc tgagactctt accatgctgc tgtaaaacgt tggcttttt agccgtaatg | 2400 |
| agcgtcggtg cccacactgt gagcgcgtac gaacacgtaa cagtgatccc gaacacggtg | 2460 |
| ggagtaccgt ataagactct agtcaataga cctggctaca gccccatggt attggagatg | 2520 |
| gaactactgt cagtcacttt ggagccaaca ctatcgcttg attacatcac gtgcgagtac | 2580 |
| aaaaccgtca tcccgtctcc gtacgtgaag tgctgcggta cagcagagtg caaggacaaa | 2640 |
| aacctacctg actacagctg taaggtcttc accggcgtct acccatttat gtggggcggc | 2700 |
| gcctactgct tctgcgacgc tgaaaacacg cagttgagcg aagcacatgt ggagaagtcc | 2760 |
| gaatcatgca aaacagaatt tgcatcagca tacagggctc ataccgcatc tgcatcagct | 2820 |
| aagctccgcg tcctttacca aggaaataac atcactgtaa ctgcctatgc aaacggcgac | 2880 |
| catgccgtca cagttaagga cgccaaattc attgtggggc caatgtcttc agcctggaca | 2940 |
| cctttcgaca caaaattgt ggtgtacaaa ggtgacgtct ataacatgga ctaccccgccc | 3000 |
| tttggcgcag gaagaccagg acaatttggc gatatccaaa gtcgcacacc tgagagtgaa | 3060 |
| gacgtctatg ctaatacaca actggtactg cagagaccgg ctgcgggtac ggtacacgtg | 3120 |
| ccatactctc aggcaccatc tggctttaag tattggctaa agaacgcgg ggcgtcactg | 3180 |
| cagcacacag caccatttgg ctgccaaata gcaacaaacc cggtaagagc ggtgaactgc | 3240 |
| gccgtaggga acatgcccat ctccatcgac ataccggaag cggccttcac tagggtcgtc | 3300 |
| gacgcgccct ctttaacgga catgtcgtgc gaggtaccag cctgcaccca ttcctcagac | 3360 |
| tttgggggcg tcgccattat taaatatgca gccagcaaga aggcaagtg tgcggtgcat | 3420 |
| tcgatgacta acgccgtcac tattcgggaa gctgagatag aagttgaagg gaattctcag | 3480 |
| ctgcaaatct ctttctcgac ggccttagcc agcgccgaat ccgcgtaca agtctgttct | 3540 |
| acacaagtac actgtgcagc tgagtgccac cccccgaagg accacatagt caactacccg | 3600 |
| gcgtcacata ccaccctcgg ggtccaggac atctccgcta cggcgatgtc atgggtgcag | 3660 |
| aagatcacgg gaggtgtggg actggttgtt gctgttgccg cactgattct aatcgtggtg | 3720 |
| ctatgcgtgt cgttcagcag gcactaa | 3747 |

<210> SEQ ID NO 2
<211> LENGTH: 3747
<212> TYPE: DNA
<213> ORGANISM: Chikungunya virus

<400> SEQUENCE: 2

| | |
|---|---|
| atggagttca tcccaaccca aacttttac aataggaggt accagcctcg accctggact | 60 |
| ccgcgctcta ctatccaaat cattaggccc agaccgcgcc ctcagaggca agctgggcaa | 120 |
| cttgcccagc tgatctcagc agttaataaa ctgacaatgc gcgcggtacc ccaacagaag | 180 |
| ccacgcagga atcggaagaa taagaagcaa agcaaaaac aacaggcgcc acaaacaac | 240 |
| acaaatcaaa agaagcagcc acctaaaaag aaaccggctc aaaagaaaaa gaagccgggc | 300 |
| cgcagagaga ggatgtgcat gaaaatcgaa aatgattgta ttttcgaagt caagcacgaa | 360 |
| ggtaaggtaa caggttacgc gtgcctggtg ggggacaaag taatgaaacc agcacacgta | 420 |

```
aaggggacca tcgataacgc ggacctggcc aaactggcct ttaagcggtc atctaagtat    480
gaccttgaat gcgcgcagat acccgtgcac atgaagtccg acgcttcgaa gttcacccat    540
gagaaaccgg aggggtacta caactggcac cacggagcag tacagtactc aggaggccgg    600
ttcaccatcc ctacaggtgc tggcaaacca ggggacagcg gcagaccgat cttcgacaac    660
aagggacgcg tggtggccat agtcttagga ggagctaatg aaggagcccg tacagccctc    720
tcggtggtga cctggaataa agacattgtc actaaaatca cccccgaggg ggccgaagag    780
tggagtcttg ccatcccagt tatgtgcctg ctggcaaaca ccacgttccc ctgctcccag    840
cccccttgca cgccctgctg ctacgaaaag gaaccggagg aaaccctacg catgcttgag    900
aacaacgtca tgagaccagg gtactatcag ctgctacagg catccttaac atgttctccc    960
caccgccagc gacgcagcac caaggacaac ttcaatgtct ataaagccac aagaccatac   1020
ttagctcact gtcccgactg tggagaaggg cactcgtgcc atagtcccgt agcactagaa   1080
cgcatcagaa atgaagcgac agacgggacg ctgaaaatcc aggtctcctt gcaaatcgga   1140
ataaagacgg atgacagcca cgattggacc aagctgcgtt atatggacaa ccacatgcca   1200
gcagacgcag agagggcggg gctatttgta agaacatcag caccgtgtac gattactgga   1260
acaatgggac acttcatcct ggcccgatgt ccaaaagggg aaactctgac ggtgggattc   1320
actgacagta ggaagattag tcattcatgt acgcacccat ttcaccacga ccctcctgtg   1380
ataggtcggg aaaaattcca ttcccgaccg cagcacggta aagagctacc ttgcagcacg   1440
tacgtgcaga gcaccgccgc aactaccgag gagatagagg tacacatgcc cccagacacc   1500
cctgatcgca cattaatgtc acaacagtcc ggcaacgtaa agatcacagt caatggccag   1560
acggtgcggt acaagtgtaa ttgcggtggc tcaaatgaag gactaacaac tacagacaaa   1620
gtgattaata actgcaaggt tgatcaatgt catgccgcgg tcaccaatca caaaagtgg    1680
cagtataact cccctctggt cccgcgtaat gctgaacttg gggaccgaaa aggaaaaatt   1740
cacatcccgt ttccgctggc aaatgcaaca tgcagggtgc ctaaagcaag gaaccccacc   1800
gtgacgtacg ggaaaaacca agtcatcatg ctactgtatc ctgaccaccc aacactcctg   1860
tcctaccgga atatgggaga agaaccaaac tatcaagaag agtgggtgat gcataagaag   1920
gaagtcgtgc taaccgtgcc gactgaaggg ctcgaggtca cgtggggcaa caacgagccg   1980
tataagtatt ggccgcagtt atctacaaac ggtacagccc atggccaccc gcatgagata   2040
attctgtatt attatgagct gtaccctact atgactgtag tagttgtgtc agtggccacg   2100
ttcatactcc tgtcgatggt gggtatggca gcggggatgt gcatgtgtgc acgacgcaga   2160
tgcatcacac cgtatgaact gacaccagga gctaccgtcc ctttcctgct agcctaata    2220
tgctgcatca gaacagctaa agcggccaca taccaagagg ctgcgatata cctgtggaac   2280
gagcagcaac ctttgttttg gctacaagcc cttattccgc tggcagccct gattgttcta   2340
tgcaactgtc tgagactctt accatgctgc tgtaaaacgc tggctttttt agccgtaatg   2400
agcgtcggtg cccacactgt gagcgcgtac gaacacgtaa cagtgatccc gaacacggtg   2460
ggagtaccgt ataagactct agtcaataga cctggctaca gccccatggt attggagatg   2520
gaactactgt cagtcacttt ggagccaaca ctatcgcttg attacatcac gtgcgagtac   2580
aaaaccgtca tcccgtctcc gtacgtgaag tgctgcggta cagcagagtg caaggacaaa   2640
aacctacctg actacagctg taaggtcttc accggcgtct acccatttat gtggggcggc   2700
gcctactgct tctgcgacgc tgaaaacacg cagttgagcg aagcacatgt ggagaagtcc   2760
gaatcatgca aaacagaatt tgcatcagca tacagggctc ataccgcatc tgcatcagct   2820
```

```
aagctccgcg tcctttacca aggaaataac atcactgtaa ctgcctatgc aaacggcgac    2880
catgccgtca cagttaagga cgccaaattc attgtggggc caatgtcttc agcctggaca    2940
cctttcgaca acaaaattgt ggtgtacaaa ggtgacgtct ataacatgga ctacccgccc    3000
tttggcgcac aagaccagg  acaatttggc gatatccaaa gtcgcacacc tgagagtgaa    3060
gacgtctatg ctaatacaca actggtactg cagagaccgg ctgcgggtac ggtacacgtg    3120
ccatactctc aggcaccatc tggctttaag tattggctaa agaacgcgg  ggcgtcactg    3180 cagcacacag caccatttgg ctgccaaata gcaacaaacc cggtaagagc ggtgaactgc    3240
gccgtaggga acatgcccat ctccatcgac ataccggaag cggccttcac tagggtcgtc    3300
gacgcgccct ctttaacgga catgtcgtgc gaggtaccag cctgcaccca ttcctcagac    3360
tttgggggcg tcgccattat taaatatgca gccagcaaga aggcaagtg  tgcggtgcat    3420 tcgatgacta acgccgtcac tattcgggaa gctgagatag aagttgaagg gaattctcag    3480
ctgcaaatct ctttctcgac ggccttagcc agcgccgaat tccgcgtaca agtctgttct    3540
acacaagtac actgtgcagc tgagtgccac cccccgaagg accacatagt caactacccg    3600
gcgtcacata ccaccctcgg ggtccaggac atctccgcta cggcgatgtc atgggtgcag    3660
aagatcacgg gaggtgtggg actggttgtt gctgttgccg cactgattct aatcgtggtg    3720
ctatgcgtgt cgttcagcag gcactaa                                        3747

<210> SEQ ID NO 3
<211> LENGTH: 3747
<212> TYPE: DNA
<213> ORGANISM: Chikungunya virus

<400> SEQUENCE: 3
atggagttca tcccaaccca aacttttttac aataggaggt accagcctcg accctggact      60
ccgcgctcta ctatccaaat cattaggccc agaccgcgcc ctcagaggca agctgggcaa     120
cttgcccagc tgatctcagc agttaataaa ctgacaatgc gcgcggtacc caacagaag      180 ccacgcagga atcggaagaa taagaagcaa agcaaaaac  aacaggcgcc acaaaacaac     240
acaaatcaaa agaagcagcc acctaaaaag aaaccggctc aaaagaaaaa gaagccgggc     300
cgcagagaga ggatgtgcat gaaaatcgaa atgattgta  ttttcgaagt caagcacgaa     360
ggtaaggtaa caggttacgc gtgcctggtg ggggacaaag taatgaaacc agcacacgta     420
aaggggacca tcgataacgc ggacctggcc aaactggcct ttaagcggtc atctaagtat     480
gaccttgaat gcgcgcagat acccgtgcac atgaagtccg acgcttcgaa gttcacccat     540
gagaaaccgg agggtactac caactggcac cacggagcag tacagtactc aggaggccgg     600
ttcaccatcc ctacaggtgc tggcaaacca ggggacagcg gcagaccgat cttcgacaac     660
aagggacgcg tggtggccat agtcttagga ggagctaatg aaggagcccg tacagccctc     720
tcggtggtga cctggaataa agacattgtc actaaaatca cccccgaggg ggccgaagag     780
tggagtcttg ccatcccagt tatgtgcctg ctggcaaaca ccacgttccc ctgctcccag     840
ccccccttgc acgccctgct ctacgaaaag gaaccggagg aaacccctacg catgcttgag     900 gacaacgtca tgagacctgg gtactatcag ctgctacagg catccttaac atgttctccc     960
caccgccagc gacgcagcac caaggacaac ttcaatgtct ataaagccac aagaccatac    1020
ttagctcact gtcccgactg tggagaaggg cactcgtgcc atagtcccgt agcactagaa    1080
cgcatcagaa atgaagcgac agacgggacg ctgaatatcc aggtctcctt gcaaatcgga    1140
```

```
ataaagacgg atgacagcca cgattggacc aagctgcgtt atatggacaa ccacatgcca   1200
gcagacgcag agagggcggg gctatttgta agaacatcag caccgtgtac gattactgga   1260
acaatgggac acttcatcct ggcccgatgt ccaaaagggg aaactctgac ggtgggattc   1320
actgacagta ggaagattag tcattcatgt acgcacccat ttcaccacga ccctcctgtg   1380
ataggtcggg aaaaattcca ttcccgaccg cagcacggta aagagctacc ttgcagcacg   1440
tacgtgcaga gcaccgccgc aactaccgag gagatagagg tacacatgcc cccagacacc   1500
cctgatcgca cattaatgtc acaacagtcc ggcaacgtaa agatcacagt caatggccag   1560
acggtgcggt acaagtgtaa ttgcggtggc tcaaatgaag gactaacaac tacagacaaa   1620
gtgattaata actgcaaggt tgatcaatgt catgccgcgg tcaccaatca caaaaagtgg   1680
cagtataact cccctctggt cccgcgtaat gctgaacttg gggaccgaaa aggaaaaatt   1740
cacatcccgt ttccgctggc aaatgcaaca tgcagggtgc ctaaagcaag gaaccccacc   1800
gtgacgtacg ggaaaaacca agttatcatg ctactgtatc ctgaccaccc aacactcctg   1860
tcctaccgga atatgggaga agaaccaaac tatcaagaag agtgggtgat gcataagaag   1920
gaagtcgtgc taaccgtgcc gactgaaggg ctcgaggtca cgtggggcaa caacgagccg   1980
tataagtatt ggccgcagtt atctacaaac ggtacagccc atggccaccc gcatgagata   2040
attctgtatt attatgagct gtaccctact atgactgtag tagttgtgtc agtggccacg   2100
ttcatactcc tgtcgatggt gggtatggca gcggggatgt gcatgtgtgc acgacgcaga   2160
tgcatcacac cgtatgaact gacaccagga gctaccgtcc ctttcctgct tagcctaata   2220
tgctgcatca gaacagctaa agcggccaca taccaagagg ctgcgatata cctgtggaac   2280
gagcagcaac ctttgttttg gctacaagcc cttattccgc tggcagccct gattgtccta   2340
tgcaactgtc tgagactctt accatgctgc tgtaaaacgt tggcttttt agccgtaatg   2400 agcgtcggtg cccacactgt gagcgcgtac gaacacgtaa cagtgatccc gaacacggtg   2460
ggagtaccgt ataagactct agtcaataga cctggctaca gccccatggt attggagatg   2520
gaactactgt cagtcacttt ggagccaaca ctatcgcttg attacatcac gtgcgagtac   2580
aaaaccgtca tcccgtctcc gtacgtgaag tgctgcggta cagcagagtg caaggacaaa   2640
aacctacctg actacagctg taaggtcttc accggcgtct acccatttat gtggggcggc   2700
gcctactgct tctgcgacgc tgaaaacacg cagttgagcg aagcacatgt ggagaagtcc   2760
gaatcatgca aaacagaatt tgcatcagca tacagggctc ataccgcatc tgcatcagct   2820
aagctccgcg tcctttacca aggaaataac atcactgtaa ctgcctatgc aaacggcgac   2880
catgccgtca cagttaagga cgccaaattc attgtggggc caatgtcttc agcctggaca   2940
cctttcgaca caaaaattgt ggtgtacaaa ggtgacgtct ataacatgga ctacccgccc   3000
tttggcgcag gaagaccagg acaatttggc gatatccaaa gtcgcacacc tgagagtgaa   3060
gacgtctatg ctaatacaca actggtactg cagagaccgg ctgcgggtac ggtacacgtg   3120
ccatactctc aggcaccatc tggctttaag tattggctaa agaacgcgg ggcgtcactg   3180 cagcacacag caccatttgg ctgccaaata gcaacaaacc cggtaagagc ggtgaactgc   3240
gccgtaggga acatgcccat ctccatcgac ataccggaag cggccttcac tagggtcgtc   3300
gacgcgccct ctttaacgga catgtcgtgc gaggtaccag cctgcaccca ttcctcagac   3360
tttgggggcg tcgccattat taaatatgca gccagcaaga aggcaagtg tgcggtgcat   3420 tcgatgacta acgccgtcac tattcgggaa gctgagatag aagttgaagg gaattctcag   3480
ctgcaaatct cttctctcga ggccttagcc agcgccgaat tccgcgtaca agtctgttct   3540
```

| | | |
|---|---|---|
| acacaagtac actgtgcagc tgagtgccac ccccgaagg accacatagt caactacccg | 3600 | |
| gcgtcacata ccaccctcgg ggtccaggac atctccgcta cggcgatgtc atgggtgcag | 3660 | |
| aagatcacgg gaggtgtggg actggttgtt gctgttgccg cactgattct aatcgtggtg | 3720 | |
| ctatgcgtgt cgttcagcag gcactaa | 3747 | |

```
<210> SEQ ID NO 4
<211> LENGTH: 3747
<212> TYPE: DNA
<213> ORGANISM: Chikungunya virus

<400> SEQUENCE: 4
```

| | |
|---|---|
| atggagttca tcccaaccca aacttttac aataggaggt accagcctcg accctggact | 60 |
| ccgcgctcta ctatccaaat cattaggccc agaccgcgcc ctcagaggca agctgggcaa | 120 |
| cttgcccagc tgatctcagc agttaataaa ctgacaatgc gcgcggtacc ccaacagaag | 180 |
| ccacgcagga atcggaagaa taagaagcaa agcaaaaac aacaggcgcc acaaaacaac | 240 |
| acaaatcaaa agaagcagcc acctaaaaag aaaccggctc aaaagaaaaa gaagccgggc | 300 |
| cgcagagaga ggatgtgcat gaaaatcgaa atgattgta ttttcgaagt caagcacgaa | 360 |
| ggtaaggtaa caggttacgc gtgcctggtg ggggacaaag taatgaaacc agcacacgta | 420 |
| aaggggacca tcgataacgc ggaccctggcc aaactggcct ttaagcggtc atctaagtat | 480 |
| gaccttgaat gcgcgcagat acccgtgcac atgaagtccg acgcttcgaa gttcacccat | 540 |
| gagaaaccgg aggggtacta caactggcac acggagcag tacagtactc aggaggccgg | 600 |
| ttcaccatcc ctacaggtgc tggcaaacca ggggacagcg gcagaccgat cttcgacaac | 660 |
| aagggacgcg tggtggccat agtcttagga ggagttaatg aaggagcccg tacagccctc | 720 |
| tcggtggtga cctggaataa agacattgtc actaaaatca cccccgaggg ggccgaagag | 780 |
| tggagtcttg ccatcccagt tatgtgcctg ctggcaaaca ccacgttccc ctgctcccag | 840 |
| ccccctgca cgccctgctg ctacgaaaag gaaccggagg aaacccctacg catgcttgag | 900 |
| gacaacgtca tgagacctgg gtactatcag ctgctacagg catccttaac atgttctccc | 960 |
| caccgccagc gacgcagcac caaggacaac ttcaatgtct ataaagccac aagaccatac | 1020 |
| ttagctcact gtcccgactg tggagaaggg cactcgtgcc atagtccgt agcactagaa | 1080 |
| cgcatcagaa atgaagcgac agacgggacg ctgaaaatcc aggtctcctt gcaaatcgga | 1140 |
| ataaagacgg atgacagcca cgattggacc aagctgcgtt atatggacaa ccacatgcca | 1200 |
| gcagacgcag agagggcggg gctatttgta agaacatcag caccgtgtac gattactgga | 1260 |
| acaatgggac acttcatcct ggcccgatgt ccaaaggggg aaactctgac ggtgggattc | 1320 |
| actgacagta ggaagattag tcattcatgt acgcacccat tcaccacga ccctcctgtg | 1380 |
| ataggtcggg aaaaattcca ttcccgaccg cagcacggta agagctacc ttgcagcacg | 1440 |
| tacgtgcaga gcaccgccgc aactaccgag gagatagagg tacacatgcc cccagacacc | 1500 |
| cctgatcgca cattaatgtc acaacagtcc ggcaacgtaa agatcacagt caatggccag | 1560 |
| acggtgcggt acaagtgtaa ttgcggtggc tcaaatgaag gactaacaac tacagacaaa | 1620 |
| gtgattaata actgcaaggt tgatcaatgt catgccgcgg tcaccaatca caaaaagtgg | 1680 |
| cagtataact cccctctggt cccgcgtaat gctgaacttg ggaccgaaa aggaaaaatt | 1740 |
| cacatcccgt ttccgctggc aaatgcaaca tgcagggtgc ctaaagcaag gaaccccacc | 1800 |
| gtgacgtacg ggaaaaacca agtcatcatg ctactgtatc ctgaccaccc aacactcctg | 1860 |

```
tcctaccgga atatgggaga agaaccaaac tatcaagaag agtgggtgat gcataagaag    1920
gaagtcgtgc taaccgtgcc gactgaaggg ctcgaggtca cgtggggcaa caacgagccg    1980
tataagtatt ggccgcagtt atctacaaac ggtacagccc atggccaccc gcatgagata    2040
attctgtatt attatgagct gtaccctact atgactgtag tagttgtgtc agtggccacg    2100
ttcatactcc tgtcgatggt gggtatggca gcggggatgt gcatgtgtgc acgacgcaga    2160
tgcatcacac cgtatgaact gacaccagga gctaccgtcc ctttcctgct tagcctaata    2220
tgctgcatca gaacagctaa agcggccaca taccaagagg ctgcgatata cctgtggaac    2280
gagcagcaac ctttgttttg ctacaagcc cttattccgc tggcagccct gattgttcta     2340
tgcaactgtc tgagactctt accatgctgc tgtaaaacgc tggcttttt agccgtaatg     2400 agcgtcggtg cccacactgt gagcgcgtac gaacacgtaa cagtgatccc gaacacggtg    2460
ggagtaccgt ataagactct agtcaataga cctggctaca gccccatggt attggagatg    2520
gaactactgt cagtcacttt ggagccaaca ctatcgcttg attacatcac gtgcgagtac    2580
aaaaccgtca tcccgtctcc gtacgtgaag tgctgcggta cagcagagtg caaggacaaa    2640
aacctacctg actacagctg taaggtcttc accggcgtct acccatttat gtggggcggc    2700
gcctactgct tctgcgacgc tgaaaacacg cagttgagcg aagcacatgt ggagaagtcc    2760
gaatcatgca aaacagaatt tgcatcagca tacagggcgc ataccgcatc tgcatcagct    2820
aagctccgcg tcctttacca aggaaataac atcactgtaa ctgcctatgc aaacggcgac    2880
catgccgtca cagttaagga cgccaaattc attgtggggc caatgtcttc agcctggaca    2940
cctttcgaca caaaattgt ggtgtacaaa ggtgacgtct ataacatgga ctacccgccc      3000
tttggcgcac gaagaccagg acaatttggc gatatccaaa gtcgcacacc tgagagtgaa    3060
gacgtctatg ctaatacaca actggtactg cagagaccgg ctgcgggtac ggtacacgtg    3120
ccatactctc aggcaccatc tggctttaag tattggctaa agaacgcgg ggcgtcactg     3180 cagcacacag caccatttgg ctgccaaata gcaacaaacc cggtaagagc ggtgaactgc    3240
gccgtaggga acatgcccat ctccatcgac ataccggaag cggccttcac tagggtcgtc    3300
gacgcgccct ctttaacgga catgtcgtgc gaggtaccag cctgcaccca ttcctcagac    3360
tttgggggcg tcgccattat taaatatgca gccagcaaga aaggcaagtg tgcggtgcat    3420
tcgatgacta acgccgtcac tattcgggaa gctgagatag aagttgaagg gaattctcag    3480
ctgcaaatct ctttctcgac ggccttagcc agcgccgaat ccgcgtaca agtctgttct     3540 acacaagtac actgtgcagc tgagtgccac ccccgaagg accacatagt caactacccg     3600
gcgtcacata ccaccctcgg ggtccaggac atctccgcta cggcgatgtc atgggtgcag    3660
aagatcacgg gaggtgtggg actggttgtt gctgttgccg cactgattct aatcgtggtg    3720
ctatgcgtgt cgttcagcag gcactaa                                       3747

<210> SEQ ID NO 5
<211> LENGTH: 3747
<212> TYPE: DNA
<213> ORGANISM: Chikungunya virus

<400> SEQUENCE: 5
atggagttca tcccaaccca acttttttac aataggaggt accagcctcg accctggact    60
ccgcgctcta ctatccaaat cattaggccc agaccgcgcc ctcagaggca agctgggcaa    120
cttgcccagc tgatctcagc agttaataaa ctgacaatgc gcgcggtacc ccaacagaag    180
ccacgcagga atcggaagaa taagaagcaa agcaaaaac aacaggcgcc acaaaacaac     240
```

```
acaaatcaaa agaagcagcc acctaaaaag aaaccggctc aaaagaaaaa gaagccgggc        300
cgcagagaga ggatgtgcat gaaaatcgaa aatgattgta ttttcgaagt caagcacgaa        360
ggtaaggtaa caggttacgc gtgcctggtg ggggacaaag taatgaaacc agcacacgta        420
aaggggacca tcgataacgc ggacctggcc aaactggcct ttaagcggtc atctaagtat        480
gaccttgaat gcgcgcagat acccgtgcac atgaagtccg acgcttcgaa gttcacccat        540
gagaaaccgg aggggtacta caactggcac cacggggcag tacagtactc aggaggccgg        600
ttcaccatcc ctacaggtgc tggcaaacca ggggacagcg gcagaccgat cttcgacaac        660
aagggacgcg tggtggccat agtcttagga ggagctaatg aaggagcccg tacagccctc        720
tcggtggtga cctggaataa agacattgtc actaaaatca cccccgaggg ggccgaagag        780
tggagtcttg ccatcccagt tatgtgcctg ctggcaaaca ccacgttccc ctgctcccag        840
cccccttgca cgccctgctg ctacgaaaag gaaccggagg aaaccctacg catgcttgag        900
gacaacgtca tgagacctgg gtactatcag ctgctacagg catccttaac atgttctccc        960
caccgccagc gacgcagcac caaggacaac ttcaatgtct ataaagccac aagaccatac       1020
ttagctcact gtcccgactg tggagaaggg cactcgtgcc atagtcccgt agcactagaa       1080
cgcatcagaa atgaagcgac agacgggacg ctgaaaatcc aggtctcctt gcaaatcgga       1140
ataaagacgg atgacagcca cgattggacc gagctgcgtt atatggacaa ccacatgcca       1200
gcagacgcag agagggcggg gctatttgta agaacatcag caccgtgtac gattactgga       1260
acaatgggac acttcatcct ggcccgatgt ccaaaagggg aaactctgac ggtgggattc       1320
actgacagta ggaagattag tcattcatgt acgcacccat ttcaccacga ccctcctgtg       1380
ataggtcggg aaaaattcca ttcccgaccg cagcacggta aagagctacc ttgcagcacg       1440
tacgtgcaga gcaccgccgc aactaccgag gagatagagg tacacatgcc cccagacacc       1500
cctgatcgca cattaatgtc acaacagtcc ggcaacgtaa agatcacagt caatggccag       1560
acggtgcggt acaagtgtaa ttgcggtggc tcaaatgaag gactaacaac tacagacaaa       1620
gtgattaata actgcaaggt tgatcaatgt catgccgcgg tcaccaatca caaaagtgg        1680 cagtataact cccctctggt cccgcgtaat gctgaacttg ggaccgaaa aggaaaaatt        1740 cacatcccgt ttccgctggc aaatgcaaca tgcagggtgc ctaaagcaag gaaccccacc       1800
gtgacgtacg ggaaaaacca agtcatcatg ctactgtatc ctgaccaccc aacactcctg       1860
tcctaccgga atatgggaga agaaccaaac tatcaagaag agtgggtgat gcataagaag       1920
gaagtcgtgc taaccgtgcc gactgaaggg ctcgaggtca cgtggggcaa caacgagccg       1980
tataagtatt ggccgcagtt atctacaaac ggtacagccc atggccaccc gcatgagata       2040
attctgtatt attatgagct gtaccctact atgactgtag tagttgtgtc agtggccacg       2100
ttcatactcc tgtcgatggt gggtatggca gcggggatgt gcatgtgtgc acgacgcaga       2160
tgcatcacac cgtatgaact gacaccagga gctaccgtcc ctttcctgct agcctaata        2220 tgctgcatca gaacagctaa agcggccaca taccaagagg ctgcgatata cctgtggaac       2280
gagcagcaac ctttgttttg gctacaagcc cttattccgc tggcagccct gattgttcta       2340
tgcaactgtc tgagactctt accatgctgc tgtaaaacgc tggcttttt agccgtaatg       2400 agcgtcggtg cccacactgt gagcgcgtac gaacacgtaa cagtgatccc gaacacggtg       2460
ggagtaccgt ataagactct agtcaataga cctggctaca gccccatggt attggagatg       2520
gaactactgt cagtcacttt ggagccaaca ctatcgcttg attacatcac gtgcgagtac       2580
```

```
aaaaccgtca tcccgtctcc gtacgtgaag tgctgcggta cagcagagtg caaggacaaa    2640
aacctacctg actacagctg taaggtcttc accggcgtct acccatttat gtggggcggc    2700
gcctactgct tctgcgacgc tgaaaacacg cagttgagcg aagcacatgt ggagaagtcc    2760
gaatcatgca aaacagaatt tgcatcagca tacagggcgc ataccgcatc tgcatcagct    2820
aagctccgcg tcctttacca aggaaataac atcactgtaa ctgcctatgc aaacggcgac    2880
catgccgtca cagttaagga cgccaaattc attgtggggc caatgtcttc agcctggaca    2940
cctttcgaca acaaaattgt ggtgtacaaa ggtgacgtct ataacatgga ctacccgccc    3000
tttggcgcag gaagaccagg acaatttggc gatatccaaa gtcgcacacc tgagagtgaa    3060
gacgtctatg ctaatacaca actggtactg cagagaccgg ctgcgggtac ggtacacgtg    3120
ccatactctc aggcaccatc tggctttaag tattggctaa agaacgcgg ggcgtcactg    3180 cagcacacag caccatttgg ctgccaaata gcaacaaacc cggtaagagc ggtgaactgc    3240
gccgtaggga acatgcccat ctccatcgac ataccggaag cggccttcac tagggtcgtc    3300
gacgcgccct ctttaacgga catgtcgtgc gaggtaccag cctgcaccca ttcctcagac    3360
tttgggggcg tcgccattat taaatatgca gccagcaaga aaggcaagtg tgcggtgcat    3420
tcgatgacta acgccgtcac tattcgggaa gctgagatag aagttgaagg gaattctcag    3480
ctgcaaatct ctttctcgac ggccttagcc agcgccgaat ccgcgtaca agtctgttct    3540 acacaagtac actgtgcagc tgagtgccac cccccgaagg accacatagt caactacccg    3600
gcgtcacata ccacccctcgg ggtccaggac atctccgcta cggcgatgtc atgggtgcag    3660
aagatcacgg gaggtgtggg actggttgtt gctgttgccg cactgattct aatcgtggtg    3720
ctatgcgtgt cgttcagcag gcactaa                                        3747

<210> SEQ ID NO 6
<211> LENGTH: 3747
<212> TYPE: DNA
<213> ORGANISM: Chikungunya virus

<400> SEQUENCE: 6
atggagttca tcccaaccca aacttttac aataggaggt accagcctcg accctggact      60
ccgcgctcta ctatccaaat catcaggccc agaccgcgcc ctcagaggca agctgggcaa     120
cttgcccagc tgatctcagc agttaataaa ctgacaatgc gcgcggtacc ccaacagaag     180
ccacgcagga atcggaagaa taagaagcaa aagcaaaaac aacaggcgcc acaaacaac     240 acaaatcaaa agaagcagcc acctaaaaag aaaccggctc aaaagaaaaa gaagccgggc     300
cgcagagaga ggatgtgcat gaaaatcgaa atgattgta ttttcgaagt caagcacgaa      360
ggtaaggtaa caggttacgc gtgcctggtg ggggacaaag taatgaaacc agcacacgta     420
aaggggacca tcgataacgc ggacctggcc aaactggcct ttaagcggtc atctaagtat     480
gaccttgaat gcgcgcagat accgtgcac atgaagtccg acgcttcgaa gttcacccat     540
gagaaaccgg agggtacta caactggcac cacgagcag tacaatactc aggaggccgg      600
ttcaccatcc ctacaggtgc tggcaaacca ggggacagcg gcagacctat cttcgacaac     660
aagggacgcg tggtggccat agtcttagga ggagctaatg aaggagcccg tacagccctc     720
tcggtggtga cctggaataa agacattgtc actaaaatca cccccgaggg ggccgaagag     780
tggagtcttg ccatcccagt tatgtgcctg ttggcaaaca ccacgttccc ctgctcccag     840 ccccccttgca cgccctgctg ctacgaaaag gaaccggag aaaaccctacg catgcttgag      900 gacaacgtca tgagacctgg gtactatcag ctgctacaag catccttaac atgttctccc     960
```

```
caccgccagc gacgcagcac caaggacaac ttcaatgtct ataaagccac aagaccatac    1020
ttagctcact gtcccgactg tggagaaggg cactcgtgcc atagtcccgt agcactagaa    1080
cgcatcagaa atgaagcgac agacgggacg ctgaaaatcc aggtctcctt gcaaatcaga    1140
ataaagacgg atgacagcca cgattggacc aagctgcgtt atatggacaa ccacatgcca    1200
gcagacgcag agagggcggg gctatttgta agaacatcag caccgtgtac gattactgga    1260
acaatgggac acttcatcct ggcccgatgt ccaaaagggg aaactctgac ggtgggattc    1320
actgacagta ggaagattag tcattcatgt acgcacccat ttcaccacga ccctcctgtg    1380
ataggtcggg aaaaattcca ttcccgaccg cagcacggta aagagctacc ttgcagcacg    1440
tacgtgcaga gcaccgccgc aactaccgag gagatagagg tacacatgcc cccagacacc    1500
cctgatcgca cattaatgtc acaacagtcc ggcaacgtaa agatcacagt caatggccag    1560
acggtgcggt acaagtgtaa ttgcggtggc tcaaatgaag gactaacaac tacagacaaa    1620
gtgattaata actgcaaggt tgatcaatgt catgccgcgg tcaccaatca caaaagtgg     1680 cagtataact cccctctggt cccgcgtaat gctgaacttg gggaccgaaa aggaaaaatt    1740
cacatcccgt ttccgctggc aaatgtaaca tgcagggtgc ctaaagcaag gaaccccacc    1800
gtgacgtacg ggaaaaacca agtcatcatg ctactgtatc ctgaccaccc aacactcctg    1860
tcctaccgga atatgggaga agaaccaaac tatcaagaag agtgggtgat gcataagaag    1920
gaagtcgtgc taaccgtgcc gactgaaggg ctcgaggtca cgtggggcaa caacgagccg    1980
tataagtatt ggccgcagtt atctacaaac ggtacagccc atggccaccc gcatgagata    2040
attctgtatt attatgagct gtaccctact atgactgtag tagttgtgtc agtggccacg    2100
ttcatactcc tgtcgatggt gggtatggca gcggggatgt gcatgtgtgc acgacgcaga    2160
tgcatcacac cgtatgaact gacaccagga gctaccgtcc ctttcctgct tagcctaata    2220
tgctgcatca gaacagctaa agcggccaca taccaagagg ctgcgatata cctgtggaac    2280
gagcagcaac ctttgttttg gctacaagcc cttattccgc tggcagccct gattgttcta    2340
tgcaactgtc tgagactctt accatgctgc tgtaaaacgt tggcttttt agccgtaatg    2400 agcgtcggtg cccacactgt gagcgcgtac gaacacgtaa cagtgatccc gaacacggtg    2460
ggagtaccgt ataagactct agtcaataga cctggctaca gccccatggt attggagatg    2520
gaactactgt cagtcacttt ggagccaaca ctatcgcttg attacatcac gtgcgagtac    2580
aaaaccgtca tcccgtctct gtacgtgaag tgctgcggta cagcagagtg caaggacaaa    2640
aacctacctg actacagctg taaggtcttc accggcgtct acccatttat gtggggcggc    2700
gcctactgct tctgcgacgc tgaaaacacg cagttgagcg aagcacatgt ggagaagtcc    2760
gaatcatgca aaacagaatt tgcatcagca tacaggctc ataccgcatc tgcatcagct    2820
aagctccgcg tcctttacca aggaaataac atcactgtaa ctgcctatgc aaacggcgac    2880
catgccgtca cagttaagga cgccaaattc attgtggggc caatgtcttc agcctggaca    2940
cctttcgaca acaaaattgt ggtgtacaaa ggtgacgtct ataacatgga ctaccgccc     3000 tttggcgcag aagaccagg acaatttggc gatatccaaa gtcgcacacc tgagagtgaa    3060
gacgtctatg ctaatacaca actggtactg cagagaccgg ctgcgggtac ggtacacgtg    3120
ccatactctc aggcaccatc tggctttaag tattggctaa agaacgcgg ggcgtcactg    3180 cagcacacag caccatttgg ctgccaaata gcaacaaacc cggtaagagc ggtgaactgc    3240
gccgtaggga acatgcccat ctccatcgac ataccggaag cggccttcac tagggtcgtc    3300
```

| | |
|---|---|
| gacgcgccct ctttaacgga catgtcgtgc gaggtaccag cctgcaccca ttcctcagac | 3360 |
| tttgggggcg tcgccattat taaatatgca gccagcaaga aaggcaagtg tgcggtgcat | 3420 |
| tcgatgacta acgccgtcac tattcgggaa gctgagatag aagttgaagg gaattctcag | 3480 |
| ctgcaaatct ctttctcgac ggccttagcc agcgccgaat tccgcgtaca agtctgttct | 3540 |
| acacaagtac actgtgcagc tgagtgccac cccccgaagg accacatagt caactacccg | 3600 |
| gcgtcacata ccaccctcgg ggtccaggac atctccgcta cggcgatgtc atgggtgcag | 3660 |
| aagatcacgg gaggtgtggg actggttgtt gctgttgccg cactgattct aatcgtggtg | 3720 |
| ctatgcgtgt cgttcagcag gcactaa | 3747 |

<210> SEQ ID NO 7
<211> LENGTH: 3747
<212> TYPE: DNA
<213> ORGANISM: Chikungunya virus

<400> SEQUENCE: 7

| | |
|---|---|
| atggagttca tcccaaccca aacttttttac aataggaggt accagcctcg accctggact | 60 |
| ccgcgctcta ctatccaaat catcaggccc agaccgcgcc ctcagaggca agctgggcaa | 120 |
| cttgcccagc tgatctcagc agttaataaa ctgacaatgc gcgcggtacc ccaacagaag | 180 |
| ccacgcagga atcggaagaa taagaagcaa aagcaaaaac aacaggcgcc acaaaacaac | 240 |
| acaaatcaaa agaagcagcc acctaaaaag aaaccggctc aaaagaaaaa gaagccgggc | 300 |
| cgcagagaga ggatgtgcat gaaaatcgaa aatgattgta ttttcgaagt caagcacgaa | 360 |
| ggtaaggtaa caggttacgc gtgcctggtg ggggacaaag taatgaaacc agcacacgta | 420 |
| aaggggacca tcgataacgc ggacctggcc aaactggcct ttaagcggtc atctaagtat | 480 |
| gaccttgaat gcgcgcagat accgtgcaca atgaagtccg acgcttcgaa gttcacccat | 540 |
| gagaaaccgg aggggtacta caactggcac cacggagcag tacagtactc aggaggccgg | 600 |
| ttcaccatcc ctacaggtgc tggcaaacca ggggacagcg gcagacctat cttcgacaac | 660 |
| aagggacgcg tggtggccat agtcttagga ggagctaatg aaggagcccg tacagccctc | 720 |
| tcggtggtga cctggaataa agacattgtc actaaaatca cccccgaggg ggccgaagag | 780 |
| tggagtcttg ccatcccagt tatgtgcctg ttggcaaaca ccacgttccc ctgctcccag | 840 |
| ccccccttgca cgcctgctg ctacgaaaag gaaccggagg aaacccctacg catgcttgag | 900 |
| gacaacgtca tgagacctgg gtactatcag ctgctacaag catccttaac atgttctccc | 960 |
| caccgccagc gacgcagcac caaggacaac ttcaatgtct ataaagccac aagaccatac | 1020 |
| ttagctcact gtcccgactg tggagaaggg cactcgtgcc atagtcccgt agcactagaa | 1080 |
| cgcatcagaa atgaagcgac agacgggacg ctgaaaatcc aggtctcctt gcaaatcgga | 1140 |
| ataaagacgg atgacagcca cgattggacc aagctgcgtt atatggacaa ccacatgcca | 1200 |
| gcagacgcag agagggcggg gctatttgta agaacatcag caccgtgtac gattactgga | 1260 |
| acaatgggac acttcatcct ggcccgatgt ccaaagggg aaactctgac ggtgggattc | 1320 |
| actgacagta ggaagattag tcactcatgt acgcacccat ttcaccacga ccctcctgtg | 1380 |
| ataggtcggg aaaaattcca ttcccgaccg cagcacggta aagagctacc ttgcagcacg | 1440 |
| tacgtgcaga gcaccgccgc aactaccgag gagatagagg tacacatgcc cccagacacc | 1500 |
| cctgatcgca cattaatgtc acaacagtcc ggcaacgtaa agatcacagt caatggccag | 1560 |
| acggtgcggt acagtgtaa ttgcggtggc tcaaatgaag gactaacaac tacagacaaa | 1620 |
| gtgattaata actgcaaggt tgatcaatgt catgccgcgg tcaccaatca caaaaagtgg | 1680 |

-continued

```
cagtataact cccctctggt cccgcgtaat gctgaacttg gggaccgaaa aggaaaaatt    1740
cacatcccgt ttccgctggc aaatgtaaca tgcagggtgc ctaaagcaag gaaccccacc    1800
gtgacgtacg ggaaaaacca agtcatcatg ctactgtatc ctgaccaccc aacactcctg    1860
tcctaccgga atatgggaga agaaccaaac tatcaagaag agtgggtgat gcataagaag    1920
gaagtcgtgc taaccgtgcc gactgaaggg ctcgaggtca cgtggggcaa caacgagccg    1980
tataagtatt ggccgcagtt atctacaaac ggtacagccc atggccaccc gcatgagata    2040
attctgtatt attatgagct gtaccccact atgactgtag tagttgtgtc agtggccacg    2100
ttcatactcc tgtcgatggt gggtatggca gcggggatgt gcatgtgtgc acgacgcaga    2160
tgcatcacac cgtatgaact gacaccagga gctaccgtcc ctttcctgct tagcctaata    2220
tgctgcatca gaacagctaa agcggccaca taccaagagg ctgcgatata cctgtggaac    2280
gagcagcaac ctttgttttg gctacaagcc cttattccgc tggcagccct gattgttcta    2340
tgcaactgtc tgagactctt accatgctgc tgtaaaacgt tggctttttt agccgtaatg    2400
agcgtcggtg cccacactgt gagcgcgtac gaacacgtaa cagtgatccc gaacacggtg    2460
ggagtaccgt ataagactct agtcaataga cctggctaca gccccatggt attggagatg    2520
gaactactgt cagtcacttt ggagccaaca ctatcgcttg attacatcac gtgcgagtac    2580
aaaaccgtca tcccgtctcc gtacgtgaag tgctgcggta cagcagagtg caaggacaaa    2640
aacctacctg actacagctg tagggtcttc accggcgtct acccatttat gtggggtggc    2700
gcctactgct tctgcgacgc tgaaaacacg cagttgagcg aagcacatgt ggagaagtcc    2760
gaatcatgca aaacagaatt tgcatcagca tacagggctc ataccgcatc tgcatcagct    2820
aagctccgcg tcctttacca aggaaataac atcactgtaa ctgccatagc aaacggcgac    2880
catgccgtca cagttaagga cgccaaattc attgtggggc caatgtcttc agcctggaca    2940
cctttcgaca caaaaattgt ggtgtacaaa ggtgacgtct ataacatgga ctacccgccc    3000 tttgcgcag gaagaccagg acaatttggc gatatccaaa gtcgcacacc tgagagtaaa    3060
gacgtctatg ctaatacaca actggtactg cagagaccgg ctgcgggtac ggtacacgtg    3120
ccatactctc aggcaccatc tggctttaag tattggctaa agaacgcgg ggcgtcactg    3180 cagcacacag caccatttgg ctgccaaata gcaacaaacc cggtaagagc ggtgaactgc    3240
gccgtaggga acatgcccat ctccatcgac ataccggaag cggccttcac tagggtcgtc    3300
gacgcgccct ctttaacgga catgtcgtgc gaggtaccag cctgcaccca ttcctcagac    3360
tttgggggcg tcgccattat taaatatgca gccagcaaga aggcaagtg tgcggtgcat    3420 tcgatgacta acgccgtcac tattcgggaa gctgagatag aagttgaagg gaattctcag    3480
ctgcaaatct ctttctcgac ggccttagcc agcgccgaat ccgcgtaca gtctgttct    3540 acacaagtac actgtgcagc tgagtgccac cccccgaagg accacatagt caactacccg    3600
gcgtcacata ccaccctcgg ggtccaggac atctccgcta cggcgatgtc atgggtgcag    3660
aagatcacgg gaggtgtggg actggttgtt gctgttgccg cactgattct aatcgtggtg    3720
ctatgcgtgt cgttcagcag gcactaa                                       3747
```

<210> SEQ ID NO 8
<211> LENGTH: 1248
<212> TYPE: PRT
<213> ORGANISM: Chikungunya virus

<400> SEQUENCE: 8

-continued

```
Met Glu Phe Ile Pro Thr Gln Thr Phe Tyr Asn Arg Arg Tyr Gln Pro
1               5                   10                  15

Arg Pro Trp Thr Pro Arg Ser Thr Ile Gln Ile Arg Pro Arg Pro
            20                  25                  30

Arg Pro Gln Arg Gln Ala Gly Gln Leu Ala Gln Leu Ile Ser Ala Val
                35                  40                  45

Asn Lys Leu Thr Met Arg Ala Val Pro Gln Lys Pro Arg Arg Asn
50                  55                  60

Arg Lys Asn Lys Lys Gln Lys Gln Gln Ala Pro Gln Asn Asn
65              70              75              80

Thr Asn Gln Lys Lys Gln Pro Pro Lys Lys Pro Ala Gln Lys Lys
            85                  90                  95

Lys Lys Pro Gly Arg Arg Glu Arg Met Cys Met Lys Ile Glu Asn Asp
        100                 105                 110

Cys Ile Phe Glu Val Lys His Glu Gly Lys Val Thr Gly Tyr Ala Cys
            115                 120                 125

Leu Val Gly Asp Lys Val Met Lys Pro Ala His Val Lys Gly Thr Ile
        130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
            165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
            195                 200                 205

Lys Pro Gly Asp Ser Gly Arg Pro Ile Phe Asp Asn Lys Gly Arg Val
        210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
            245                 250                 255

Gly Ala Glu Glu Trp Ser Leu Ala Ile Pro Val Met Cys Leu Leu Ala
        260                 265                 270

Asn Thr Thr Phe Pro Cys Ser Gln Pro Pro Cys Thr Pro Cys Cys Tyr
    275                 280                 285

Glu Lys Glu Pro Glu Glu Thr Leu Arg Met Leu Glu Asp Asn Val Met
        290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Arg Ile Lys Thr Asp
        370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
```

```
                420             425             430
Gly Glu Thr Leu Thr Val Gly Phe Thr Asp Ser Arg Lys Ile Ser His
            435             440             445

Ser Cys Thr His Pro Phe His His Asp Pro Val Ile Gly Arg Glu
450             455             460

Lys Phe His Ser Arg Pro Gln His Gly Lys Glu Leu Pro Cys Ser Thr
465             470             475             480

Tyr Val Gln Ser Thr Ala Ala Thr Thr Glu Glu Ile Glu Val His Met
            485             490             495

Pro Pro Asp Thr Pro Asp Arg Thr Leu Met Ser Gln Gln Ser Gly Asn
            500             505             510

Val Lys Ile Thr Val Asn Gly Gln Thr Val Arg Tyr Lys Cys Asn Cys
            515             520             525

Gly Gly Ser Asn Glu Gly Leu Thr Thr Thr Asp Lys Val Ile Asn Asn
            530             535             540

Cys Lys Val Asp Gln Cys His Ala Ala Val Thr Asn His Lys Lys Trp
545             550             555             560

Gln Tyr Asn Ser Pro Leu Val Pro Arg Asn Ala Glu Leu Gly Asp Arg
            565             570             575

Lys Gly Lys Ile His Ile Pro Phe Pro Leu Ala Asn Ala Thr Cys Arg
            580             585             590

Val Pro Lys Ala Arg Asn Pro Thr Val Thr Tyr Gly Lys Asn Gln Val
            595             600             605

Ile Met Leu Leu Tyr Pro Asp His Pro Thr Leu Leu Ser Tyr Arg Asn
            610             615             620

Met Gly Glu Glu Pro Asn Tyr Gln Glu Glu Trp Val Met His Lys Lys
625             630             635             640

Glu Val Val Leu Thr Val Pro Thr Glu Gly Leu Glu Val Thr Trp Gly
            645             650             655

Asn Asn Glu Pro Tyr Lys Tyr Trp Pro Gln Leu Ser Thr Asn Gly Thr
            660             665             670

Ala His Gly His Pro His Glu Ile Ile Leu Tyr Tyr Tyr Glu Leu Tyr
            675             680             685

Pro Thr Met Thr Val Val Val Ser Val Ala Thr Phe Ile Leu Leu
            690             695             700

Ser Met Val Gly Met Ala Ala Gly Met Cys Met Cys Ala Arg Arg Arg
705             710             715             720

Cys Ile Thr Pro Tyr Glu Leu Thr Pro Gly Ala Thr Val Pro Phe Leu
            725             730             735

Leu Ser Leu Ile Cys Cys Ile Arg Thr Ala Lys Ala Ala Thr Tyr Gln
            740             745             750

Glu Ala Ala Ile Tyr Leu Trp Asn Glu Gln Gln Pro Leu Phe Trp Leu
            755             760             765

Gln Ala Leu Ile Pro Leu Ala Ala Leu Ile Val Leu Cys Asn Cys Leu
            770             775             780

Arg Leu Leu Pro Cys Cys Cys Lys Thr Leu Ala Phe Leu Ala Val Met
785             790             795             800

Ser Val Gly Ala His Thr Val Ser Ala Tyr Glu His Val Thr Val Ile
            805             810             815

Pro Asn Thr Val Gly Val Pro Tyr Lys Thr Leu Val Asn Arg Pro Gly
            820             825             830

Tyr Ser Pro Met Val Leu Glu Met Glu Leu Leu Ser Val Thr Leu Glu
            835             840             845
```

```
Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                    885                 890                 895

Met Trp Gly Gly Ala Tyr Cys Phe Cys Asp Ala Glu Asn Thr Gln Leu
                900                 905                 910

Ser Glu Ala His Val Glu Lys Ser Glu Ser Cys Lys Thr Glu Phe Ala
            915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                    965                 970                 975

Ser Ala Trp Thr Pro Phe Asp Asn Lys Ile Val Val Tyr Lys Gly Asp
                980                 985                 990

Val Tyr Asn Met Asp Tyr Pro Pro Phe Gly Ala Gly Arg Pro Gly Gln
            995                 1000                1005

Phe Gly Asp Ile Gln Ser Arg Thr Pro Glu Ser Glu Asp Val Tyr
    1010                1015                1020

Ala Asn Thr Gln Leu Val Leu Gln Arg Pro Ala Ala Gly Thr Val
    1025                1030                1035

His Val Pro Tyr Ser Gln Ala Pro Ser Gly Phe Lys Tyr Trp Leu
    1040                1045                1050

Lys Glu Arg Gly Ala Ser Leu Gln His Thr Ala Pro Phe Gly Cys
    1055                1060                1065

Gln Ile Ala Thr Asn Pro Val Arg Ala Val Asn Cys Ala Val Gly
    1070                1075                1080

Asn Met Pro Ile Ser Ile Asp Ile Pro Glu Ala Ala Phe Thr Arg
    1085                1090                1095

Val Val Asp Ala Pro Ser Leu Thr Asp Met Ser Cys Glu Val Pro
    1100                1105                1110

Ala Cys Thr His Ser Ser Asp Phe Gly Gly Val Ala Ile Ile Lys
    1115                1120                1125

Tyr Ala Ala Ser Lys Lys Gly Lys Cys Ala Val His Ser Met Thr
    1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245
```

<210> SEQ ID NO 9
<211> LENGTH: 1248
<212> TYPE: PRT
<213> ORGANISM: Chikungunya virus

<400> SEQUENCE: 9

Met Glu Phe Ile Pro Thr Gln Thr Phe Tyr Asn Arg Arg Tyr Gln Pro
1               5                   10                  15

Arg Pro Trp Thr Pro Arg Ser Thr Ile Gln Ile Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asn Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

```
Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
            405                 410                 415

Thr Ile Thr Gly Thr Met Gly His Phe Ile Leu Ala Arg Cys Pro Lys
        420                 425                 430

Gly Glu Thr Leu Thr Val Gly Phe Thr Asp Ser Arg Lys Ile Ser His
    435                 440                 445

Ser Cys Thr His Pro Phe His His Asp Pro Val Ile Gly Arg Glu
450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
            485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
            515                 520                 525

Gly Gly Ser Asn Glu Gly Leu Thr Thr Thr Asp Lys Val Ile Asn Asn
530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
            565                 570                 575

Lys Gly Lys Ile His Ile Pro Phe Pro Leu Ala Asn Ala Thr Cys Arg
            580                 585                 590

Val Pro Lys Ala Arg Asn Pro Thr Val Thr Tyr Gly Lys Asn Gln Val
            595                 600                 605

Ile Met Leu Leu Tyr Pro Asp His Pro Thr Leu Leu Ser Tyr Arg Asn
            610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
            675                 680                 685

Pro Thr Met Thr Val Val Val Ser Val Ala Thr Phe Ile Leu Leu
        690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
                740                 745                 750

Glu Ala Ala Ile Tyr Leu Trp Asn Glu Gln Gln Pro Leu Phe Trp Leu
            755                 760                 765

Gln Ala Leu Ile Pro Leu Ala Ala Leu Ile Val Leu Cys Asn Cys Leu
            770                 775                 780

Arg Leu Leu Pro Cys Cys Cys Lys Thr Leu Ala Phe Leu Ala Val Met
785                 790                 795                 800
```

-continued

Ser Val Gly Ala His Thr Val Ser Ala Tyr Glu His Val Thr Val Ile
                    805                 810                 815

Pro Asn Thr Val Gly Val Pro Tyr Lys Thr Leu Val Asn Arg Pro Gly
                820                 825                 830

Tyr Ser Pro Met Val Leu Glu Met Glu Leu Leu Ser Val Thr Leu Glu
            835                 840                 845

Pro Thr Leu Ser Leu Asp Tyr Ile Thr Cys Glu Tyr Lys Thr Val Ile
850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Arg Arg  Pro Gly Gln
        995                 1000                1005

Phe Gly  Asp Ile Gln Ser Arg  Thr Pro Glu Ser Glu  Asp Val Tyr
    1010                1015                1020

Ala Asn  Thr Gln Leu Val Leu  Gln Arg Pro Ala Ala  Gly Thr Val
    1025                1030                1035

His Val  Pro Tyr Ser Gln Ala  Pro Ser Gly Phe Lys  Tyr Trp Leu
    1040                1045                1050

Lys Glu  Arg Gly Ala Ser Leu  Gln His Thr Ala Pro  Phe Gly Cys
    1055                1060                1065

Gln Ile  Ala Thr Asn Pro Val  Arg Ala Val Asn Cys  Ala Val Gly
    1070                1075                1080

Asn Met  Pro Ile Ser Ile Asp  Ile Pro Glu Ala Ala  Phe Thr Arg
    1085                1090                1095

Val Val  Asp Ala Pro Ser Leu  Thr Asp Met Ser Cys  Glu Val Pro
    1100                1105                1110

Ala Cys  Thr His Ser Ser Asp  Phe Gly Gly Val Ala  Ile Ile Lys
    1115                1120                1125

Tyr Ala  Ala Ser Lys Lys Gly  Lys Cys Ala Val His  Ser Met Thr
    1130                1135                1140

Asn Ala  Val Thr Ile Arg Glu  Ala Glu Ile Glu Val  Glu Gly Asn
    1145                1150                1155

Ser Gln  Leu Gln Ile Ser Phe  Ser Thr Ala Leu Ala  Ser Ala Glu
    1160                1165                1170

Phe Arg  Val Gln Val Cys Ser  Thr Gln Val His Cys  Ala Ala Glu
    1175                1180                1185

Cys His  Pro Pro Lys Asp His  Ile Val Asn Tyr Pro  Ala Ser His
    1190                1195                1200

Thr Thr  Leu Gly Val Gln Asp  Ile Ser Ala Thr Ala  Met Ser Trp

```
                  1205                1210                1215
Val Gln Lys Ile Thr Gly Gly Val Gly Leu Val Val Ala Val Ala
              1220                1225                1230

Ala Leu Ile Leu Ile Val Val Leu Cys Val Ser Phe Ser Arg His
              1235                1240                1245

<210> SEQ ID NO 10
<211> LENGTH: 1248
<212> TYPE: PRT
<213> ORGANISM: Chikungunya virus

<400> SEQUENCE: 10

Met Glu Phe Ile Pro Thr Gln Thr Phe Tyr Asn Arg Arg Tyr Gln Pro
1               5                   10                  15

Arg Pro Trp Thr Pro Arg Ser Thr Ile Gln Ile Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
50                  55                  60

Arg Lys Asn Lys Lys Gln Lys Gln Lys Gln Gln Ala Pro Gln Asn Asn
65                  70                  75                  80

Thr Asn Gln Lys Lys Gln Pro Pro Lys Lys Pro Ala Gln Lys Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335
```

```
Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Asn Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Ala Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Val Ser Val Ala Thr Phe Ile Leu Leu
    690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
```

```
                755                 760                 765
Gln Ala Leu Ile Pro Leu Ala Ala Leu Ile Val Leu Cys Asn Cys Leu
770                 775                 780
Arg Leu Leu Pro Cys Cys Cys Lys Thr Leu Ala Phe Leu Ala Val Met
785                 790                 795                 800
Ser Val Gly Ala His Thr Val Ser Ala Tyr Glu His Val Thr Val Ile
                805                 810                 815
Pro Asn Thr Val Gly Val Pro Tyr Lys Thr Leu Val Asn Arg Pro Gly
                820                 825                 830
Tyr Ser Pro Met Val Leu Glu Met Glu Leu Leu Ser Val Thr Leu Glu
                835                 840                 845
Pro Thr Leu Ser Leu Asp Tyr Ile Thr Cys Glu Tyr Lys Thr Val Ile
                850                 855                 860
Pro Ser Pro Tyr Val Lys Cys Cys Gly Thr Ala Glu Cys Lys Asp Lys
865                 870                 875                 880
Asn Leu Pro Asp Tyr Ser Cys Lys Val Phe Thr Gly Val Tyr Pro Phe
                885                 890                 895
Met Trp Gly Gly Ala Tyr Cys Phe Cys Asp Ala Glu Asn Thr Gln Leu
                900                 905                 910
Ser Glu Ala His Val Glu Lys Ser Glu Ser Cys Lys Thr Glu Phe Ala
                915                 920                 925
Ser Ala Tyr Arg Ala His Thr Ala Ser Ala Ser Ala Lys Leu Arg Val
                930                 935                 940
Leu Tyr Gln Gly Asn Asn Ile Thr Val Thr Ala Tyr Ala Asn Gly Asp
945                 950                 955                 960
His Ala Val Thr Val Lys Asp Ala Lys Phe Ile Val Gly Pro Met Ser
                965                 970                 975
Ser Ala Trp Thr Pro Phe Asp Asn Lys Ile Val Val Tyr Lys Gly Asp
                980                 985                 990
Val Tyr Asn Met Asp Tyr Pro Pro Phe Gly Ala Gly Arg Pro Gly Gln
                995                 1000                1005
Phe Gly Asp Ile Gln Ser Arg Thr Pro Glu Ser Glu Asp Val Tyr
                1010                1015                1020
Ala Asn Thr Gln Leu Val Leu Gln Arg Pro Ala Ala Gly Thr Val
                1025                1030                1035
His Val Pro Tyr Ser Gln Ala Pro Ser Gly Phe Lys Tyr Trp Leu
                1040                1045                1050
Lys Glu Arg Gly Ala Ser Leu Gln His Thr Ala Pro Phe Gly Cys
                1055                1060                1065
Gln Ile Ala Thr Asn Pro Val Arg Ala Val Asn Cys Ala Val Gly
                1070                1075                1080
Asn Met Pro Ile Ser Ile Asp Ile Pro Glu Ala Ala Phe Thr Arg
                1085                1090                1095
Val Val Asp Ala Pro Ser Leu Thr Asp Met Ser Cys Glu Val Pro
                1100                1105                1110
Ala Cys Thr His Ser Ser Asp Phe Gly Gly Val Ala Ile Ile Lys
                1115                1120                1125
Tyr Ala Ala Ser Lys Lys Gly Lys Cys Ala Val His Ser Met Thr
                1130                1135                1140
Asn Ala Val Thr Ile Arg Glu Ala Glu Ile Glu Val Glu Gly Asn
                1145                1150                1155
Ser Gln Leu Gln Ile Ser Phe Ser Thr Ala Leu Ala Ser Ala Glu
                1160                1165                1170
```

```
Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245

<210> SEQ ID NO 11
<211> LENGTH: 1248
<212> TYPE: PRT
<213> ORGANISM: Chikungunya virus

<400> SEQUENCE: 11

Met Glu Phe Ile Pro Thr Gln Thr Phe Tyr Asn Arg Arg Tyr Gln Pro
1                   5                   10                  15

Arg Pro Trp Thr Pro Arg Ser Thr Ile Gln Ile Ile Arg Pro Arg Pro
                20                  25                  30

Arg Pro Gln Arg Gln Ala Gly Gln Leu Ala Gln Leu Ile Ser Ala Val
            35                  40                  45

Asn Lys Leu Thr Met Arg Ala Val Pro Gln Gln Lys Pro Arg Arg Asn
50                  55                  60

Arg Lys Asn Lys Lys Gln Lys Gln Lys Gln Ala Pro Gln Asn Asn
65                  70                  75                  80

Thr Asn Gln Lys Lys Gln Pro Pro Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Val Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
```

-continued

```
            290                 295                 300
Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
                340                 345                 350

Cys His Ser Pro Val Ala Leu Glu Arg Ile Arg Asn Glu Ala Thr Asp
                355                 360                 365

Gly Thr Leu Lys Ile Gln Val Ser Leu Gln Ile Gly Ile Lys Thr Asp
        370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
                420                 425                 430

Gly Glu Thr Leu Thr Val Gly Phe Thr Asp Ser Arg Lys Ile Ser His
                435                 440                 445

Ser Cys Thr His Pro Phe His His Asp Pro Val Ile Gly Arg Glu
        450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
                500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
        530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Ala Thr Cys Arg
                580                 585                 590

Val Pro Lys Ala Arg Asn Pro Thr Val Thr Tyr Gly Lys Asn Gln Val
                595                 600                 605

Ile Met Leu Leu Tyr Pro Asp His Pro Thr Leu Leu Ser Tyr Arg Asn
        610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
                660                 665                 670

Ala His Gly His Pro His Glu Ile Ile Leu Tyr Tyr Tyr Glu Leu Tyr
                675                 680                 685

Pro Thr Met Thr Val Val Val Ser Val Ala Thr Phe Ile Leu Leu
        690                 695                 700

Ser Met Val Gly Met Ala Ala Gly Met Cys Met Cys Ala Arg Arg Arg
705                 710                 715                 720
```

```
Cys Ile Thr Pro Tyr Glu Leu Thr Pro Gly Ala Thr Val Pro Phe Leu
            725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
            755                 760                 765

Gln Ala Leu Ile Pro Leu Ala Ala Leu Ile Val Leu Cys Asn Cys Leu
            770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
            805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
            835                 840                 845

Pro Thr Leu Ser Leu Asp Tyr Ile Thr Cys Glu Tyr Lys Thr Val Ile
            850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
            885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
            915                 920                 925

Ser Ala Tyr Arg Ala His Thr Ala Ser Ala Ser Ala Lys Leu Arg Val
930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
            965                 970                 975

Ser Ala Trp Thr Pro Phe Asp Asn Lys Ile Val Val Tyr Lys Gly Asp
            980                 985                 990

Val Tyr Asn Met Asp Tyr Pro Pro Phe Gly Ala Arg Arg Pro Gly Gln
            995                 1000                1005

Phe Gly Asp Ile Gln Ser Arg Thr Pro Glu Ser Glu Asp Val Tyr
            1010                1015                1020

Ala Asn Thr Gln Leu Val Leu Gln Arg Pro Ala Ala Gly Thr Val
            1025                1030                1035

His Val Pro Tyr Ser Gln Ala Pro Ser Gly Phe Lys Tyr Trp Leu
            1040                1045                1050

Lys Glu Arg Gly Ala Ser Leu Gln His Thr Ala Pro Phe Gly Cys
            1055                1060                1065

Gln Ile Ala Thr Asn Pro Val Arg Ala Val Asn Cys Ala Val Gly
            1070                1075                1080

Asn Met Pro Ile Ser Ile Asp Ile Pro Glu Ala Ala Phe Thr Arg
            1085                1090                1095

Val Val Asp Ala Pro Ser Leu Thr Asp Met Ser Cys Glu Val Pro
            1100                1105                1110

Ala Cys Thr His Ser Ser Asp Phe Gly Gly Val Ala Ile Ile Lys
            1115                1120                1125
```

```
Tyr Ala Ala Ser Lys Lys Gly Lys Cys Ala Val His Ser Met Thr
    1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245

<210> SEQ ID NO 12
<211> LENGTH: 1248
<212> TYPE: PRT
<213> ORGANISM: Chikungunya virus

<400> SEQUENCE: 12

Met Glu Phe Ile Pro Thr Gln Thr Phe Tyr Asn Arg Arg Tyr Gln Pro
1               5                   10                  15

Arg Pro Trp Thr Pro Arg Ser Thr Ile Gln Ile Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
50                  55                  60

Arg Lys Asn Lys Lys Gln Lys Gln Lys Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255
```

```
Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Glu Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Asp Lys Val Ile Asn Asn
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Ala Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670
```

-continued

```
Ala His Gly His Pro His Glu Ile Ile Leu Tyr Tyr Glu Leu Tyr
        675             680             685

Pro Thr Met Thr Val Val Val Ser Val Ala Thr Phe Ile Leu Leu
    690             695             700

Ser Met Val Gly Met Ala Ala Gly Met Cys Met Cys Ala Arg Arg Arg
705             710             715             720

Cys Ile Thr Pro Tyr Glu Leu Thr Pro Gly Ala Thr Val Pro Phe Leu
                725             730             735

Leu Ser Leu Ile Cys Cys Ile Arg Thr Ala Lys Ala Ala Thr Tyr Gln
            740             745             750

Glu Ala Ala Ile Tyr Leu Trp Asn Glu Gln Gln Pro Leu Phe Trp Leu
        755             760             765

Gln Ala Leu Ile Pro Leu Ala Ala Leu Ile Val Leu Cys Asn Cys Leu
    770             775             780

Arg Leu Leu Pro Cys Cys Cys Lys Thr Leu Ala Phe Leu Ala Val Met
785             790             795             800

Ser Val Gly Ala His Thr Val Ser Ala Tyr Glu His Val Thr Val Ile
                805             810             815

Pro Asn Thr Val Gly Val Pro Tyr Lys Thr Leu Val Asn Arg Pro Gly
            820             825             830

Tyr Ser Pro Met Val Leu Glu Met Glu Leu Leu Ser Val Thr Leu Glu
        835             840             845

Pro Thr Leu Ser Leu Asp Tyr Ile Thr Cys Glu Tyr Lys Thr Val Ile
    850             855             860

Pro Ser Pro Tyr Val Lys Cys Cys Gly Thr Ala Glu Cys Lys Asp Lys
865             870             875             880

Asn Leu Pro Asp Tyr Ser Cys Lys Val Phe Thr Gly Val Tyr Pro Phe
                885             890             895

Met Trp Gly Gly Ala Tyr Cys Phe Cys Asp Ala Glu Asn Thr Gln Leu
            900             905             910

Ser Glu Ala His Val Glu Lys Ser Glu Ser Cys Lys Thr Glu Phe Ala
        915             920             925

Ser Ala Tyr Arg Ala His Thr Ala Ser Ala Ser Ala Lys Leu Arg Val
    930             935             940

Leu Tyr Gln Gly Asn Asn Ile Thr Val Thr Ala Tyr Ala Asn Gly Asp
945             950             955             960

His Ala Val Thr Val Lys Asp Ala Lys Phe Ile Val Gly Pro Met Ser
                965             970             975

Ser Ala Trp Thr Pro Phe Asp Asn Lys Ile Val Val Tyr Lys Gly Asp
            980             985             990

Val Tyr Asn Met Asp Tyr Pro Pro Phe Gly Ala Gly Arg Pro Gly Gln
        995             1000            1005

Phe Gly Asp Ile Gln Ser Arg Thr Pro Glu Ser Glu Asp Val Tyr
    1010            1015           1020

Ala Asn Thr Gln Leu Val Leu Gln Arg Pro Ala Ala Gly Thr Val
    1025            1030           1035

His Val Pro Tyr Ser Gln Ala Pro Ser Gly Phe Lys Tyr Trp Leu
    1040            1045           1050

Lys Glu Arg Gly Ala Ser Leu Gln His Thr Ala Pro Phe Gly Cys
    1055            1060           1065

Gln Ile Ala Thr Asn Pro Val Arg Ala Val Asn Cys Ala Val Gly
    1070            1075           1080

Asn Met Pro Ile Ser Ile Asp Ile Pro Glu Ala Ala Phe Thr Arg
```

```
                 1085                1090                1095

Val Val Asp Ala Pro Ser Leu Thr Asp Met Ser Cys Glu Val Pro
        1100                1105                1110

Ala Cys Thr His Ser Ser Asp Phe Gly Gly Val Ala Ile Ile Lys
        1115                1120                1125

Tyr Ala Ala Ser Lys Lys Gly Lys Cys Ala Val His Ser Met Thr
        1130                1135                1140

Asn Ala Val Thr Ile Arg Glu Ala Glu Ile Glu Val Glu Gly Asn
        1145                1150                1155

Ser Gln Leu Gln Ile Ser Phe Ser Thr Ala Leu Ala Ser Ala Glu
        1160                1165                1170

Phe Arg Val Gln Val Cys Ser Thr Gln Val His Cys Ala Ala Glu
        1175                1180                1185

Cys His Pro Pro Lys Asp His Ile Val Asn Tyr Pro Ala Ser His
        1190                1195                1200

Thr Thr Leu Gly Val Gln Asp Ile Ser Ala Thr Ala Met Ser Trp
        1205                1210                1215

Val Gln Lys Ile Thr Gly Gly Val Gly Leu Val Val Ala Val Ala
        1220                1225                1230

Ala Leu Ile Leu Ile Val Val Leu Cys Val Ser Phe Ser Arg His
        1235                1240                1245

<210> SEQ ID NO 13
<211> LENGTH: 1248
<212> TYPE: PRT
<213> ORGANISM: Chikungunya virus

<400> SEQUENCE: 13

Met Glu Phe Ile Pro Thr Gln Thr Phe Tyr Asn Arg Arg Tyr Gln Pro
1               5                   10                  15

Arg Pro Trp Thr Pro Arg Ser Thr Ile Gln Ile Ile Arg Pro Arg Pro
                20                  25                  30

Arg Pro Gln Arg Gln Ala Gly Gln Leu Ala Gln Leu Ile Ser Ala Val
            35                  40                  45

Asn Lys Leu Thr Met Arg Ala Val Pro Gln Gln Lys Pro Arg Arg Asn
        50                  55                  60

Arg Lys Asn Lys Lys Gln Lys Gln Lys Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205
```

-continued

```
Lys Pro Gly Asp Ser Gly Arg Pro Ile Phe Asp Asn Lys Gly Arg Val
210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
            245                 250                 255

Gly Ala Glu Glu Trp Ser Leu Ala Ile Pro Val Met Cys Leu Leu Ala
        260                 265                 270

Asn Thr Thr Phe Pro Cys Ser Gln Pro Cys Thr Pro Cys Cys Tyr
            275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Arg Ile Lys Thr Asp
370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
610                 615                 620

Met Gly Glu Glu Pro Asn Tyr Gln Glu Glu Trp Val Met His Lys Lys
```

-continued

```
            625                 630                 635                 640
        Glu Val Val Leu Thr Val Pro Thr Glu Gly Leu Glu Val Thr Trp Gly
                            645                 650                 655

Asn Asn Glu Pro Tyr Lys Tyr Trp Pro Gln Leu Ser Thr Asn Gly Thr
                            660                 665                 670

Ala His Gly His Pro His Glu Ile Ile Leu Tyr Tyr Glu Leu Tyr
                        675                 680                 685

Pro Thr Met Thr Val Val Val Ser Val Ala Thr Phe Ile Leu Leu
                690                 695                 700

Ser Met Val Gly Met Ala Ala Gly Met Cys Met Cys Ala Arg Arg Arg
        705                 710                 715                 720

Cys Ile Thr Pro Tyr Glu Leu Thr Pro Gly Ala Thr Val Pro Phe Leu
                            725                 730                 735

Leu Ser Leu Ile Cys Cys Ile Arg Thr Ala Lys Ala Ala Thr Tyr Gln
                            740                 745                 750

Glu Ala Ala Ile Tyr Leu Trp Asn Glu Gln Gln Pro Leu Phe Trp Leu
                            755                 760                 765

Gln Ala Leu Ile Pro Leu Ala Ala Leu Ile Val Leu Cys Asn Cys Leu
                            770                 775                 780

Arg Leu Leu Pro Cys Cys Cys Lys Thr Leu Ala Phe Leu Ala Val Met
        785                 790                 795                 800

Ser Val Gly Ala His Thr Val Ser Ala Tyr Glu His Val Thr Val Ile
                            805                 810                 815

Pro Asn Thr Val Gly Val Pro Tyr Lys Thr Leu Val Asn Arg Pro Gly
                            820                 825                 830

Tyr Ser Pro Met Val Leu Glu Met Glu Leu Leu Ser Val Thr Leu Glu
                            835                 840                 845

Pro Thr Leu Ser Leu Asp Tyr Ile Thr Cys Glu Tyr Lys Thr Val Ile
                    850                 855                 860

Pro Ser Leu Tyr Val Lys Cys Cys Gly Thr Ala Glu Cys Lys Asp Lys
        865                 870                 875                 880

Asn Leu Pro Asp Tyr Ser Cys Lys Val Phe Thr Gly Val Tyr Pro Phe
                            885                 890                 895

Met Trp Gly Gly Ala Tyr Cys Phe Cys Asp Ala Glu Asn Thr Gln Leu
                            900                 905                 910

Ser Glu Ala His Val Glu Lys Ser Glu Ser Cys Lys Thr Glu Phe Ala
                            915                 920                 925

Ser Ala Tyr Arg Ala His Thr Ala Ser Ala Ser Ala Lys Leu Arg Val
                    930                 935                 940

Leu Tyr Gln Gly Asn Asn Ile Thr Val Thr Ala Tyr Ala Asn Gly Asp
        945                 950                 955                 960

His Ala Val Thr Val Lys Asp Ala Lys Phe Ile Val Gly Pro Met Ser
                            965                 970                 975

Ser Ala Trp Thr Pro Phe Asp Asn Lys Ile Val Val Tyr Lys Gly Asp
                            980                 985                 990

Val Tyr Asn Met Asp Tyr Pro Pro  Phe Gly Ala Gly Arg  Pro Gly Gln
                            995                 1000                 1005

Phe Gly  Asp Ile Gln Ser Arg  Thr Pro Glu Ser Glu  Asp Val Tyr
                 1010                 1015                 1020

Ala Asn  Thr Gln Leu Val Leu  Gln Arg Pro Ala Ala  Gly Thr Val
                 1025                 1030                 1035

His Val  Pro Tyr Ser Gln Ala  Pro Ser Gly Phe Lys  Tyr Trp Leu
                 1040                 1045                 1050
```

```
Lys Glu Arg Gly Ala Ser Leu Gln His Thr Ala Pro Phe Gly Cys
    1055                1060                1065

Gln Ile Ala Thr Asn Pro Val Arg Ala Val Asn Cys Ala Val Gly
    1070                1075                1080

Asn Met Pro Ile Ser Ile Asp Ile Pro Glu Ala Ala Phe Thr Arg
    1085                1090                1095

Val Val Asp Ala Pro Ser Leu Thr Asp Met Ser Cys Glu Val Pro
    1100                1105                1110

Ala Cys Thr His Ser Ser Asp Phe Gly Gly Val Ala Ile Ile Lys
    1115                1120                1125

Tyr Ala Ala Ser Lys Lys Gly Lys Cys Ala Val His Ser Met Thr
    1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245

<210> SEQ ID NO 14
<211> LENGTH: 1248
<212> TYPE: PRT
<213> ORGANISM: Chikungunya virus

<400> SEQUENCE: 14

Met Glu Phe Ile Pro Thr Gln Thr Phe Tyr Asn Arg Arg Tyr Gln Pro
1               5                   10                  15

Arg Pro Trp Thr Pro Arg Ser Thr Ile Gln Ile Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
50                  55                  60

Arg Lys Asn Lys Lys Gln Lys Gln Gln Ala Pro Gln Asn Asn
65                  70                  75                  80

Thr Asn Gln Lys Lys Gln Pro Pro Lys Lys Pro Ala Gln Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
```

```
                165                 170                 175
Lys Phe Thr His Glu Lys Pro Glu Gly Tyr Tyr Asn Trp His His Gly
                    180                 185                 190

Ala Val Gln Tyr Ser Gly Gly Arg Phe Thr Ile Pro Thr Gly Ala Gly
                    195                 200                 205

Lys Pro Gly Asp Ser Gly Arg Pro Ile Phe Asp Asn Lys Gly Arg Val
210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
                260                 265                 270

Asn Thr Thr Phe Pro Cys Ser Gln Pro Cys Thr Pro Cys Cys Tyr
                275                 280                 285

Glu Lys Glu Pro Glu Glu Thr Leu Arg Met Leu Glu Asp Asn Val Met
            290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                    325                 330                 335

Thr Arg Pro Tyr Leu Ala His Cys Pro Asp Cys Gly Glu Gly His Ser
                340                 345                 350

Cys His Ser Pro Val Ala Leu Glu Arg Ile Arg Asn Glu Ala Thr Asp
                355                 360                 365

Gly Thr Leu Lys Ile Gln Val Ser Leu Gln Ile Gly Ile Lys Thr Asp
        370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
                420                 425                 430

Gly Glu Thr Leu Thr Val Gly Phe Thr Asp Ser Arg Lys Ile Ser His
                435                 440                 445

Ser Cys Thr His Pro Phe His His Asp Pro Pro Val Ile Gly Arg Glu
            450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                    485                 490                 495

Pro Pro Asp Thr Pro Asp Arg Thr Leu Met Ser Gln Gln Ser Gly Asn
                500                 505                 510

Val Lys Ile Thr Val Asn Gly Gln Thr Val Arg Tyr Lys Cys Asn Cys
            515                 520                 525

Gly Gly Ser Asn Glu Gly Leu Thr Thr Thr Asp Lys Val Ile Asn Asn
        530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                    565                 570                 575

Lys Gly Lys Ile His Ile Pro Phe Pro Leu Ala Asn Val Thr Cys Arg
                580                 585                 590
```

-continued

```
Val Pro Lys Ala Arg Asn Pro Thr Val Thr Tyr Gly Lys Asn Gln Val
            595                 600                 605
Ile Met Leu Leu Tyr Pro Asp His Pro Thr Leu Leu Ser Tyr Arg Asn
610                 615                 620
Met Gly Glu Glu Pro Asn Tyr Gln Glu Glu Trp Val Met His Lys Lys
625                 630                 635                 640
Glu Val Val Leu Thr Val Pro Thr Glu Gly Leu Glu Val Thr Trp Gly
                645                 650                 655
Asn Asn Glu Pro Tyr Lys Tyr Trp Pro Gln Leu Ser Thr Asn Gly Thr
                    660                 665                 670
Ala His Gly His Pro His Glu Ile Ile Leu Tyr Tyr Glu Leu Tyr
                675                 680                 685
Pro Thr Met Thr Val Val Val Ser Val Ala Thr Phe Ile Leu Leu
690                 695                 700
Ser Met Val Gly Met Ala Ala Gly Met Cys Met Cys Ala Arg Arg Arg
705                 710                 715                 720
Cys Ile Thr Pro Tyr Glu Leu Thr Pro Gly Ala Thr Val Pro Phe Leu
                    725                 730                 735
Leu Ser Leu Ile Cys Cys Ile Arg Thr Ala Lys Ala Ala Thr Tyr Gln
                740                 745                 750
Glu Ala Ala Ile Tyr Leu Trp Asn Glu Gln Gln Pro Leu Phe Trp Leu
            755                 760                 765
Gln Ala Leu Ile Pro Leu Ala Ala Leu Ile Val Leu Cys Asn Cys Leu
770                 775                 780
Arg Leu Leu Pro Cys Cys Cys Lys Thr Leu Ala Phe Leu Ala Val Met
785                 790                 795                 800
Ser Val Gly Ala His Thr Val Ser Ala Tyr Glu His Val Thr Val Ile
                805                 810                 815
Pro Asn Thr Val Gly Val Pro Tyr Lys Thr Leu Val Asn Arg Pro Gly
                820                 825                 830
Tyr Ser Pro Met Val Leu Glu Met Glu Leu Leu Ser Val Thr Leu Glu
            835                 840                 845
Pro Thr Leu Ser Leu Asp Tyr Ile Thr Cys Glu Tyr Lys Thr Val Ile
850                 855                 860
Pro Ser Pro Tyr Val Lys Cys Cys Gly Thr Ala Glu Cys Lys Asp Lys
865                 870                 875                 880
Asn Leu Pro Asp Tyr Ser Cys Arg Val Phe Thr Gly Val Tyr Pro Phe
                885                 890                 895
Met Trp Gly Gly Ala Tyr Cys Phe Cys Asp Ala Glu Asn Thr Gln Leu
                900                 905                 910
Ser Glu Ala His Val Glu Lys Ser Glu Ser Cys Lys Thr Glu Phe Ala
            915                 920                 925
Ser Ala Tyr Arg Ala His Thr Ala Ser Ala Ser Ala Lys Leu Arg Val
930                 935                 940
Leu Tyr Gln Gly Asn Asn Ile Thr Val Thr Ala Tyr Ala Asn Gly Asp
945                 950                 955                 960
His Ala Val Thr Val Lys Asp Ala Lys Phe Ile Val Gly Pro Met Ser
                965                 970                 975
Ser Ala Trp Thr Pro Phe Asp Asn Lys Ile Val Val Tyr Lys Gly Asp
            980                 985                 990
Val Tyr Asn Met Asp Tyr Pro Pro  Phe Gly Ala Gly Arg Pro Gly Gln
            995                 1000                1005
```

```
Phe Gly Asp Ile Gln Ser Arg Thr Pro Glu Ser Lys Asp Val Tyr
    1010                1015                1020

Ala Asn Thr Gln Leu Val Leu Gln Arg Pro Ala Ala Gly Thr Val
    1025                1030                1035

His Val Pro Tyr Ser Gln Ala Pro Ser Gly Phe Lys Tyr Trp Leu
    1040                1045                1050

Lys Glu Arg Gly Ala Ser Leu Gln His Thr Ala Pro Phe Gly Cys
    1055                1060                1065

Gln Ile Ala Thr Asn Pro Val Arg Ala Val Asn Cys Ala Val Gly
    1070                1075                1080

Asn Met Pro Ile Ser Ile Asp Ile Pro Glu Ala Ala Phe Thr Arg
    1085                1090                1095

Val Val Asp Ala Pro Ser Leu Thr Asp Met Ser Cys Glu Val Pro
    1100                1105                1110

Ala Cys Thr His Ser Ser Asp Phe Gly Gly Val Ala Ile Ile Lys
    1115                1120                1125

Tyr Ala Ala Ser Lys Lys Gly Lys Cys Ala Val His Ser Met Thr
    1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245

<210> SEQ ID NO 15
<211> LENGTH: 11234
<212> TYPE: DNA
<213> ORGANISM: Chikungunya virus

<400> SEQUENCE: 15
atggatcctg tgtacgtgga catagacgct gacagcgcct ttttgaaggc cctgcaacgt      60
gcgtacccca tgtttgaggt ggaaccaagg caggtcacac cgaatgacca tgctaatgct     120
agagcgttct cgcatctagc tataaaacta atagagcagg aaattgaccc cgactcaacc     180
atcctggata tcggcagtgc gccagcaagg aggatgatgt cggacaggaa gtaccactgc     240
gtctgcccga tgcgcagtgc ggaagatccc gagagactcg ctaattatgc gagaaagcta     300
gcatctgccg caggaaaagt cctggacaga acatctctg aaagatcgg ggacttacaa      360 gcagtaatgg ccgtgccaga caaggagacg ccaacattct gcttacacac agacgtctca     420
tgtagacaga gagcagacgt cgctatatac caagacgtct atgctgtaca cgcacccacg     480
tcgctatacc accaggcgat taaggggtc cgagtggcgt actgggttgg gttcgacaca     540
accccgttca tgtacaatgc catggcgggt gcctacccct catactcgac aaactgggca     600
gatgagcagt actgaaggc taagaacata ggattatgtt caacagacct gacggaaggt     660
agacgaggca agttgtctat tatgagaggg aaaaagctaa aaccgtgcga ccgtgtgctg     720
```

```
ttctcagtag ggtcaacgct taccccggaa agccgcaagc tacttaagag ctggcacctg    780
ccatcggtgt tccatttaaa gggcaaactc agcttcacat gccgctgtga tacagtggtt    840
tcgtgtgagg gctacgtcgt taagagaata cgatgagcc caggcccttta tggaaaaacc    900 acagggtatg cggtaaccca ccacgcagac ggattcctga tgtgcaagac taccgacacg    960
gttgacggcg aaagagtgtc attctcggtg tgcacatacg tgccggcgac catttgtgat   1020
caaatgaccg gcatccttgc tacagaagtc acgccggagg atgcacagaa gctgttggtg   1080
gggctgaacc agagaatagt ggttaacggc agaacgcaac ggaatatgaa caccatgaaa   1140
aattatctgc ttcccgtggt cgcccaagcc ttcagtaagt gggcaaagga gtgccggaaa   1200
gacatggaag atgaaaaact cctggggtc agagaaagaa cactgacctg ctgctgtcta   1260
tgggcattca agaagcagaa aacacacacg gtctacaaga ggcctgatac ccagtcaatt   1320
cagaaggttc aggccgagtt tgacagcttt gtggtaccga gtctgtggtc gtccgggttg   1380
tcaatccctt tgaggactag aatcaaatgg ttgttaagca aggtgccaaa aaccgacctg   1440
atcccataca gcggagacgc ccgagaagcc cgggacgcag aaaagaagc agaggaagaa   1500 cgagaagcag aactgactcg cgaagcccta ccacctctac aggcagcaca ggaagatgtt   1560
caggtcgaaa tcgacgtgga acagcttgag gacagagcgg gcgcaggaat aatagagact   1620
ccgagaggag ctatcaaagt tactgcccaa ccaacagacc acgtcgtggg agagtacctg   1680
gtactctccc cgcagaccgt actacgtagc cagaagctca gtctgattca cgctttggcg   1740
gagcaagtga agacgtgcac gcacaacgga cgagcaggga ggtatgcggt cgaagcgtac   1800
gacggccgag tcctagtgcc ctcaggctat gcaatctcgc ctgaagactt ccagagtcta   1860
agcgaaagcg caacgatggt gtataacgaa agagagttcg taaacagaaa gctacaccat   1920
attgcgatgc acgaccagc cctgaacacc gacgaagagt cgtatgagct ggtgagggca   1980
gagaggacag aacacgagta cgtctacgac gtggatcaga aagatgctg taagaaggaa   2040 gaagccgcag gactggtact ggtgggcgac ttgactaatc cgccctacca cgaattcgca   2100
tatgaagggc taaaaatccg ccctgcctgc ccatacaaaa ttgcagtcat aggagtcttc   2160
ggagtaccgg gatctggcaa gtcagctatt atcaagaacc tagttaccag gcaggacctg   2220
gtgactagtg gaaagaaaga aaactgccaa gaaatcacca ccgacgtgat gagacagaga   2280
ggtctagaga tatctgcacg tacggttgac tcgctgctct tgaatggatg caacagacca   2340
gtcgacgtgt tgtacgtaga cgaggcgttt gcgtgccact ctggaacgct acttgctttg   2400
atcgccttgg tgagaccaag gcagaaagtt gtactttgtg gtgacccgaa gcagtgcggc   2460
ttcttcaata tgatgcagat gaaagtcaac tacaatcaca acatctgcac ccaagtgtac   2520
cacaaaagta tctccaggcg tgtgtacactg cctgtgaccg ccattgtgtc atcgttgcat   2580
tacgaaggca aaatgcgcac tacgaatgag tacaacaagc cgattgtagt ggacactaca   2640
ggctcaacaa aacctgaccc tggagacctc gtgttaacgt gcttcagagg gtgggttaaa   2700
caactgcaaa ttgactatcg tggatacgag gtcatgacag cagccgcatc ccaagggtta   2760
accagaaaag gagtttacgc agttagacaa aaagttaatg aaaacccgct ctatgcatca   2820
acgtcagagc acgtcaacgt actcctaacg cgtacggaag gtaaactggt atggaagaca   2880
ctttccggcg acccgtggat aaagacgctg cagaacccac cgaaaggaaa cttcaaagca   2940
actattaagg agtgggaggt ggagcatgca tcaataatgg cgggcatctg cagtcaccaa   3000
atgaccttcg atacattcca aaataaagcc aacgtttgtt gggctaagag cttggtccct   3060
```

```
atcctcgaaa cagcggggat aaaactaaat gataggcagt ggtctcagat aattcaagcc    3120
ttcaaagaag acaaagcata ctcacctgaa gtagccctga atgaaatatg tacgcgcatg    3180
tatggggtgg atctagacag cgggctattt tctaaaccgt tggtgtctgt gtattacgcg    3240
gataaccact gggataatag gcctggaggg aaaatgttcg gatttaaccc cgaggcagca    3300
tccattctag aaagaaagta tccattcaca aaagggaagt ggaacatcaa caagcagatc    3360
tgcgtgacta ccaggaggat agaagacttt aaccctacca ccaacatcat accggccaac    3420
aggagactac cacactcatt agtggccgaa caccgcccag taaaaggggga aagaatggaa    3480 tggctggtta acaagataaa cggccaccac gtgctcctgg tcagtggcta taaccttgca    3540
ctgcctacta agagagtcac ttgggtagcg ccgttaggtg tccgcggagc ggactacaca    3600
tacaacctag agttgggtct gccagcaacg cttggtaggt atgaccttgt ggtcataaac    3660
atccacacac ctttttcgcat acaccattac caacagtgcg tcgaccacgc aatgaaactg    3720
caaatgctcg ggggtgactc attgagactg ctcaaaccgg gcggctctct attgatcaga    3780
gcatatggtt acgcagatag aaccagtgaa cgagtcatct gcgtattggg acgcaagttt    3840
agatcgtcta gagcgttgaa accaccatgt gtcaccagca acactgagat gttttttccta    3900 ttcagcaact ttgacaatgg cagaaggaat ttcacaactc atgtcatgaa caatcaactg    3960
aatgcagcct tcgtaggaca ggtcacccga gcaggatgtg caccgtcgta ccgggtaaaa    4020
cgcatggaca tcgcgaagaa cgatgaagag tgcgtagtca acgccgctaa ccctcgcggg    4080
ttaccgggtg acggtgtttg caaggcagta tacaaaaaat ggccggagtc ctttaagaac    4140
agtgcaacac cagtgggaac cgcaaaaaca gttatgtgcg gtacgtatcc agtaatccac    4200
gctgttggac caaacttctc taattattcg gagtctgaag gggaccggga attggcagct    4260
gcctatcgaa agtcgcaaaa ggaagtaact aggctgggag taaatagtgt agctatacct    4320
ctcctctcca caggtgtata tcaggaggg aaagacaggc tgacccagtc actgaaccac    4380
ctctttacag ccatggactc gacgatgca gacgtggtca tctactgccg cgacaaagaa    4440
tgggagaaga aatatctga ggccatacag atgcggaccc aagtagagct gctggatgag    4500
cacatctcca tagactgcga tattgttcgc gtgcaccctg acagcagctt ggcaggcaga    4560
aaaggataca gcaccacgga aggcgcactg tactcatatc tagaagggac ccgttttcat    4620
cagacggctg tggatatggc ggagatacat actatgtggc caaagcaaac agaggccaat    4680
gagcaagtct gcctatatgc cctgggggaa agtattgaat cgatcaggca gaaatgcccg    4740
gtggatgatg cagacgcatc atctcccccc aaaactgtcc cgtgcctttg ccgttacgct    4800
atgactccag aacgcgtcac ccggcttcgc atgaaccacg tcacaagcat aattgtgtgt    4860
tcttcgtttc ccctcccaaa gtacaaaata gaaggagtgc aaaaagtcaa atgctctaag    4920
gtaatgctat ttgaccacaa cgtgccatcg cgcgtaagtc aagggaata tagatcttcc    4980 caggagtctg cacaggaggc gagtacaatc acgtcactga cgcatagtca attcgaccta    5040
agcgttgatg gcgagatact gcccgtcccg tcagacctgg atgctgacgc cccagccta    5100 gaaccagcac tagacgacgg ggcgacacac acgctgccat ccacaaccgg aaaccttgcg    5160
gccgtgtctg actgggtaat gagcaccgta cctgtcgcgc cgcccagaag aaggcgaggg    5220
agaaacctga ctgtgacatg tgacgagaga gaagggaata taacacccat ggctagcgtc    5280
cgattcttta gggcagagct gtgtccggtc gtacaagaaa cagcggagac gcgtgacaca    5340
gcaatgtctc ttcaggcacc accgaatacc gccacggaac cgaatcatcc gccgatctcc    5400
ttcggagcat caagcgagac gttccccatt acatttgggg acttcaacga aggagaaatc    5460
```

```
gaaagcttgt cttctgagct actaactttc ggagacttct taccaggaga agtggatgac    5520
ttgacagaca gcgactggtc cacgtgctca gacacggacg acgagttatg actagacagg    5580
gcaggtgggt atatattctc gtcggacacc ggtccaggtc atttacaaca gaagtcagta    5640
cgccagtcag tgctgccggt gaacaccctg gaggaagtcc acgaggagaa gtgttaccca    5700
cctaagctgg atgaagcaaa ggagcaacta ttacttaaga aactccagga gagtgcatcc    5760
atggccaaca gaagcaggta tcagtcgcgc aaagtagaaa atatgaaagc agcaatcatc    5820
cagagactaa agagaggctg tagactatac ttaatgtcag agaccccaaa agtccctact    5880
taccggacta catatccggc gcctgtgtac tcgcctccga tcaacgtccg attgtccaat    5940
cccgagtccg cagtggcagc atgcaatgag ttcttagcta gaaactatcc aactgtctca    6000
tcataccaaa ttaccgacga gtatgatgca tatctagaca tggtggacgg gtcggagagt    6060
tgcctggacc gagcgacatt caatccgtca aaactcagga gctacccgaa acagcacgct    6120
taccacgcgc cctccatcag aagcgctgta ccgtccccat tccagaacac actacagaat    6180
gtactggcag cagccacgaa aagaaactgc aacgtcacac agatgaggga attacccact    6240
ttggactccg cagtattcaa cgtggagtgt ttcaaaaaat tcgcatgcaa ccaagaatac    6300
tgggaagaat tgctgccagc cctattagg ataacaactg agaatttagc aacctatgtt    6360
actaaactaa aagggccaaa agcagcagcg ctattcgcaa aaacccataa tctactgcca    6420
ctacaggaag taccaatgga taggttcaca gtagatatga aagggacgt gaaggtgact    6480
cctggtacaa agcatacaga ggaaagacct aaggtgcagg ttatacaggc ggctgaaccc    6540
ttggcgacag catacctatg tgggattcac agagagctgg ttaggaggct gaacgccgtc    6600
ctcctaccca atgtacatac actatttgac atgtctgccg aggatttcga tgccatcata    6660
gccgcacact ttaagccagg agacactgtt ttggaaacgg acatagcctc ctttgataag    6720
agccaagatg attcacttgc gcttactgct ttgatgctgt tagaggattt aggggtggat    6780
cactccctgc tggacttgat agaggctgct ttcggagaga tttccagctg tcacctaccg    6840
acaggtacgc gcttcaagtt cggcgccatg atgaaatcag gtatgttcct aactctgttc    6900
gtcaacacat tgttaaacat caccatcgcc agccgagtgc tggaagatcg tctgacaaaa    6960
tccgcgtgcg cggccttcat cggcgacgac aacataatac atggagtcgt ctccgatgaa    7020
ttgatggcag ccagatgtgc cacttggatg aacatggaag tgaagatcat agatgcagtt    7080
gtatccttga agcccctta cttttgtgga gggtttatac tgcacgatac tgtgacagga    7140
acagcttgca gagtggcaga cccgctaaaa aggctttta aactgggcaa accgctagcg    7200
gcaggtgacg aacaagatga agatagaaga cgagcgctgg ctgacgaagt gatcagatgg    7260
caacgaacag ggctaattga tgagctggag aaagcgtat actctaggta cgaagtgcag    7320
ggtatatcag ttgtggtaat gtccatggcc acctttgcaa gctccagatc caacttcgag    7380
aagctcagag gacccgtcat aactttgtac ggcggtccta ataggtatg cactacagct    7440
acctattttg cagaagccga cagcaagtat ctaaacacta atcagctaca atggagttca    7500
tcccaaccca aacttttttac aataggaggt accagcctcg accctggact ccgcgctcta    7560
ctatccaaat cattaggccc agaccgcgcc ctcagaggca gctgggcaa cttgcccagc    7620
tgatctcagc agttaataaa ctgacaatgc gcgcggtacc ccaacagaag ccacgcagga    7680
atcggaagaa taagaagcaa aagcaaaaac aacaggcgcc acaaacaac acaaatcaaa    7740
agaagcagcc acctaaaaag aaaccggctc aaaagaaaaa gaagccgggc cgcagagaga    7800
```

```
ggatgtgcat gaaaatcgaa aatgattgta ttttcgaagt caagcacgaa ggtaaggtaa    7860
caggttacgc gtgcctggtg ggggacaaag taatgaaacc agcacacgta aaggggacca    7920
tcgataacgc ggacctggcc aaactggcct ttaagcggtc atctaagtat gaccttgaat    7980
gcgcgcagat acccgtgcac atgaagtccg acgcttcgaa gttcacccat gagaaaccgg    8040
aggggtacta caactggcac cacggagcag tacagtactc aggaggccgg ttcaccatcc    8100
ctacaggtgc tggcaaacca ggggacagcg gcagaccgat cttcgacaac aagggacgcg    8160
tggtggccat agtcttagga ggagctaatg aaggagcccg tacagccctc tcggtggtga    8220
cctggaataa agacattgtc actaaaatca cccccgaggg ggccgaagag tggagtcttg    8280
ccatcccagt tatgtgcctg ctggcaaaca ccacgttccc ctgctcccag cccccttgca    8340
cgccctgctg ctacgaaaag gaaccggagg aaacccctacg catgcttgag acaacgtca    8400
```

```
tctgcgacgc tgaaaacacg cagttgagcg aagcacatgt ggagaagtcc gaatcatgca   10260
aaacagaatt tgcatcagca tacagggctc ataccgcatc tgcatcagct aagctccgcg   10320
tcctttacca aggaaataac atcactgtaa ctgcctatgc aaacggcgac catgccgtca   10380
cagttaagga cgccaaattc attgtggggc aatgtcttc agcctggaca cctttcgaca    10440
acaaaattgt ggtgtacaaa ggtgacgtct ataacatgga ctacccgccc tttggcgcag   10500
gaagaccagg acaatttggc gatatccaaa gtcgcacacc tgagagtgaa gacgtctatg   10560
ctaatacaca actggtactg cagagaccgg ctgcgggtac ggtacacgtg ccatactctc   10620
aggcaccatc tggctttaag tattggctaa agaacgcgg ggcgtcactg cagcacacag    10680
caccatttgg ctgccaaata gcaacaaacc cggtaagagc ggtgaactgc gccgtaggga   10740
acatgcccat ctccatcgac ataccggaag cggccttcac tagggtcgtc gacgcgccct   10800
ctttaacgga catgtcgtgc gaggtaccag cctgcaccca ttcctcagac tttggggggcg  10860 tcgccattat taaatatgca gccagcaaga aaggcaagtg tgcggtgcat tcgatgacta   10920
acgccgtcac tattcgggaa gctgagatag aagttgaagg gaattctcag ctgcaaatct   10980
ctttctcgac ggccttagcc agcgccgaat tccgcgtaca agtctgttct acacaagtac   11040
actgtgcagc tgagtgccac cccccgaagg accacatagt caactacccg cgtcacata    11100 ccaccctcgg ggtccaggac atctccgcta cggcgatgtc atgggtgcag aagatcacgg   11160
gaggtgtggg actggttgtt gctgttgccg cactgattct aatcgtggtg ctatgcgtgt   11220
cgttcagcag gcac                                                    11234

<210> SEQ ID NO 16
<211> LENGTH: 11234
<212> TYPE: DNA
<213> ORGANISM: Chikungunya virus

<400> SEQUENCE: 16
atggatcctg tgtacgtgga catagacgct gacagcgcct ttttgaaggc cctgcaacgt      60
gcgtacccca tgtttgaggt ggaaccaagg caggtcacac cgaatgacca tgctaatgct     120
agagcgttct cgcatctagc tataaaacta atagagcagg aaattgaccc cgactcaacc     180
atcctggata tcggcagtgc gccagcaagg aggatgatgt cggacaggaa gtaccactgc    240
gtctgcccga tgcgcagtgc ggaagatccc gagagactcg ctaattatgc gagaaagcta    300
gcatctgccg caggaaaagt cctggacaga acatctctg gaaagatcgg ggacttacaa     360
gcagtaatgg ccgtgccaga caaggagacg ccaacattct gcttacacac agacgtctca    420
tgtagacaga gagcagacgt cgctatatac caagacgtct atgctgtaca cgcacccacg   480
tcgctatacc accaggcgat taagggggtc cgagtggcgt actgggttgg gttcgacaca    540
accccgttca tgtacaatgc catggcgggt gcctacccct atactcgac aaactgggca    600 gatgagcagg tactgaaggc taagaacata ggattatgtt caacagacct gacggaaggt    660
agacgaggca agttgtctat tatgagaggg aaaaagctaa accgtgcga ccgtgtgctg    720 ttctcagtag ggtcaacgct ttacccggaa agccgcaagc tacttaagag ctggcacctg   780
ccatcggtgt tccatttaaa gggcaaactc agcttcacat gccgctgtga tacagtggtt    840
tcgtgtgagg gctacgtcgt taagagaata acgatgagcc caggcctta tggaaaaacc    900 acagggtatg cggtaaccca ccacgcagac ggattcctga tgtgcaagac tactgacacg    960
gttgacggcg aaagagtgtc attctcggtg tgcacatacg tgccggcgac catttgtgat   1020
```

```
caaatgaccg gcatccttgc tacagaagtt acgccggagg atgcacagaa gctgttggtg    1080
gggctgaacc agagaatagt ggttaacggc agaacgcaac ggaatatgaa caccatgaaa    1140
aattatctgc ttcccgtggt cgcccaagcc ttcagtaagt gggcaaagga gtgccggaaa    1200
gacatggaag atgaaaaact cctgggggtc agagaaagaa cactgacctg ctgctgtcta    1260
tgggcattca agaagcagaa aacacacacg gtctacaaga ggcctgatac ccagtcaatt    1320
cagaaggttc aggccgagtt tgacagcttt gtggtaccga gtctgtggtc gtccgggttg    1380
tcaatccctt tgaggactag aatcaaatgg ttgttaagca aggtgccaaa aaccgacctg    1440
atcccataca gcggagacgc ccgagaagcc cgggacgcag aaaaagaagc agaggaagaa    1500
cgagaagcag aactgactcg cgaagcccta ccacctctac aggcagcaca ggaagatgtt    1560
caggtcgaaa tcgacgtgga acagcttgag gacagagcgg cgcaggaat aatagagact     1620 ccgagaggag ctatcaaagt tactgcccaa ccaacagacc acgtcgtggg agagtacctg    1680
gtactctccc cgcagaccgt actacgtagc cagaagctca gtctgattca cgctttggcg    1740
gagcaagtga agacgtgcac gcacaacgga cgagcaggga ggtatgcggt cgaagcgtac    1800
gacggccgag tcctagtgcc ctcaggctat gcaatctcgc ctgaagactt ccagagtcta    1860
agcgaaagcg caacgatggt gtataacgaa agagagttcg taaacagaaa gctacaccat    1920
attgcgatgc acggaccagc cctgaacacc gacgaagagt cgtatgagct ggtgagggca    1980
gagaggacag aacacgagta cgtctacgac gtggatcaga agatgctg taagaaggaa      2040 gaagccgcag gactggtact ggtgggcgac ttgactaatc cgccctacca cgaattcgca    2100
tatgaagggc taaaaatccg ccctgcctgc ccatacaaaa ttgcagtcat aggagtcttc    2160
ggagtaccgg gatctggcaa gtcagctatt atcaagaacc tagttaccag gcaggacctg    2220
gtgactagtg gaaagaaaga aaactgccaa gaaatcacca ccgacgtgat gagacagaga    2280
ggtctagaga tatctgcacg tacggttgac tcgctgctct tgaatggatg caacagacca    2340
gtcgacgtgt tgtacgtaga cgaggcgttt gcgtgccact ctggaacgct acttgctttg    2400
atcgccttgg tgagaccaag gcagaaagtt gtactttgtg gtgacccgaa gcagtgcggc    2460
ttcttcaata tgatgcagat gaaagtcaac tacaatcaca acatctgcac ccaagtgtac    2520
cacaaaagta tctccaggcg cgtgtacactg cctgtgaccg ccattgtgtc atcgttgcat    2580
tacgaaggca aaatgcgcac tacgaatgag tacaacaagc cgattgtagt ggacactaca    2640
ggctcaacaa aacctgaccc tggagacctc gtgttaacgt gcttcagagg gtgggttaaa    2700
caactgcaaa ttgactatcg tggatacgag gtcatgacag cagccgcatc ccaagggtta    2760
accagaaaag gagtttacgc agttagacaa aaagttaatg aaaacccgct ctatgcatca    2820
acgtcagagc acgtcaacgt actcctaacg cgtacggaag gtaaactggt atggaagaca    2880
ctttccggcg acccgtggat aaagacgctg cagaacccac cgaaaggaaa cttcaaagca    2940
actattaagg agtgggaggt ggagcatgca tcaataatgg cgggcatctg cagtcaccaa    3000
atgaccttcg atacattcca aaataaagcc aacgtttgtt gggctaagag cttggtccct    3060
atcctcgaaa cagcggggat aaaactaaat gataggcagt ggtctcagat aattcaagcc    3120
ttcaaagaag acaaagcata ctcacctgaa gtagccctga atgaaatatg tacgcgcatg    3180 tatgggtgg atctagacag cgggctattt tctaaaccgt tggtgtctgt gtattacgcg     3240
gataaccact gggataatag gcctggaggg aaaatgttcg gatttaaccc cgaggcagca    3300
tccattctag aaagaaagta tccattcaca aaagggaagt ggaacatcaa caagcagatc    3360
tgcgtgacta ccaggaggat agaagacttt aaccctacca ccaacatcat accggccaac    3420
```

```
aggagactac cacactcatt agtggccgaa caccgcccag taaaagggga aagaatggaa    3480
tggctggtta acaagataaa cggccaccac gtgctcctgg tcagtggcta taaccttgca    3540
ctgcctacta agagagtcac ttgggtagcg ccgttaggtg tccgcggagc ggactacaca    3600
tacaacctag agttgggtct gccagcaacg cttggtaggt atgaccttgt ggtcataaac    3660
atccacacac cttttcgcat acaccattac aacagtgcg tcgaccacgc aatgaaactg    3720
caaatgctcg ggggtgactc attgagactg ctcaaaccgg gcggctctct attgatcaga    3780
gcatatggtt acgcagatag aaccagtgaa cgagtcatct gcgtattggg acgcaagttt    3840
agatcgtcta gagcgttgaa accaccatgt gtcaccagca acactgagat gttttcctca    3900
ttcagcaact ttgacaatgg cagaaggaat ttcacaactc atgtcatgaa caatcaactg    3960
aatgcagcct tcgtaggaca ggtcacccga gcaggatgtg caccgtcgta ccgggtaaaa    4020
cgcatggaca tcgcgaagaa cgatgaagag tgcgtagtca acgccgctaa ccctcgcggg    4080
ttaccgggtg acggtgtttg caaggcagta tacaaaaaat ggccggagtc ctttaagaac    4140
agtgcaacac cagtgggaac cgcaaaaaca gttatgtgcg gtacgtatcc agtaatccac    4200
gctgttggac caaacttctc taattattcg gagtctgaag gggaccggga attggcagct    4260
gcctatcgag aagtcgcaaa ggaagtaacc aggctgggag taaatagtgt agctatacct    4320
ctcctctcca caggtgtata ctcaggaggg aaagacaggc tgacccagtc actgaaccac    4380
ctctttacag ccatggactc gacggatgca gacgtggtca tctactgccg cgacaaagaa    4440
tgggagaaga aaatatctga ggccatacag atgcggaccc aagtagagct gctggatgag    4500
cacatctcca tagactgcga tattgttcgc gtgcaccctg acagcagctt ggcaggcaga    4560
aaaggataca gcaccacgga aggcgcactg tactcatatc tagaagggac ccgttttcat    4620
cagacggctg tggatatggc ggagatacat actatgtggc caaagcaaac agaggccaat    4680
gagcaagcct gcctatatgc cctggggaa agtattgaat cgatcaggca gaaatgcccg    4740
gtggatgatg cagacgcatc atctcccccc aaaactgtcc cgtgcctttg ccgttacgct    4800
atgactccag aacgcgtcac ccggcttcgc atgaaccacg tcacaagcat aattgtgtgt    4860
tcttcgtttc ccctcccaaa gtacaaaata gaaggagtgc aaaaagtcaa atgctctaag    4920
gtaatgctat ttgaccacaa cgtgccatcg cgcgtaagtc aagggaata tagatcttcc    4980
caggagtctg cacaggaggc gagtacaatc acgtcactga cgcatagtca attcgaccta    5040
agcgttgatg gcgagatact gcccgtcccg tcagacctgg atgctgacgc cccagcccta    5100
gaaccagcac tagacgacgg ggcgacacac acgctgccat ccacaaccgg aaaccttgcg    5160
gccgtgtctg actgggtaat gagcaccgta cctgtcgcgc cgcccagaag aaggcgaggg    5220
agaaacctga ctgtgacatg tgacgagaga aagggaata taacacccat ggctagcgtc    5280
cgattcttta gggcagagct gtgtccggtc gtacaagaaa cagcggagac gcgtgacaca    5340
gcaatgtctc ttcaggcacc accgagtacc gccacggaac cgaatcatcc gccgatctcc    5400
ttcggagcat caagcgagac gttccccatt acatttgggg acttcaacga aggagaaatc    5460
gaaagcttgt cttctgagct actaactttc ggagacttct taccaggaga agtggatgac    5520
ttgacagaca gcgactggtc cacgtgctca gacacgacg acgagttatg actagacagg    5580
gcaggtgggt atatattctc gtcggacacc ggtccaggtc atttacaaca gaagtcagta    5640
cgccagtcag tgctgccggt gaacacctg gaggaagtcc acgaggagaa gtgttaccca    5700
cctaagctgg atgaagcaaa ggagcaacta ttacttaaga aactccagga gagtgcatcc    5760
```

```
atggccaaca gaagcaggta tcagtcgcgc aaagtagaaa acatgaaagc agcaatcatc    5820
cagagactaa agagaggctg tagactatac ttaatgtcag agaccccaaa agtccctact    5880
taccggacta tatatccggc gcctgtgtac tcgcctccga tcaacgtccg attgtccaat    5940
cccgagtccg cagtggcagc atgcaatgag ttcttagcta gaaactatcc aactgtctca    6000
tcataccaaa ttaccgacga gtatgatgca tatctagaca tggtggacgg gtcggagagt    6060
tgcctggacc gagcgacatt caatccgtca aaactcagga gctacccgaa acagcacgct    6120
taccacgcgc cctccatcag aagcgctgta ccgtccccat tccagaacac actacagaat    6180
gtactggcag cagccacgaa aagaaactgc aacgtcacac agatgaggga attacccact    6240
ttggactccg cagtattcaa cgtggagtgt ttcaaaaaat tcgcatgcaa ccaagaatac    6300
tgggaagaat ttgctgccag ccctattagg ataacaactg agaatttagc aacttatgtt    6360
actaaactaa aagggccaaa agcagcagcg ctattcgcaa aaacccataa tctactgcca    6420
ctacaggaag taccaatgga taggttcaca gtagatatga aagggacgt gaaggtgact    6480 cctggtacaa agcatacaga ggaaagacct aaggtgcagg ttatacaggc ggctgaaccc    6540
ttggcgacag catacctatg tgggattcac agagagctgg ttaggaggct gaacgctgtc    6600
ctcctaccca atgtacatac actatttgac atgtctgccg aggatttcga tgccatcata    6660
gccgcacact ttaagccagg agacactgtt ttggaaacgg acatagcctc ctttgataag    6720
agccaagatg attcacttgc gcttactgct ttgatgctgt tagaggattt aggggtggat    6780
cactccctgc tggacttgat agaggctgct ttcggagaga tttccagctg tcacctaccg    6840
acaggtacgc gcttcaagtt cggcgccatg atgaaatcag gtatgttcct aactctgttc    6900
gtcaacacat tgttaaacat caccatcgcc agccgagtgc tggaagatcg tctgacaaaa    6960
tccgcgtgcg cggccttcat cggcgacgat aacataatac atggagtcgt ctccgatgaa    7020
ttgatggcag ccagatgtgc cacttggatg aacatggaag tgaagatcat agatgcagtt    7080
gtatctttga aagcccctta cttttgtgga gggtttatac tgcacgatac tgtgacagga    7140
acagcttgca gagtggcaga cccgctaaaa aggctttttta aactgggcaa accgctagcg    7200
gcaggtgacg aacaagatga agatagaaga cgagcgctgg ctgacgaagt gatcagatgg    7260
caacgaacag ggctaattga tgagctggag aaagcggtat actctaggta cgaagtgcag    7320
ggtatatcag ttgtggtaat gtccatggcc acctttgcaa gctccagatc caacttcgag    7380
aagctcagag acccgtcat aactttgtac ggcggtccta ataggtacg cactacagct    7440 acctattttg cagaagccga cagcaagtat ctaaacacta atcagctaca atggagttca    7500
tcccaaccca aactttttac aataggaggt accagcctcg accctggact ccgcgctcta    7560
ctatccaaat cattaggccc agaccgcgcc tcagaggca agctgggcaa cttgcccagc    7620
tgatctcagc agttaataaa ctgacaatgc gcgcggtacc ccaacagaag ccacgcagga    7680
atcggaagaa taagaagcaa aagcaaaaac aacaggcgcc acaaacaac acaaatcaaa    7740 agaagcagcc acctaaaaag aaaccggctc aaaagaaaaa gaagccgggc cgcagagaga    7800
ggatgtgcat gaaaatcgaa aatgattgta ttttcgaagt caagcacgaa ggtaaggtaa    7860
caggttacgc gtgcctggtg ggggacaaag taatgaaacc agcacacgta aaggggacca    7920
tcgataacgc ggacctggcc aaactggcct ttaagcggtc atctaagtat gaccttgaat    7980
gcgcgcagat acccgtgcac atgaagtccg acgcttcgaa gttcacccat gagaaaccgg    8040
aggggtacta caactggcac cacggagcag tacagtactc aggaggccgg ttcaccatcc    8100
ctacaggtgc tggcaaacca ggggacagcg gcagaccgat cttcgacaac aagggacgcg    8160
```

```
tggtggccat agtcttagga ggagctaatg aaggagcccg tacagccctc tcggtggtga    8220
cctggaataa agacattgtc actaaaatca cccccgaggg ggccgaagag tggagtcttg    8280
ccatcccagt tatgtgcctg ctggcaaaca ccacgttccc ctgctcccag cccccttgca    8340
cgccctgctg ctacgaaaag gaaccggagg aaacccacg catgcttgag aacaacgtca    8400
tgagaccagg gtactatcag ctgctacagg catccttaac atgttctccc caccgccagc    8460
gacgcagcac caaggacaac ttcaatgtct ataaagccac aagaccatac ttagctcact    8520
gtcccgactg tggagaaggg cactcgtgcc atagtcccgt agcactagaa cgcatcagaa    8580
atgaagcgac agacgggacg ctgaaaatcc aggtctcctt gcaaatcgga ataaagacgg    8640
atgacagcca cgattggacc aagctgcgtt atatggacaa ccacatgcca gcagacgcag    8700
agagggcggg gctatttgta agaacatcag caccgtgtac gattactgga caatgggac    8760 acttcatcct ggcccgatgt ccaaaagggg aaactctgac ggtgggattc actgacagta    8820
ggaagattag tcattcatgt acgcacccat ttcaccacga ccctcctgtg ataggtcggg    8880
aaaaattcca ttcccgaccg cagcacggta aagagctacc ttgcagcacg tacgtgcaga    8940
gcaccgccgc aactaccgag gagatagagg tacacatgcc cccagacacc cctgatcgca    9000
cattaatgtc acaacagtcc ggcaacgtaa agatcacagt caatggccag acggtgcggt    9060
acaagtgtaa ttgcggtggc tcaaatgaag gactaacaac tacagacaaa gtgattaata    9120
actgcaaggt tgatcaatgt catgccgcgg tcaccaatca caaaaagtgg cagtataact    9180
cccctctggt cccgcgtaat gctgaacttg gggaccgaaa aggaaaaatt cacatcccgt    9240
ttccgctggc aaatgcaaca tgcagggtgc ctaaagcaag gaaccccacc gtgacgtacg    9300
ggaaaaacca agtcatcatg ctactgtatc ctgaccaccc aacactcctg tcctaccgga    9360
atatgggaga agaaccaaac tatcaagaag agtgggtgat gcataagaag gaagtcgtgc    9420
taaccgtgcc gactgaaggg ctcgaggtca cgtggggcaa caacgagccg tataagtatt    9480
ggccgcagtt atctacaaac ggtacagccc atggccaccc gcatgagata attctgtatt    9540
attatgagct gtaccctact atgactgtag tagttgtgtc agtggccacg ttcatactcc    9600
tgtcgatggt gggtatggca gcggggatgt gcatgtgtgc acgacgcaga tgcatcacac    9660
cgtatgaact gacaccagga gctaccgtcc ctttcctgct tagcctaata tgctgcatca    9720
gaacagctaa agcggccaca taccaagagg ctgcgatata cctgtggaac gagcagcaac    9780
ctttgttttg gctacaagcc cttattccgc tggcagccct gattgttcta tgcaactgtc    9840
tgagactctt accatgctgc tgtaaaacgc tggcttttt agccgtaatg agcgtcggtg    9900
cccacactgt gagcgcgtac gaacacgtaa cagtgatccc gaacacggtg ggagtaccgt    9960
ataagactct agtcaataga cctggctaca gccccatggt attggagatg gaactactgt    10020
cagtcacttt ggagccaaca ctatcgcttg attacatcac gtgcgagtac aaaaccgtca    10080
tcccgtctcc gtacgtgaag tgctgcggta cagcagagtg caaggacaaa aacctacctg    10140
actacagctg taaggtcttc accggcgtct acccatttat gtgggcggc gcctactgct    10200 tctgcgacgc tgaaaacacg cagttgagcg aagcacatgt ggagaagtcc gaatcatgca    10260
aaacagaatt tgcatcagca tacagggctc ataccgcatc tgcatcagct aagctccgcg    10320
tcctttacca aggaaataac atcactgtaa ctgcctatgc aaacggcgac catgccgtca    10380
cagttaagga cgccaaattc attgtggggc caatgtcttc agcctggaca cctttcgaca    10440
acaaaattgt ggtgtacaaa ggtgacgtct ataacatgga ctacccgccc tttggcgcac    10500
```

-continued

| | |
|---|---|
| gaagaccagg acaatttggc gatatccaaa gtcgcacacc tgagagtgaa gacgtctatg | 10560 |
| ctaatacaca actggtactg cagagaccgg ctgcgggtac ggtacacgtg ccatactctc | 10620 |
| aggcaccatc tggcttttaag tattggctaa agaacgcgg ggcgtcactg cagcacacag | 10680 |
| caccatttgg ctgccaaata gcaacaaacc cggtaagagc ggtgaactgc gccgtaggga | 10740 |
| acatgcccat ctccatcgac ataccggaag cggccttcac tagggtcgtc gacgcgccct | 10800 |
| ctttaacgga catgtcgtgc gaggtaccag cctgcaccca ttcctcagac tttggggggcg | 10860 |
| tcgccattat taaatatgca gccagcaaga aaggcaagtg tgcggtgcat tcgatgacta | 10920 |
| acgccgtcac tattcgggaa gctgagatag aagttgaagg gaattctcag ctgcaaatct | 10980 |
| ctttctcgac ggccttagcc agcgccgaat tccgcgtaca agtctgttct acacaagtac | 11040 |
| actgtgcagc tgagtgccac cccccgaagg accacatagt caactacccg gcgtcacata | 11100 |
| ccaccctcgg ggtccaggac atctccgcta cggcgatgtc atgggtgcag aagatcacgg | 11160 |
| gaggtgtggg actggttgtt gctgttgccg cactgattct aatcgtggtg ctatgcgtgt | 11220 |
| cgttcagcag gcac | 11234 |

<210> SEQ ID NO 17
<211> LENGTH: 11234
<212> TYPE: DNA
<213> ORGANISM: Chikungunya virus

<400> SEQUENCE: 17

| | |
|---|---|
| atggatcctg tgtacgtgga catagacgct gacagcgcct ttttgaaggc cctgcaacgt | 60 |
| gcgtacccca tgtttgaggt ggaaccaagg caggtcacac cgaatgacca tgctaatgct | 120 |
| agagcgttct cgcatctagc tataaaacta atagagcagg aaattgaccc cgactcaacc | 180 |
| atcctggata tcggcagtgc gccagcaagg aggatgatgt cggacaggaa gtaccactgc | 240 |
| gtctgcccga tgcgcagtgc ggaagatccc gagagactcg ctaattatgc gagaaagcta | 300 |
| gcatctgccg caggaaaagt cctggacaga aacatctctg aaagatcgg ggacttacaa | 360 |
| gcagtaatgg ccgtgccaga caaggagacg ccaacattct gcttacacac agacgtctca | 420 |
| tgtagacaga gagcagacgt cgctatatac caagacgtct atgctgtaca cgcacccacg | 480 |
| tcgctatacc accaggcgat taaaggggtc cgagtggcgt actgggttgg gttcgacaca | 540 |
| accccgttca tgtacaatgc catggcgggt gcctaccccct catactcgac aaactgggca | 600 |
| gatgagcagg tactgaaggc taagaacata ggattatgtt caacagacct gacggaaggt | 660 |
| agacgaggca gttgtctat tatgagaggg aaaaagctaa accgtgcga ccgtgtgctg | 720 |
| ttctcagtag ggtcaacgct ttacccggaa agccgcaagc tacttaagag ctggcacctg | 780 |
| ccatcggtgt tccatttaaa gggcaaactc agcttacat gccgctgtga tacagtggtt | 840 |
| tcgtgtgagg gctacgtcgt taagagaata acgatgagcc caggcctta tggaaaaacc | 900 |
| acagggtatg cggtaaccca ccacgcgac ggattcctga tgtgcaagac taccgacacg | 960 |
| gttgacggcg aaagagtgtc attctcggtg tgcacatacg tgccggcgac catttgtgat | 1020 |
| caaatgaccg gcatccttgc tacagaagtc acgccggagg atgcacagaa gctgttggtg | 1080 |
| gggctgaacc agagaatagt ggttaacggc agaacgcaac ggaatacgaa caccatgaaa | 1140 |
| aattatctgc ttcccgtggt cgcccaagcc ttcagtaagt gggcaaagga gtgccggaaa | 1200 |
| gacatggaag atgaaaaact cctgggggtc agagaaagaa cactgacctg ctgctgtcta | 1260 |
| tgggcattca gaagcagaa aacacacacg gtctacaaga ggcctgatac ccagtcaatt | 1320 |
| cagaaggttc aggccgagtt tgacagcttt gtggtaccga gtctgtggtc gtccgggttg | 1380 |

```
tcaatccctt tgaggactag aatcaaatgg ttgttaagca aggtgccaaa aaccgacctg    1440
atcccataca gcggagacgc ccgagaagcc cgggacgcag aaaaagaagc agaggaagaa    1500
cgagaagcag aactgactcg cgaagcccta ccacctctac aggcagcaca ggaagatgtt    1560
caggtcgaaa tcgacgtgga acagcttgag gacagagcgg gcgcaggaat aatagagact    1620
ccgagaggag ctatcaaagt tactgcccaa ccaacagacc acgtcgtggg agagtacctg    1680
gtactctccc cgcagaccgt actacgtagc cagaagctca gtctgattca cgctttggcg    1740
gagcaagtga agacgtgcac gcacaacgga cgagcaggga ggtatgcggt cgaagcgtac    1800
gacggccgag tcctagtgcc ctcaggctat gcaatctcgc ctgaagactt ccagagtcta    1860
agcgaaagcg caacgatggt gtataacgaa agagagttcg taaacagaaa gctacaccat    1920
attgcgatgc acggaccagc cctgaacacc gacgaagagt cgtatgagct ggtgagggca    1980
gagaggacag aacacgagta cgtctacgac gtggatcaga aagatgctg taagaaggaa    2040 gaagccgcag gactggtact ggtgggcgac ttgactaatc cgccctacca cgaattcgca    2100
tatgaagggc taaaaatccg ccctgcctgc ccatacaaaa ttgcagtcat aggagtcttc    2160
ggagtaccgg gatctggcaa gtcagctatt atcaagaacc tagttaccag gcaggacctg    2220
gtgactagtg aaagaaaga aaactgccaa gaaatcacca ccgacgtgat gagacaaaga    2280
ggtctagaga tatctgcacg tacgcttgac tcgctgctct tgaatggatg caacagacca    2340
gtcgacgtgt tgtacgtaga cgaggcgttt gcgtgccact ctggaacgct acttgctttg    2400
atcgccttgg tgagaccaag gcagaaagtt gtactttgtg gtgacccgaa gcagtgcggc    2460
ttcttcaata tgatgcagat gaaagtcaac tacaatcaca acatctgcac ccaagtgtac    2520
cacaaaagta tctccaggcg gtgtacactg cctgtgaccg ccattgtgtc atcgttgcat    2580
tacgaaggca aaatgcgcac tacgaatgag tacaacaagc cgattgtagt ggacactaca    2640
ggctcaacaa aacctgaccc tggagacctc gtgttaacgt gcttcagagg gtgggttaaa    2700
caactgcaaa ttgactatcg tggatacgag gtcatgacag cagccgcatc ccaagggtta    2760
accagaaaag gagtttacgc agttagacaa aaagttaatg aaaacccgct ctatgcatca    2820
acgtcagagc acgtcaacgt actcctaacg cgtacggaag gtaaactggt atggaagaca    2880 cttttccggcg acccgtggat aaagacgctg cagaacccac cgaaaggaaa cttcaaagca    2940
actattaagg agtgggaggt ggagcatgca tcaataatgg cgggcatctg cagtcaccaa    3000
atgaccttcg atacattcca aaataaagcc aacgtttgtt gggctaagag cttggtccct    3060
atcctcgaaa cagcggggat aaaactaaat gataggcagt ggtctcagat aattcaagcc    3120
ttcaaagaag acaaagcata ctcacctgaa gtagccctga tgaaatatg tacgcgcatg    3180 tatgggtgg atctagacag cgggctattt tctaaaccgt tggtgtctgt gtattacgcg    3240
gataaccact gggataatag gcctggaggg aaaatgttcg gatttaaccc cgaggcagca    3300
tccattctag aaagaaagta tccattcaca aagggaagt ggaacatcaa caagcagatc    3360
tgcgtgacta ccaggaggat agaagacttt aaccctacca ccaacatcat accggccaac    3420
aggagactac cacactcatt agtggccgaa caccgcccag taaaagggga aagaatggaa    3480
tggctggtta caagataaa cggccaccac gtgctcctgg tcagtggcta taaccttgca    3540
ctgcctacta agagagtcac ttgggtagcg ccgttaggtg tccgcggagc ggactacaca    3600
tacaacctag agttgggtct gccagcaacg cttggtaggt atgaccttgt ggtcataaac    3660
atccacacac cttttcgcat acaccattac caacagtgcg tcgaccacgc aatgaaactg    3720
```

-continued

```
caaatgctcg ggggtgactc attgagactg ctcaaaccgg gcggctctct attgatcaga    3780
gcatatggtt acgcagatag aaccagtgaa cgagtcatct gcgtattggg acgcaagttt    3840
agatcgtcta gagcgttgaa accaccatgt gtcaccagca acactgagat gttttcctta   3900
ttcagcaact ttgacaatgg cagaaggaat ttcacaactc atgtcatgaa caatcaactg    3960
aatgcagcct tcgtaggaca ggtcacccga gcaggatgtg caccgtcgta ccgggtaaaa    4020
cgcatggaca tcgcgaagaa cgatgaagag tgcgtagtta acgccgctaa ccctcgcggg    4080
ttaccgggtg acggtgtttg caaggcagta tacaaaaaat ggccggagtc ctttaagaac    4140
agtgcaacac cagtgggaac cgcaaaaaca gttatgtgcg gtacgtatcc agtaatccac    4200
gctgttggac caaacttctc taattattcg gagcctgaag gggaccggga attggcagct    4260
gcctatcgag aagtcgcaaa ggaagtaact aggctgggag taaatagtgt agctatacct    4320
ctcctctcca caggtgtata ctcaggaggg aaagacaggc tgacccagtc actgaaccac    4380
ctctttacag ccatggactc gacggatgca gacgtggtca tctactgccg cgacaaagaa    4440
tgggagaaga aaatatctga ggccatacag atgcggaccc aagtagagct gctggatgag    4500
cacatctcca tagactgcga tattgttcgc gtgcaccctg acagcagctt ggcaggcaga    4560
aaaggataca gcaccacgga aggcgcactg tactcatatc tagaagggac ccgttttcat    4620
cagacggctg tggatatggc ggagatacat actatgtggc caaagcaaac agaggccaat    4680
gagcaagtct gcctatatgc cctgggggaa agtattgaat cgatcaggca gaaatgcccg    4740
gtggatgatg cagacgcatc atctcccccc aaaactgtcc cgtgcctttg ccgttacgct    4800
atgactccag aacgcgtcac ccggcttcgc atgaaccacg tcacaagcat aattgtgtgt    4860
tcttcgtttc ccctcccaaa gtacaaaata gaaggagtgc aaaaagtcaa atgctctaag    4920
gtaatgctat ttgaccacaa cgtgccatcg cgcgtaagtc aagggaata tagatcttcc    4980
caggagtctg cacaggaggc gagtacaatc acgtcactga cgcatagtca attcgaccta    5040
agcgttgatg gcgagatact gccccgtcccg tcagacctgg atgctgacgc cccagcccta    5100
gaaccagcac tagacgacgg ggcgacacac acgctgccat ccacaaccgg aaaccttgcg    5160
gccgtgtctg actgggtaat gagcaccgta cctgtcgcgc cgcccagaag aaggcgaggg    5220
agaaacctga ctgtgacatg tgacgagaga gaagggaata taacacccat ggctagcgtc    5280
cgattcttta gggcagagct gtgtccggtc gtacaagaaa cagcggagac gcgtgacaca    5340
gcaatgtctc ttcaggcacc accgagtacc gccacggaac cgaatcatcc gccgatctcc    5400
ttcgagcat caagcgagac gttcccatt acatttgggg acttcaacga aggagaaatc    5460
gaaagcttgt cttctgagct actaactttc ggagacttct taccaggaga agtggatgac    5520
ttgacagaca gcgactggtc cacgtgctca gacacggacg acgagttatg actagacagg    5580
gcaggtgggt atatattctc gtcggacacc ggtccaggtc atttacaaca gaagtcagta    5640
cgccagtcag tgctgccggt gaacaccctg gaggaagtcc acgaggagaa gtgttaccca    5700
cctaagctgg atgaagcaaa ggagcaacta ttacttaaga aactccagga gagtgcatcc    5760
atggccaaca gaagcaggta tcagtcgcgc aaagtagaaa acatgaaagc agcaatcatc    5820
cagagactaa agagaggctg tagactatac ttaatgtcag agaccccaaa agtccctact    5880
taccggacta catatccggc gcctgtgtac tcgcctccga tcaacgtccg attgtccaat    5940
cccgagtccg cagtggcagc atgcaatgag ttcttagcta gaaactatcc aactgtctca    6000
tcataccaaa ttaccgacga gtatgatgca tatctagaca tggtgacggg tcggagagt    6060
tgcctggacc gagcgacatt caatccgtca aaactcagga gctacccgaa acagcacgct    6120
```

-continued

| | |
|---|---|
| taccacgcgc cctccatcag aagcgctgta ccgtccccat tccagaacac actacagaat | 6180 |
| gtactggcag cagccacgaa aagaaactgc aacgtcacac agatgaggga attacccact | 6240 |
| ttggactccg cagtattcaa cgtggagtgt ttcaaaaaat tcgcatgcaa ccaagaatac | 6300 |
| tgggaagaat ttgctgccag ccctattagg ataacaactg agaatttagc aacctatgtt | 6360 |
| actaaactaa aagggccaaa agcagcagcg ctattcgcaa aaacccataa tctactgcca | 6420 |
| ctacaggaag taccaatgga taggttcaca gtagatatga aaagggacgt gaaggtgact | 6480 |
| cctggtacaa agcatacaga ggaaagacct aaggtgcagg ttatacaggc ggctgaaccc | 6540 |
| ttggcgacag catacctatg tgggattcac agagagctgg ttaggaggct gaacgccgtc | 6600 |
| ctcctaccca atgtacatac actatttgac atgtctgccg aggatttcga tgccatcata | 6660 |
| gccgcacact ttaagccagg agacactgtt ttggaaacgg acatagcctc ctttgataag | 6720 |
| agccaagatg attcacttgc gcttactgct ttgatgctgt tagaggattt aggggtggat | 6780 |
| cactccctgc tggacttgat agaggctgct ttcggagaga tttccagctg tcacctaccg | 6840 |
| acaggtacgc gcttcaagtt cggcgccatg atgaaatcag gtatgttcct aactctgttc | 6900 |
| gtcaacacat tgttaaacat caccatcgcc agccgagtgc tggaagatcg tctgacaaaa | 6960 |
| tccgcgtgcg cggccttcat cggcgacgac aacataatac atggagtcgt ctccgatgaa | 7020 |
| ttgatggcag ccagatgtgc cacttggatg aacatggaag tgaagatcat agatgcagtt | 7080 |
| gtatccttga agccccctta cttttgtgga gggtttatac tgcacgatac tgtgacagga | 7140 |
| acagcttgca gagtggcaga cccgctaaaa aggcttttta aactgggcaa accgctagcg | 7200 |
| gcaggtgacg aacaagatga agatagaaga cgagcgctgg ctgacgaagt gatcagatgg | 7260 |
| caacgaacag ggctaattga tgagctggag aaagcggtat actctaggta cgaagtgcag | 7320 |
| ggtatatcag ttgtggtaat gtccatggcc acctttgcaa gctccagatc caacttcgag | 7380 |
| aagctcagag acccgtcat aactttgtac ggcggtccta ataggtacg cactacagct | 7440 |
| acctattttg cagaagccga cagcaagtat ctaaacacta atcagctaca atggagttca | 7500 |
| tcccaaccca aacttttttac aataggaggt accagcctcg accctggact ccgcgctcta | 7560 |
| ctatccaaat cattaggccc agaccgcgcc ctcagaggca agctgggcaa cttgcccagc | 7620 |
| tgatctcagc agttaataaa ctgacaatgc gcgcggtacc ccaacagaag ccacgcagga | 7680 |
| atcggaagaa taagaagcaa aagcaaaaac aacaggcgcc acaaacaac acaaatcaaa | 7740 |
| agaagcagcc acctaaaaag aaaccggctc aaaagaaaaa gaagccgggc cgcagagaga | 7800 |
| ggatgtgcat gaaaatcgaa aatgattgta ttttcgaagt caagcacgaa ggtaaggtaa | 7860 |
| caggttacgc gtgcctggtg ggggacaaag taatgaaacc agcacacgta aaggggacca | 7920 |
| tcgataacgc ggacctggcc aaactggcct ttaagcggtc atctaagtat gaccttgaat | 7980 |
| gcgcgcagat acccgtgcac atgaagtccg acgcttcgaa gttcacccat gagaaaccgg | 8040 |
| aggggtacta caactggcac cacgagcag tacagtactc aggaggccgg ttcaccatcc | 8100 |
| ctacaggtgc tggcaaacca ggggacagcg gcagaccgat cttcgacaac aagggacgcg | 8160 |
| tggtggccat agtcttagga ggagctaatg aaggagcccg tacagccctc tcggtggtga | 8220 |
| cctggaataa agacattgtc actaaaatca ccccgaggg ggccgaagag tggagtcttg | 8280 |
| ccatcccagt tatgtgcctg ctggcaaaca ccacgttccc ctgctcccag ccccttgca | 8340 |
| cgccctgctg ctacgaaaag gaaccggagg aaacccctacg catgcttgag gacaacgtca | 8400 |
| tgagacctgg gtactatcag ctgctacagg catccttaac atgttctccc caccgccagc | 8460 |

```
gacgcagcac caaggacaac ttcaatgtct ataaagccac aagaccatac ttagctcact   8520
gtcccgactg tggagaaggg cactcgtgcc atagtcccgt agcactagaa cgcatcagaa   8580
atgaagcgac agacgggacg ctgaatatcc aggtctcctt gcaaatcgga ataaagacgg   8640
atgcagccca cgattggacc aagctgcgtt atatggacaa ccacatgcca gcagacgcag   8700
agagggcggg gctatttgta agaacatcag caccgtgtac gattactgga caatgggac    8760 acttcatcct ggcccgatgt ccaaaagggg aaactctgac ggtgggattc actgacagta   8820
ggaagattag tcattcatgt acgcacccat ttcaccacga ccctcctgtg ataggtcggg   8880
aaaaattcca ttcccgaccg cagcacggta aagagctacc ttgcagcacg tacgtgcaga   8940
gcaccgccgc aactaccgag gagatagagg tacacatgcc cccagacacc cctgatcgca   9000
cattaatgtc acaacagtcc ggcaacgtaa agatcacagt caatggccag acggtgcggt   9060
acaagtgtaa ttgcggtggc tcaaatgaag gactaacaac tacagacaaa gtgattaata   9120
actgcaaggt tgatcaatgt catgccgcgg tcaccaatca caaaaagtgg cagtataact   9180
cccctctggt cccgcgtaat gctgaacttg gggaccgaaa aggaaaaatt cacatcccgt   9240
ttccgctggc aaatgcaaca tgcagggtgc ctaaagcaag gaaccccacc gtgacgtacg   9300
ggaaaaacca agttatcatg ctactgtatc ctgaccaccc aacactcctg tcctaccgga   9360
atatgggaga agaaccaaac tatcaagaag agtgggtgat gcataagaag gaagtcgtgc   9420
taaccgtgcc gactgaaggg ctcgaggtca cgtggggcaa caacgagccg tataagtatt   9480
ggccgcagtt atctacaaac ggtacagccc atggccaccc gcatgagata attctgtatt   9540
attatgagct gtaccctact atgactgtag tagttgtgtc agtggccacg ttcatactcc   9600
tgtcgatggt gggtatggca gcggggatgt gcatgtgtgc acgacgcaga tgcatcacac   9660
cgtatgaact gacaccagga gctaccgtcc ctttcctgct tagcctaata tgctgcatca   9720
gaacagctaa agcggccaca taccaagagg ctgcgatata cctgtggaac gagcagcaac   9780
cttttgtttg gctacaagcc cttattccgc tggcagccct gattgtccta tgcaactgtc   9840
tgagactctt accatgctgc tgtaaaacgt tggcttttt agccgtaatg agcgtcggtg    9900
cccacactgt gagcgcgtac gaacacgtaa cagtgatccc gaacacggtg ggagtaccgt   9960
ataagactct agtcaataga cctggctaca gccccatggt attggagatg gaactactgt  10020
cagtcacttt ggagccaaca ctatcgcttg attacatcac gtgcgagtac aaaaccgtca  10080
tcccgtctcc gtacgtgaag tgctgcggta cagcagagtg caaggacaaa aacctacctg  10140
actacagctg taaggtcttc accggcgtct acccatttat gtggggcggc gcctactgct  10200
tctgcgacgc tgaaaacacg cagttgagcg aagcacatgt ggagaagtcc gaatcatgca  10260
aaacagaatt tgcatcagca tacagggctc ataccgcatc tgcatcagct aagctccgcg  10320
tcctttacca aggaaataac atcactgtaa ctgcctatgc aaacggcgac catgccgtca  10380
cagttaagga cgccaaattc attgtggggc caatgtcttc agcctggaca cctttcgaca  10440
acaaaattgt ggtgtacaaa ggtgacgtct ataacatgga ctacccgccc tttggcgcag  10500
gaagaccagg acaatttggc gatatccaaa gtcgcacacc tgagagtgaa gacgtctatg  10560
ctaatacaca actggtactg cagagaccgg ctgcgggtac ggtacacgtg ccatactctc  10620
aggcaccatc tggctttaag tattggctaa agaacgcgg ggcgtcactg cagcacacag  10680
caccatttgg ctgccaaata gcaacaaacc cggtaagagc ggtgaactgc gccgtaggga  10740 acatgccat ctccatcgac ataccggaag cggccttcac tagggtcgtc gacgcgccct  10800 cttaacgga catgtcgtgc gaggtaccag cctgcaccca ttcctcagac tttgggggcg  10860
```

-continued tcgccattat taaatatgca gccagcaaga aaggcaagtg tgcggtgcat tcgatgacta 10920
acgccgtcac tattcgggaa gctgagatag aagttgaagg gaattctcag ctgcaaatct 10980
ctttctcgac ggccttagcc agcgccgaat tccgcgtaca agtctgttct acacaagtac 11040
actgtgcagc tgagtgccac cccccgaagg accacatagt caactacccg gcgtcacata 11100
ccaccctcgg ggtccaggac atctccgcta cggcgatgtc atgggtgcag aagatcacgg 11160
gaggtgtggg actggttgtt gctgttgccg cactgattct aatcgtggtg ctatgcgtgt 11220
cgttcagcag gcac 11234

<210> SEQ ID NO 18
<211> LENGTH: 11234
<212> TYPE: DNA
<213> ORGANISM: Chikungunya virus

<400> SEQUENCE: 18
atggatcctg tgtacgtgga catagacgct gacagcgcct tttgaaggc cctgcaacgt 60 gcgtacccca tgtttgaggt ggaaccaagg caggtcacac cgaatgacca tgctaatgct 120
agagcgttct cgcatctagc tataaaacta atagagcagg aaattgaccc cgactcaacc 180
atcctggata tcggcagtgc gccagcaagg aggatgatgt cggacaggaa gtaccactgc 240
gtctgcccga tgcgcagtgc ggaagatccc gagagactcg ctaattatgc gagaaagcta 300
gcatctgccg caggaaaagt cctggacaga aacatctctg gaaagatcgg ggacttacaa 360
gcagtaatgg ccgtgccaga caaggagacg ccaacattct gcttacacac agacgtctca 420
tgtagacaga gagcagacgt cgctatatac caagacgtct atgctgtaca cgcacccacg 480
tcgctatacc accaggcgat taaaggggtc caagtggcgt actgggttgg gttcgacaca 540
accccgttca tgtacaatgc catggcgggt gcctacccct catactcgac aaactgggca 600
gatgagcagg tactgaaggc taagaacata ggattatgtt caacagacct gacggaaggt 660
agacgaggca agttgtctat tatgagaggg aaaaagctaa aaccgtgcga ccgtgtgctg 720
ttctcagtag ggtcaacgct ttacccggaa agccgcaagc tacttaagag ctggcacctg 780
ccatcggtgt tccatttaaa gggcaaactc agcttcacat gccgctgtga tacagtggtt 840
tcgtgtgagg gctacgtcgt taagagaata acgatgagcc caggccttta tggaaaaacc 900
acagggtatg cggtaaccca ccacgcagac ggattcctga tgtgcaagac taccgacacg 960
gttgacggcg aaagagtgtc attctcggtg tgcacatacg tgccggcgac catttgtgat 1020
caaatgaccg gcatccttgc tacagaagtc acgccggagg atgcacagaa gctgttggtg 1080
gggctgaacc agagaatagt ggttaacggc agaacgcaac ggaatacgaa caccatgaaa 1140
aattatctgc ttcccgtggt cgcccaagcc ttcagtaagt gggcaaagga gtgccggaaa 1200
gacatggaag atgaaaaact cctgggggtc agagaaagaa cactgacctg ctgctgtcta 1260
tgggcattca agaagcagaa aacacacacg gtctacaaga ggcctgatac ccagtcaatt 1320
cagaaggttc aggccgagtt tgacagcttt gtggtaccga gtctgtggtc gtccgggttg 1380
tcaatccctt tgaggactag aatcaaatgg ttgttaagca aggtgccaaa aaccgacctg 1440
atcccataca gcggagacgc ccgagaagcc cgggacgcag aaaaagaagc agaggaagaa 1500
cgagaagcag aactgactcg cgaagcccta ctacctctac aggcagcaca ggaagatgtt 1560
caggtcgaaa tcgacgtgga acagcttgag gacagagcgg gcgcaggaat aatagagact 1620
ccgagaggag ctatcaaagt tactgcccaa ccaacagacc acgtcgtggg agagtacctg 1680

```
gtactctccc cgcagaccgt actacgtagc cagaagctca gtctgattca cgctttggcg   1740
gagcaagtga agacgtgcac gcacaacgga cgagcaggga ggtatgcggt cgaagcgtac   1800
gacggccgag tcctagtgcc ctcaggctat gcaatctcgc ctgaagactt ccagagtcta   1860
agcgaaagcg caacgatggt gtataacgaa agagagttcg taaacagaaa gctacaccat   1920
attgcgatgc acggaccagc cctgaacacc gacgaagagt cgtatgagct ggtgagggca   1980
gagaggacag aacacgagta cgtctacgac gtggatcaga gaagatgctg taagaaggaa   2040
gaagccgcag gactggtact ggtgggcgac ttgactaatc cgccctacca cgaattcgca   2100
tatgaagggc taaaaatccg ccctgcctgc ccatacaaaa ttgcagtcat aggagtcttc   2160
ggagtaccgg gatctggcaa gtcagctatt atcaagaacc tagttaccag gcaggacctg   2220
gtgactagtg gaaagaaaga aaactgccaa gaaatcacca ccgacgtgat gagacagaga   2280
ggtctagaga tatctgcacg tacggttgac tcgctgctct tgaatggatg caacagacca   2340
gtcgacgtgt tgtacgtaga cgaggcgttt gcgtgccact ctggaacgct acttgctttg   2400
atcgccttgg tgagaccaag gcagaaagtt gtactttgtg gtgacccgaa gcagtgcggc   2460
ttcttcaata tgatgcagat gaaagtcaac tacaatcaca acatctgcac ccaagtgtac   2520
cacaaaagta tctccaggcg tgtgtacactg cctgtgaccg ccattgtgtc atcgttgcat   2580
tacgaaggca aaatgcgcac tacgaatgag tacaacaagc cgattgtagt ggacactaca   2640
ggctcaacaa aacctgaccc tggagacctc gtgttaacgt gcttcagagg gtgggttaaa   2700
caactgcaaa ttgactatcg tggatacgag gtcatgacag cagccgcatc ccaagggtta   2760
accagaaaag gagtttacgc agttagacaa aaagttaatg aaaacccgct ctatgcatca   2820
acgtcagagc acgtcaacgt actcctaacg cgtacggaag gtaaactggt atggaagaca   2880 cttttccggcg acccgtggat aaagacgctg cagaacccac cgaaaggaaa cttcaaagca   2940
actattaagg agtgggaggt ggagcatgca tcaataatgg cgggcatctg cagtcaccaa   3000
atgaccttcg atacattcca aaataaagcc aacgtttgtt gggctaagag cttggtccct   3060
atcctcgaaa cagcggggat aaaactaaat gataggcagt ggtctcagat aattcaagcc   3120
ttcaaagaag acaaagcata ctcacctgaa gtagccctga atgaaatatg tacgcgcatg   3180 tatgggggtgg atctagacag cgggctattt tctaaaccgt tggtgtctgt gtattacgcg   3240
gataaccact gggataatag gcctggaggg aaaatgttcg gatttaaccc cgaggcagca   3300
tccattctag aaagaaagta tccattcaca aaagggaagt ggaacatcaa caagcagatc   3360
tgcgtgacta ccaggaggat agaagacttt aaccctacca ccaacatcat accggccaac   3420
aggagactac cacactcatt agtggccgaa caccgcccag taaaggggga aagaatggaa   3480
tggctggtta acaagataaa cggccaccac gtgctcctgg tcagtggcta taacctttgca   3540 ctgcctacta agagagtcac ttgggtagcg ccgttaggtg tccgcggagc ggactacaca   3600
tacaacctag agttgggtct gccagcaacg cttggtaggt atgaccttgt ggtcataaac   3660
atccacacac ttttcgcat acaccattac caacagtgcg tcgaccacgc aatgaaactg   3720
caaatgctcg ggggtgactc attgagactg ctcaaaccgg gcggctctct attgatcaga   3780
gcatatggtt acgcagatag aaccagtgaa cgagtcatct gcgtatttggg acgcaagttt   3840 agatcgtcta gagcgttgaa accaccatgt gtcaccagca acactgagat gttttttccta   3900 ttcagcaact tgacaatgg cagaaggaat ttcacaactc atgtcatgaa caatcaactg   3960
aatgcagcct tcgtaggaca ggtcacccga gcaggatgtg caccgtcgta ccgggtaaaa   4020
cgcatggaca tcgcgaagaa cgatgaagag tgcgtagtca acgccgctaa ccctcgcggg   4080
```

```
ttaccgggtg acggtgtttg caaggcagta tacaaaaaat ggccggagtc ctttaagaac    4140
agtgcaacac cagtgggaac cgcaaaaaca gttatgtgcg gtacgtatcc agtaatccac    4200
gctgttggac caaacttctc taattattcg gagtctgaag gggaccggga attggcagct    4260
gcctatcgag aagtcgcaaa ggaagtaact aggctgggga taaatagtgt agctatacct    4320
ctcctctcca caggtgtata ctcaggaggg aaagacaggc tgacccagtc actgaaccac    4380
ctctttacag ccatggactc gacgdatgca gacgtggtca tctactgccg cgacaaagaa    4440
tgggagaaga aaatatctga ggccatacag atgcggaccc aagtagagct gctggatgag    4500
cacatctcca tagactgcga tattgttcgc gtgcaccctg acagcagctt ggcaggcaga    4560
aaaggataca gcaccacgga aggcgcactg tactcatatc tagaagggac ccgttttcat    4620
cagacggctg tggatatggc ggagatacat actatgtggc aaagcaaac agaggccaat    4680
gagcaagtct gcctatatgc cctggggdaa agtattgaat cgatcaggca gaaatgcccg    4740
gtggatgatg cagacgcatc atctccccccc aaaactgtcc cgtgcctttg ccgttacgct    4800
atgactccag aacgcgtcac ccggcttcgc atgaatcacg tcacaagcat aattgtgtgt    4860
tcttcgtttc ccctcccaaa gtacaaaata gaaggagtgc aaaaagtcaa atgctctaag    4920
gtaatgctat ttgaccacaa cgtgccatcg cgcgtaagtc caagggaata tagatcttcc    4980
caggagtctg cacaggaggc gagtacaatc acgtcactga cgcatagtca attcgaccta    5040
agcgttgatg gcgagatact gcccgtcccg tcagacctgg atgctgacgc cccagcccta    5100
gaaccagcac tagacgacgg ggcgacacac acgctgccat ccacaaccgg aaaccttgcg    5160
gccgtgtctg actgggtaat gagcaccgta cctgtcgcgc cgcccagaag aaggcgaggg    5220
agaaacctga ctgtgacatg tgacgagaga gaagggaata taacacccat ggctagcgtc    5280
cgattcttta gggcagagct gtgtccggtc gtacaagaaa cagcggagac gcgtgacaca    5340
gcaatgtctc ttcaggcacc accgagtacc gccacggaac cgaatcatcc gccgatctcc    5400
ttcggagcat caagcgagac gttccccatt acatttgggg acttcaacga aggagaaatc    5460
gaaagcttgt cttctgagct actaactttc ggagacttct taccaggaga agtggatgac    5520
ttgacagaca gcgactggtc cacgtgctca gacacggacg acgagttatg actagacagg    5580
gcaggtgggt atatattctc gtcggacacc ggtccaggtc atttacaaca gaagtcagta    5640
cgccagtcag tgctgccggt gaacaccctg gaggaagtcc acgaggagaa gtgttaccca    5700
cctaagctgg atgaagcaaa ggagcaacta ttacttaaga aactccagga gagtgcatcc    5760
atggccaaca gaagcaggta tcagtcgcgc aaagtagaaa acatgaaagc agcaatcatc    5820
cagagactaa agagaggctg tagactatac ttaatgtcag agaccccaaa agtccctact    5880
taccggacta catatccggc gcctgtgtac tcgcctccga tcaacgtccg attgtccaat    5940
cccgagtccg cagtggcagc atgcaatgag ttcttagcta gaaactatcc aactgtctca    6000
tcataccaaa ttaccgacga gtatgatgca tatctagaca tggtgdacgg gtcggagagt    6060
tgcctggacc gagcgacatt caatccgtca aaactcagga gctacccgaa acagcacgct    6120
taccacgcgc cctccatcag aagcgctgta ccgtccccat ccagaacac actacagaat    6180
gtactggcag cagccacgaa aagaaactgc aacgtcacac agatgaggga attacccact    6240
ttggactccg cagtattcaa cgtggagtgt ttcaaaaaat tcgcatgcaa ccaagaatac    6300
tgggaagaat ttgctgccag ccctattagg ataacaactg agaatttagc aacttatgtt    6360
actaaactaa aagggccaaa agcagcagcg ctattcgcaa aaacccataa tctactgcca    6420
```

```
ctacaggaag taccaatgga taggttcaca gtagatatga aaagggacgt gaaggtgact    6480
cctggtacaa agcatacaga ggaaagacct aaggtgcagg ttatacaggc ggctgaaccc    6540
ttggcgacag catacctatg tgggattcac agagagctgg ttaggaggct gaacgccgtc    6600
ctcctaccca atgtacatac actatttgac atgtctgccg aggatttcga tgccatcata    6660
gccgcacact ttaagccagg agacactgtt ttggaaacgg acatagcctc ctttgataag    6720
agccaagatg attcacttgc gcttactgct ttgatgctgt tagaggattt aggggtggat    6780
cactccctgc tggacttgat agaggctgct ttcggagaga tttccagctg tcacctaccg    6840
acaggtacgc gcttcaagtt cggcgccatg atgaaatcag gtatgttcct aactctgttc    6900
gtcaacacat tgttaaacat caccatcgcc agccgagtgc tggaagatcg tctgacaaaa    6960
tccgcgtgcg cggccttcat cggcgacgac aacataatac atggagtcgt ctccgatgaa    7020
ttgatggcag ccagatgtgc cacttggatg aacatggaag tgaagatcat agatgcagtt    7080
gtatccttga agccccctta cttttgtgga gggtttatac tgcacgatac tgtgacagga    7140
acagcttgca gagtggcaga cccgctaaaa aggcttttta aactgggcaa accgctagcg    7200
gcaggtgacg aacaagatga agatagaaga cgagcgctgg ctgacgaagt gatcagatgg    7260
caacgaacag ggctaattga tgagctggag aaagcggtat actctaggta cgaagtgcag    7320
ggtatatcag ttgtggtaat gtccatggcc acctttgcaa gctccagatc caacttcgag    7380
aagctcagag gacccgtcat aactttgtac ggcggtccta ataggtacg cactacagct    7440 acctattttg cagaagccga cagcaagtat ctaaacacta atcagctaca atggagttca    7500
tcccaaccca aacttttttac aataggaggt accagcctcg accctggact ccgcgctcta    7560
ctatccaaat cattaggccc agaccgcgcc tcagaggca agctgggcaa cttgcccagc    7620
tgatctcagc agttaataaa ctgacaatgc gcgcggtacc ccaacagaag ccacgcagga    7680
atcggaagaa taagaagcaa agcaaaaac aacaggcgcc acaaacaac acaaatcaaa    7740 agaagcagcc acctaaaaag aaaccggctc aaaagaaaaa gaagccgggc cgcagagaga    7800
ggatgtgcat gaaaatcgaa aatgattgta ttttcgaagt caagcacgaa ggtaaggtaa    7860
caggttacgc gtgcctggtg ggggacaaag taatgaaacc agcacacgta aagggggacca    7920 tcgataacgc ggacctggcc aaactggcct ttaagcggtc atctaagtat gaccttgaat    7980
gcgcgcagat acccgtgcac atgaagtccg acgcttcgaa gttcacccat gagaaaccgg    8040
aggggtacta caactggcac cacggagcag tacagtactc aggaggccgg ttcaccatcc    8100
ctacaggtgc tggcaaacca ggggacagcg gcagaccgat cttcgacaac aagggacgcg    8160
tggtggccat agtcttagga ggagttaatg aaggagcccg tacagccctc tcggtggtga    8220
cctggaataa agacattgtc actaaaatca cccccgaggg ggccgaagag tggagtcttg    8280
ccatcccagt tatgtgcctg ctggcaaaca ccacgttccc ctgctcccag cccccttgca    8340
cgccctgctg ctacgaaaag gaaccggagg aaacccacg catgcttgag acaacgtca    8400 tgagacctgg gtactatcag ctgctacagg catccttaac atgttctccc caccgccagc    8460
gacgcagcac caaggacaac ttcaatgtct ataaagccac aagaccatac ttagctcact    8520
gtcccgactg tggagaaggg cactcgtgcc atagtcccgt agcactagaa cgcatcagaa    8580
atgaagcgac agacgggacg ctgaaaatcc aggtctcctt gcaaatcgga ataaagacgg    8640
atgacagcca cgattggacc aagctgcgtt atatggacaa ccacatgcca gcagacgcag    8700
agagggcggg gctatttgta agaacatcag caccgtgtac gattactgga acaatgggac    8760
acttcatcct ggcccgatgt ccaaaagggg aaactctgac ggtgggattc actgacagta    8820
```

```
ggaagattag tcattcatgt acgcacccat ttcaccacga ccctcctgtg ataggtcggg    8880
aaaaattcca ttcccgaccg cagcacggta aagagctacc ttgcagcacg tacgtgcaga    8940
gcaccgccgc aactaccgag gagatagagg tacacatgcc cccagacacc cctgatcgca    9000
cattaatgtc acaacagtcc ggcaacgtaa agatcacagt caatggccag acggtgcggt    9060
acaagtgtaa ttgcggtggc tcaaatgaag gactaacaac tacagacaaa gtgattaata    9120
actgcaaggt tgatcaatgt catgccgcgg tcaccaatca caaaaagtgg cagtataact    9180
cccctctggt cccgcgtaat gctgaacttg gggaccgaaa aggaaaaatt cacatcccgt    9240
ttccgctggc aaatgcaaca tgcagggtgc ctaaagcaag gaaccccacc gtgacgtacg    9300
ggaaaaacca agtcatcatg ctactgtatc ctgaccaccc aacactcctg tcctaccgga    9360
atatgggaga agaaccaaac tatcaagaag agtgggtgat gcataagaag gaagtcgtgc    9420
taaccgtgcc gactgaaggg ctcgaggtca cgtggggcaa caacgagccg tataagtatt    9480
ggccgcagtt atctacaaac ggtacagccc atggccaccc gcatgagata attctgtatt    9540
attatgagct gtaccctact atgactgtag tagttgtgtc agtggccacg ttcatactcc    9600
tgtcgatggt gggtatggca gcggggatgt gcatgtgtgc acgacgcaga tgcatcacac    9660
cgtatgaact gacaccagga gctaccgtcc ctttcctgct tagcctaata tgctgcatca    9720
gaacagctaa agcggccaca taccaagagg ctgcgatata cctgtggaac gagcagcaac    9780
ctttgttttg gctacaagcc cttattccgc tggcagccct gattgttcta tgcaactgtc    9840
tgagactctt accatgctgc tgtaaaacgc tggcttttt agccgtaatg agcgtcggtg    9900
cccacactgt gagcgcgtac gaacacgtaa cagtgatccc gaacacggtg ggagtaccgt    9960
ataagactct agtcaataga cctggctaca gccccatggt attggagatg gaactactgt   10020
cagtcacttt ggagccaaca ctatcgcttg attacatcac gtgcgagtac aaaaccgtca   10080
tcccgtctcc gtacgtgaag tgctgcggta cagcagagtg caaggacaaa aacctacctg   10140
actacagctg taaggtcttc accggcgtct acccatttat gtggggcggc gcctactgct   10200
tctgcgacgc tgaaaacacg cagttgagcg aagcacatgt ggagaagtcc gaatcatgca   10260
aaacagaatt tgcatcagca tacagggcgc ataccgcatc tgcatcagct aagctccgcg   10320
tcctttacca aggaaataac atcactgtaa ctgcctatgc aaacggcgac catgccgtca   10380
cagttaagga cgccaaattc attgtggggc caatgtcttc agcctggaca cctttcgaca   10440
acaaaattgt ggtgtacaaa ggtgacgtct ataacatgga ctacccgccc tttggcgcac   10500
gaagaccagg acaatttggc gatatccaaa gtcgcacacc tgagagtgaa gacgtctatg   10560
ctaatacaca actggtactg cagagaccgg ctgcgggtac ggtacacgtg ccatactctc   10620
aggcaccatc tggctttaag tattggctaa agaacgcgg ggcgtcactg cagcacacag   10680
caccatttgg ctgccaaata gcaacaaacc cggtaagagc ggtgaactgc gccgtaggga   10740
acatgcccat ctccatcgac ataccggaag cggccttcac tagggtcgtc gacgcgccct   10800
ctttaacgga catgtcgtgc gaggtaccag cctgcaccca ttcctcagac tttgggggcg   10860
tcgccattat taaatatgca gccagcaaga aaggcaagtg tgcggtgcat tcgatgacta   10920
acgccgtcac tattcgggaa gctgagatag aagttgaagg gaattctcag ctgcaaatct   10980
ctttctcgac ggccttagcc agcgccgaat ccgcgtaca agtctgttct acacaagtac   11040
actgtgcagc tgagtgccac ccccccgaagg accacatagt caactacccg cgtcacatag   11100
ccaccctcgg ggtccaggac atctccgcta cggcgatgtc atgggtgcag aagatcacgg   11160
```

<210> SEQ ID NO 19
<211> LENGTH: 11234
<212> TYPE: DNA
<213> ORGANISM: Chikungunya virus

<400> SEQUENCE: 19

```
atggatcctg tgtacgtgga catagacgct gacagcgcct ttttgaaggc cctgcaacgt      60
gcgtacccca tgtttgaggt ggaaccaagg caggtcacac cgaatgacca tgctaatgct     120
agagcgttct cgcatctagc tataaaacta atagagcagg aaattgaccc cgactcaacc     180
atcctggata tcggcagtgc gccagcaagg aggatgatgt cggacaggaa gtaccactgc     240
gtctgcccga tgcgcagtgc ggaagatccc gagagactcg ctaattatgc gagaaagcta     300
gcatctgccg caggaaaagt cctggacaga acatctctg aaagatcgg ggacttacaa       360
gcagtaatgg ccgtgccaga caaggagacg ccaacattct gcttacacac agacgtctca     420
tgtagacaga gagcagacgt cgctatatac caagacgtct atgctgtaca cgcacccacg     480
tcgctatacc accaggcgat taaggggtc cgagtggcgt actgggttgg gttcgacaca      540
accccgttca tgtacaatgc catggcgggt gcctacccct catactcgac aaactgggca     600
gatgagcagg tactgaaggc taagaacata ggattatgtt caacagacct gacggaaggt     660
agacgaggca gttgtctat atgagaggg aaaaagctaa accgtgcga cagtgtgctg         720
ttctcagtag ggtcaacgct ttacccggaa agccgcaagc tacttaagag ctggcacctg     780
ccatcggtgt ccatttaaa gggcaaactc agcttcacat gccgctgtga tacagtggtt      840
tcgtgtgagg gctacgtcgt taagagaata acgatgagcc caggccttta tggaaaaacc     900
acagggtatg cggtaaccca ccacgcagac ggattcctga tgtgcaagac taccgacacg     960
gttgacggcg aaagagtgtc attctcggtg tgcacatacg tgccggcgac catttgtgat    1020
caaatgaccg gcatccttgc tacagaagtc acgccggagg atgcacagaa gctgttggtg    1080
gggctgaacc agagaatagt ggttaacggc agaacgcaac ggatacgaa caccatgaaa    1140
aattatctgc ttcccgtggt cgcccaagcc ttcagtaagt gggcaaagga gtgccggaaa    1200
gacatggaag atgaaaaact cctgggggtc agagaaagaa cactgacctg ctgctgtcta    1260
tgggcattca agaagcagaa aacacacacg gtctacaaga ggcctgatac ccagtcaatt    1320
cagaaggttc aggccgagtt tgacagcttt gtggtaccga gtctgtggtc gtccgggttg    1380
tcaatccctt tgaggactag aatcaaatgg ttgttaagca aggtgccaaa aaccgacctg    1440
atcccataca gcggagacgc ccgagaagcc cgggacgcag aaaaagaagc agaggaagaa    1500
cgagaagcag aactgactcg cgaagcccta ctacctctac aggcagcaca ggaagatgtt    1560
caggtcgaaa tcgacgtgga acagcttgag gacagagcgg cgcaggaat aatagagact    1620
ccgagaggag ctatcaaagt tactgcccaa ccaacagacc acgtcgtggg agagtacctg    1680
gtactctccc cgcagaccgt actacgtagc cagaagctca gtctgattca cgctttggcg    1740
gagcaagtga gacgtgcac gcacaacgga cgagcaggga gtatgcggt cgaagcgtac    1800
gacggccgag tcctagtgcc ctcaggctat gcaatctcgc ctgaagactt ccagagtcta    1860
agcgaaagcg caacgatggt gtataacgaa agagagttcg taaacagaaa gctacaccat    1920
attgcgatgc acggaccagc cctgaacacc gacgaagagt cgtatgagct ggtgagggca    1980
gagaggacag aacacgagta cgtctacgac gtggatcaga agatgctg taagaaggaa      2040
```

```
gaagccgcag gactggtact ggtgggcgac ttgactaatc cgccctacca cgaattcgca   2100
tatgaagggc taaaaatccg ccctgcctgc ccatacaaaa ttgcagtcat aggagtcttc   2160
ggagtaccgg gatctggcaa gtcagctatt atcaagaacc tagttaccag gcaggacctg   2220
gtgactagtg gaaagaaaga aaactgccaa gaaatcacca ccgacgtgat gagacagaga   2280
ggtctagaga tatctgcacg tacggttgac tcgctgctct tgaatggatg caacagacca   2340
gtcgacgtgt tgtacgtaga cgaggcgttt gcgtgccact ctggaacgct acttgctttg   2400
atcgccttgg tgagaccaag gcagaaagtt gtactttgtg gtgacccgaa gcagtgcggc   2460
ttcttcaata tgatgcagat gaaagtcaac tacaatcaca acatctgcac ccaagtgtac   2520
cacaaaagta tctccaggcg gtgtacactg cctgtgaccg ccattgtgtc atcgttgcat   2580
tacgaaggca aaatgcgcac tacgaatgag tacaacaagc cgattgtagt ggacactaca   2640
ggctcaacaa aacctgaccc tggagacctc gtgttaacgt gcttcagagg gtgggttaaa   2700
caactgcaaa ttgactatcg tggatacgag gtcatgacag cagccgcatc ccaagggtta   2760
accagaaaag gagtttacgc agttagacaa aaagttaatg aaaacccgct ctatgcatca   2820
acgtcagagc acgtcaacgt actcctaacg cgtacggaag gtaaactggt atggaagaca   2880 cttttccggcg acccgtggat aaagacgctg cagaacccac cgaaaggaaa cttcaaagca   2940
actattaagg agtgggaggt ggagcatgca tcaataatgg cgggcatctg cagtcaccaa   3000
atgaccttcg atacattcca aaataaagcc aacgtttgtt gggctaagag cttggtccct   3060
atcctcgaaa cagcggggat aaaactaaat gataggcagt ggtctcagat aattcaagcc   3120 ttcaagaag acaaagcata ctcacctgaa gtagccctga atgaaatatg tacgcgcatg   3180
tatggggtgg atctagacag cgggctattt tctaaaccgt tggtgtctgt gtattacgcg   3240
gataaccact gggataatag gcctggaggg aaaatgttcg gatttaaccc cgaggcagca   3300
tccattctag aaagaaagta tccattcaca aaagggaagt ggaacatcaa caagcagatc   3360
tgcgtgacta ccaggaggat agaagacttt aaccctacca ccaacatcat accggccaac   3420
aggagactac cacactcatt agtggccgaa caccgcccag taaaaggggga agaatggaa   3480 tggctggtta acaagataaa cggccaccac gtgctcctgg tcagtggcta taaccttgca   3540
ctgcctacta agagagtcac ttgggtagcg ccgttaggtg tccgcggagc ggactacaca   3600
tacaacctag agttgggtct gccagcaacg cttggtaggg atgaccttgt ggtcataaac   3660
atccacacac cttttcgcat acaccattac caacagtgcg tcgaccacgc aatgaaactg   3720
caaatgctcg ggggtgactc attgagactg ctcaaaccgg gcggctctct attgatcaga   3780
gcatatggtt acgcagatag aaccagtgaa cgagtcatct gcgtattggg acgcaagttt   3840
agatcgtcta gagcgttgaa accaccatgt gtcaccagca acactgagat gttttttccta   3900 ttcagcaact ttgacaatgg cagaaggaat ttcacaactc atgtcatgaa caatcaactg   3960
aatgcagcct tcgtaggaca ggtcacccga gcaggatgtg caccgtcgta ccgggtaaaa   4020
cgcatggaca tcgcgaagaa cgatgaagag tgcgtagtca acgccgctaa ccctcgcggg   4080
ttaccgggtg acggtgtttg caaggcagta tacaaaaaat ggccggagtc ctttaagaac   4140
agtgcaacac cagtgggaac cgcaaaaaca gttatgtgcg gtacgtatcc agtaatccac   4200
gctgttggac caaacttctc taattattcg gagtctgaag gggaccggga attggcagct   4260
gcctatcgag aagtcgcaaa ggaagtaact aggctgggag taaatagtgt agctatacct   4320
ctcctctcca caggtgtata ctcaggaggg aaagacaggc tgacccagtc actgaaccac   4380
```

```
ctctttacag ccatggactc gacggatgca gacgtggtca tctactgccg cgacaaagaa   4440
tgggagaaga aaatatctga ggccatacag atgcggaccc aagtagagct gctggatgag   4500
cacatctcca tagactgcga tattgttcgc gtgcaccctg acagcagctt ggcaggcaga   4560
aaaggataca gcaccacgga aggcgcactg tactcatatc tagaagggac ccgttttcat   4620
cagacggctg tggatatggc ggagatacat actatgtggc caaagcaaac agaggccaat   4680
gagcaagtct gcctatatgc cctgggggaa agtattgaat cgatcaggca gaaatgcccg   4740
gtggatgatg cagacgcatc atctccccccc aaaactgtcc cgtgcctttg ccgttacgct   4800
atgactccag aacgcgtcac ccggcttcgc atgaatcacg tcacaagcat aattgtgtgt   4860
tcttcgtttc ccctcccaaa gtacaaaata gaaggagtgc aaaaagtcaa atgctctaag   4920
gtaatgctat ttgaccacaa cgtgccatcg cgcgtaagtc aagggaata tagatcttcc   4980
caggagtctg cacaggaggc gagtacaatc acgtcactga cgcatagtca attcgaccta   5040
agcgttgatg cgagatact gcccgtcccg tcagacctgg atgctgacgc cccagcccta   5100
gaaccagcac tagacgacgg ggcgacacac acgctgccat ccacaaccgg aaaccttgcg   5160
gccgtgtctg actgggtaat gagcaccgta cctgtcgcgc cgcccagaag aaggcgaggg   5220
agaaacctga ctgtgacatg tgacgagaga aagggaata taacacccat ggctagcgtc   5280
cgattcttta gggcagagct gtgtccggtc gtacaagaaa cagcggagac gcgtgacaca   5340
gcaatgtctc ttcaggcacc accgagtacc gccacgaaac cgaatcatcc gccgatctcc   5400
ttcggagcat caagcgagac gttcccccatt acatttgggg acttcaacga aggagaaatc   5460
gaaagcttgt cttctgagct actaactttc ggagacttct taccaggaga agtggatgac   5520
ttgacagaca gcgactggtc cacgtgctca gacacggacg acgagttatg actagacagg   5580
gcaggtgggt atatattctc gtcggacacc ggtccaggtc atttacaaca gaagtcagta   5640
cgccagtcag tgctgccggt gaacaccctg gaggaagtcc acgaggagaa gtgttaccca   5700
cctaagctgg atgaagcaaa ggagcaacta ttacttaaga aactccagga gagtgcatcc   5760
atggccaaca gaagcaggta tcagtcgcgc aaagtagaaa acatgaaagc agcaatcatc   5820
cagagactaa agagaggctg tagactatac ttaatgtcag agaccccaaa agtccctact   5880
taccggacta catatccggc gcctgtgtac tcgcctccga tcaacgtccg attgtccaat   5940
cccgagtccg cagtggcagc atgcaatgag ttcttagcta gaaactatcc aactgtctca   6000
tcataccaaa ttaccgacga gtatgatgca tatctagaca tggtggacgg gtcggagagt   6060
tgcctggacc gagcgacatt caatccgtca aaactcagga gctacccgaa acagcacgct   6120
taccacgcgc cctccatcag aagcgctgta ccgtcccccat tccagaacac actacagaat   6180
gtactggcag cagccacgaa aagaaactgc aacgtcacac agatgaggga attacccact   6240
ttggactccg cagtattcaa cgtggagtgt ttcaaaaaat tcgcatgcaa ccaagaatac   6300
tgggaagaat ttgctgccag ccctattagg ataacaactg agaatttagc aacttatgtt   6360
actaaactaa aagggccaaa agcagcagcg ctattcgcaa aaacccataa tctactgcca   6420
ctacaggaag taccaatgga taggttcaca gtagatatga aagggacgt gaaggtgact   6480
cctggtacaa agcatacaga ggaaagacct aaggtgcagg ttatacaggc ggctgaaccc   6540
ttggcgacag catacctatg tgggattcac agagagctgg ttaggaggct gaacgccgtc   6600
ctcctaccca atgtacatac actatttgac atgtctgccg aggatttcga tgccatcata   6660
gccgcacact ttaagccagg agacactgtt ttggaaacgg acatagcctc ctttgataag   6720
agccaagatg attcacttgc gcttactgct ttgatgctgt tagaggattt aggggtggat   6780
```

```
cactccctgc tggacttgat agaggctgct ttcggagaga tttccagctg tcacctaccg    6840
acaggtacgc gcttcaagtt cggcgccatg atgaaatcag gtatgttcct aactctgttc    6900
gtcaacacat tgttaaacat caccatcgcc agccgagtgc tggaagatcg tctgacaaaa    6960
tccgcgtgcg cggccttcat cggcgacgac aacataatac atggagtcgt ctccgatgaa    7020
ttgatggcag ccagatgtgc cacttggatg aacatggaag tgaagatcat agatgcagtt    7080
gtatccttga aagccccta cttttgtgga gggtttatac tgcacgatac tgtgacagga    7140
acagcttgca gagtggcaga cccgctaaaa aggctttta aactgggcaa accgctagcg    7200
gcaggtgaca acaagatga agatagaaga cgagcgctgg ctgacgaagt gatcagatgg    7260
caacgaacag ggctaattga tgagctggag aaagcggtat actctaggta cgaagtgcag    7320
ggtatatcag ttgtggtaat gtccatggcc acctttgcaa gctccagatc caacttcgag    7380
aagctcagag acccgtcat aactttgtac ggcggtccta aataggtacg cactacagct    7440
acctattttg cagaagccga cagcaagtat ctaaacacta atcagctaca atggagttca    7500
tcccaaccca aacttttac aataggaggt accagcctcg accctggact ccgcgctcta    7560
ctatccaaat cattaggccc agaccgcgcc ctcagaggca agctgggcaa cttgcccagc    7620
tgatctcagc agttaataaa ctgacaatgc gcgcggtacc caacagaag ccacgcagga    7680 atcggaagaa taagaagcaa aagcaaaaac aacaggcgcc acaaaacaac acaaatcaaa    7740
agaagcagcc acctaaaaag aaaccggctc aaaagaaaaa gaagccgggc cgcagagaga    7800
ggatgtgcat gaaaatcgaa aatgattgta ttttcgaagt caagcacgaa ggtaaggtaa    7860
caggttacgc gtgcctggtg ggggacaaag taatgaaacc agcacacgta aaggggacca    7920
tcgataacgc ggacctggcc aaactggcct ttaagcggtc atctaagtat gaccttgaat    7980
gcgcgcagat acccgtgcac atgaagtccg acgcttcgaa gttcacccat gagaaaccgg    8040
agggtactaa caactggcac cacgggcag tacagtactc aggaggccgg ttcaccatcc    8100
ctacaggtgc tggcaaacca ggggacagcg gcagaccgat cttcgacaac aagggacgcg    8160
tggtggccat agtcttagga ggagctaatg aaggagcccg tacagccctc tcggtggtga    8220 cctgaataa agacattgtc actaaaatca ccccgagggg ggccgaagag tggagtcttg    8280
ccatcccagt tatgtgcctg ctggcaaaca ccacgttccc ctgctcccag cccccttgca    8340
cgccctgctg ctacgaaaag gaaccggagg aaaccctacg catgcttgag gacaacgtca    8400
tgagacctgg gtactatcag ctgctacagg catccttaac atgttctccc caccgccagc    8460
gacgcagcac caaggacaac ttcaatgtct ataaagccac aagaccatac ttagctcact    8520
gtcccgactg tggagaaggg cactcgtgcc atagtcccgt agcactagaa cgcatcagaa    8580
atgaagcgac agacgggacg ctgaaaatcc aggtctcctt gcaaatcgga ataaagacgg    8640
atgacagcca cgattggacc gagctgcgtt atatggacaa ccacatgcca gcagacgcag    8700
agagggcggg gctatttgta agaacatcag caccgtgtac gattactgga caatgggac    8760 acttcatcct ggcccgatgt ccaaagggg aaactctgac ggtgggattc actgacagta    8820
ggaagattag tcattcatgt acgcaccat ttcaccacga ccctcctgtg ataggtcggg    8880
aaaaattcca ttcccgaccg cagcacggta agagctacc ttgcagcacg tacgtgcaga    8940
gcaccgccgc aactaccgag gagatagagg tacacatgcc cccagacacc cctgatcgca    9000
cattaatgtc acaacagtcc ggcaacgtaa agatcacagt caatggccag acggtgcggt    9060
acaagtgtaa ttgcggtggc tcaaatgaag gactaacaac tacagacaaa gtgattaata    9120
```

| | |
|---|---|
| actgcaaggt tgatcaatgt catgccgcgg tcaccaatca caaaaagtgg cagtataact | 9180 |
| cccctctggt cccgcgtaat gctgaacttg gggaccgaaa aggaaaaatt cacatcccgt | 9240 |
| ttccgctggc aaatgcaaca tgcagggtgc ctaaagcaag gaaccccacc gtgacgtacg | 9300 |
| ggaaaaacca agtcatcatg ctactgtatc ctgaccaccc aacactcctg tcctaccgga | 9360 |
| atatgggaga agaaccaaac tatcaagaag agtgggtgat gcataagaag gaagtcgtgc | 9420 |
| taaccgtgcc gactgaaggg ctcgaggtca cgtggggcaa caacgagccg tataagtatt | 9480 |
| ggccgcagtt atctacaaac ggtacagccc atggccaccc gcatgagata attctgtatt | 9540 |
| attatgagct gtaccctact atgactgtag tagttgtgtc agtggccacg ttcatactcc | 9600 |
| tgtcgatggt gggtatggca gcggggatgt gcatgtgtgc acgacgcaga tgcatcacac | 9660 |
| cgtatgaact gacaccagga gctaccgtcc ctttcctgct tagcctaata tgctgcatca | 9720 |
| gaacagctaa agcggccaca taccaagagg ctgcgatata cctgtggaac gagcagcaac | 9780 |
| ctttgttttg gctacaagcc cttattccgc tggcagccct gattgttcta tgcaactgtc | 9840 |
| tgagactctt accatgctgc tgtaaaaacg tggctttttt agccgtaatg agcgtcggtg | 9900 |
| cccacactgt gagcgcgtac gaacacgtaa cagtgatccc gaacacggtg ggagtaccgt | 9960 |
| ataagactct agtcaataga cctggctaca gccccatggt attggagatg gaactactgt | 10020 |
| cagtcacttt ggagccaaca ctatcgcttg attacatcac gtgcgagtac aaaaccgtca | 10080 |
| tcccgtctcc gtacgtgaag tgctgcggta cagcagagtg caaggacaaa aacctacctg | 10140 |
| actacagctg taaggtcttc accggcgtct acccatttat gtggggcggc gcctactgct | 10200 |
| tctgcgacgc tgaaaacacg cagttgagcg aagcacatgt ggagaagtcc gaatcatgca | 10260 |
| aaacagaatt tgcatcagca tacagggcgc ataccgcatc tgcatcagct aagctccgcg | 10320 |
| tcctttacca aggaaataac atcactgtaa ctgcctatgc aaacggcgac catgccgtca | 10380 |
| cagttaagga cgccaaattc attgtggggc caatgtcttc agcctggaca cctttcgaca | 10440 |
| acaaaattgt ggtgtacaaa ggtgacgtct ataacatgga ctaccgcc tttgcgcag | 10500 |
| gaagaccagg acaatttggc gatatccaaa gtcgcacacc tgagagtgaa gacgtctatg | 10560 |
| ctaatacaca actggtactg cagagaccgg ctgcgggtac ggtacacgtg ccatactctc | 10620 |
| aggcaccatc tggctttaag tattggctaa agaacgcgg ggcgtcactg cagcacacag | 10680 |
| caccatttgg ctgccaaata gcaacaaacc cggtaagagc ggtgaactgc gccgtaggga | 10740 |
| acatgcccat ctccatcgac ataccggaag cggccttcac tagggtcgtc gacgcgccct | 10800 |
| ctttaacgga catgtcgtgc gaggtaccag cctgcaccca ttcctcagac tttgggggcg | 10860 |
| tcgccattat taaatatgca gccagcaaga aaggcaagtg tgcggtgcat tcgatgacta | 10920 |
| acgccgtcac tattcgggaa gctgagtag aagttgaagg gaattctcag ctgcaaatct | 10980 |
| ctttctcgac ggccttagcc agcgccgaat tccgcgtaca agtctgttct acacaagtac | 11040 |
| actgtgcagc tgagtgccac ccccgaagg accacatagt caactacccg gcgtcacata | 11100 |
| ccaccctcgg ggtccaggac atctccgcta cggcgatgtc atgggtgcag aagatcacgg | 11160 |
| gaggtgtggg actggttgtt gctgttgccg cactgattct aatcgtggtg ctatgcgtgt | 11220 |
| cgttcagcag gcac | 11234 |

<210> SEQ ID NO 20
<211> LENGTH: 11234
<212> TYPE: DNA
<213> ORGANISM: Chikungunya virus

<400> SEQUENCE: 20

-continued

```
atggatcctg tgtacgtgga catagacgct gacagcgcct ttttgaaggc cctgcaacgt      60
gcgtacccca tgtttgaggt ggaaccaagg caggtcacac cgaatgacca tgctaatgct     120
agagcgttct cgcatctagc tataaaacta atagagcagg aaattgaccc cgactcaacc     180
atcctggata tcggcagtgc gccagcaagg aggatgatgt cggacaggaa gtaccactgc     240
gtctgcccga tgcgcagtgc ggaagatccc gagagactcg ctaattatgc gagaaagcta     300
gcatctgccg caggaaaagt cctggacaga aacatctctg gaaagatcgg ggacttacaa     360
gcagtaatgg ccgtgccaga caaggagacg ccaacattct gcttacacac agacgtctca     420
tgtagacaga gagcagacgt cgctatatac caagacgtct atgctgtaca cgcacccacg     480
tcgctatacc accaggcgat taaggggtc cgagtggcgt actgggttgg gttcgacaca     540
accccgttca tgtacaatgc catggcgggt gcctacccct catactcgac aaactgggca     600
gatgagcagg tactgaaggc taagaacata ggattatgtt caacagacct gacggaaggt     660
agacgaggca agttgtctat tatgagaggg aaaaagctaa aaccgtgcga ccgtgtgctg     720
ttctcagtag ggtcaacgct ctacccggaa agccgcaagc tacttaagag ctggcacctg     780
ccatcggtgt tccatttaaa gggcaaactc agcttacata gccgctgtga tacagtggtt     840
tcgtgtgagg gctacgtcgt taagagaata cgatgagcc caggcctttta tggaaaaacc     900
acagggtatg cggtaaccca ccacgcagac ggattcctga tgtgcaagac taccgacacg     960
gttgacggcg aaagagtgtc attctcggtg tgcacatacg tgccggcgac catttgtgat    1020
caaatgaccg gcatccttgc tacagaagtc acgccggagg atgcacagaa gctgttggtg    1080
gggctgaacc agagaatagt ggttaacggc agaacgcaac ggaatatgaa caccatgaaa    1140
aattatctgc ttcccgtggt cgcccaagcc ttcagtaagt gggcaaagga gtgccggaaa    1200
gacatggaag atgaaaaact cctggggggtc agagaaagaa cactgacctg ctgctgtcta    1260
tgggcattca agaagcagaa aacacacacg gtctacaaga ggcctgatac ccagtcaatt    1320
cagaaggttc aggccgagtt tgacagcttt gtggtaccga gtctgtggtc gtccgggttg    1380
tcaatccctt tgaggactag aatcaaatgg ttgttaagca aggtgccaaa aaccgacctg    1440
atcccataca gcggagacgc ccgagaagcc cgggacgcag aaaaagaagc agaggaagaa    1500
cgagaagcag aactgactcg cgaagcccta ccacctctac aggcagcaca ggaagatgtt    1560
caggtcgaaa tcgacgtgga acagcttgag gacagagcgg gcgcaggaat aatagagact    1620
ccgagaggag ctatcaaagt tactgcccaa ccaacagacc acgtcgtggg agagtacctg    1680
gtactctccc cgcagaccgt actacgtagc cagaagctca gtctgattca cgcctttggcg    1740
gagcaagtga agacgtgcac gcacaacgga cgagcaggga ggtatgcggt cgaagcgtac    1800
gacggccgag tcctagtgcc ctcaggctat gcaatctcgc ctgaagagtt ccagagtcta    1860
agcgaaagcg caacgatggt gtataacgaa agagagttcg taaacagaaa gctacaccat    1920
attgcgatgc acggaccagc cctgaacacc gacgaagagt cgtatgagct ggtgagggca    1980
gagaggacag aacacgagta cgtctacgac gtggatcaga agagatgctg taagaaggaa    2040
gaagccgcag gactggtact ggtgggcgac ttgactaatc cgcccctacca cgaattcgca    2100
tatgaagggc taaaaatccg ccctgcctgc ccatacaaaa ttgcagtcat aggagtcttc    2160
ggagtaccgg gatctggcaa gtcagctatt atcaagaacc tagttaccag gcaggacctg    2220
gtgactagcg gaaagaaaga aaactgccaa gaaatcacca ccgacgtgat gagacagaga    2280
ggtctagaga tatctgcacg tacggttgac tcgctgctct tgaatggatg caacagacca    2340
```

```
gtcgacgtgt tgtacgtaga cgaggcgttt gcgtgccact ctggaacgct acttgctttg    2400
atcgccttgg tgagaccaag gcagaaagtt gtactttgtg gtgacccgaa gcagtgcggc    2460
ttcttcaata tgatgcagat gaaagtcaac tataatcaca acatctgcac ccaagtgtac    2520
cacaaaagta tctccaggcg gtgtacactg cctgtgaccg ccattgtgtc atcgttgcat    2580
tacgaaggca aaatgcgcac tacgaatgag tacaacaagc cgattgtagt ggacactaca    2640
ggctcaacaa aacctgaccc tggagacctc gtgttaacgt gcttcagagg gtgggttaaa    2700
caactgcaaa ttgactatcg tggatacgag gtcatgacag cagccgcatc ccaagggtta    2760
accagaaaag gagtttacgc agttagacaa aaagttaatg aaaacccgct ctatgcatca    2820
acgtcagagc acgtcaacgt actcctaacg cgtacggaag gtaaactggt atggaagaca    2880
ctttccggcg acccgtggat aaagacgctg cagaacccac cgaaaggaaa cttcaaagca    2940
actattaagg agtgggaggt ggagcatgca tcaataatgg cgggcatctg cagtcaccaa    3000
atgaccttcg atacattcca aaataaagcc aacgtttgtt gggctaagag cttggtccct    3060
atcctcgaaa cagcggggat aaaactaaat gataggcagt ggtctcagat aattcaagcc    3120
ttcaaagaag acaaagcata ctcacctgaa gtagccctga tgaaatatg tacgcgcatg    3180
tatgggtgg atctagacag cgggctattt tctaaaccgt tggtgtctgt gtattacgcg    3240
gataaccact gggataatag gcctggaggg aaaatgttcg gatttaaccc cgaggcagca    3300
tccattctag aaagaaagta tccattcaca aaagggaagt ggaacatcaa caagcagatc    3360
tgcgtgacta ccaggaggat agaagacttt aaccctacca ccaacatcat accggccaac    3420
aggagactac cacactcatt agtggccgaa caccgcccag taaaggggga agaatggaa    3480
tggctggtta acaagataaa cggccaccac gtgctcctgg tcagtggcta taaccttgca    3540
ctgcctacta agagagtcac ttgggtagcg ccgttaggtg tccgcggagc ggactacaca    3600
tacaacctag agttgggtct gccagcaacg cttggtaggt atgaccttgt ggtcataaac    3660
atccacacac ttttcgcat acaccattac aacagtgcg tcgaccacgc aatgaaactg    3720
caaatgctcg ggggtgactc attgagactg ctcaaaccgg gcggctctct attgatcaga    3780
gcatatggtt acgcagatag aaccagtgaa cgagtcatct gcgtattggg acgcaagttt    3840
agatcgtcta gagcgttgaa accaccatgt gtcaccagca acactgagat gttttcctta    3900
ttcagcaact ttgacaatgg cagaaggaat tcacaactc atgtcatgaa caatcaactg    3960
aatgcagcct tcgtaggaca ggtcaccccga gcaggatgtg caccgtcgta ccgggtaaaa    4020
cgcatggaca tcgcgaagaa cgatgaagag tgcgtagtca acgccgctaa ccctcgcggg    4080
ttaccaggtg acggtgtttg caaggcagta tacaaaaaat ggccggagtc ctttaagaac    4140
agtgcaacac cagtgggaac cgcaaaaaca gttatgtgcg gtacgtatcc agtaatccac    4200
gctgttggac caaacttctc taattattcg gagtctgaag gggaccggga attggcagct    4260
gcctatcgag aagtcgcaaa ggaagtaact aggctgggag taaatagtgt agctatacct    4320
ctcctctcca caggtgtata tcaggagggg aaagacaggc tgacccagtc actgaaccac    4380
ctctttacag ccatggactc gacggatgca gacgtggtca tctactgccg cgacaaagaa    4440
tgggagaaga aaatatctga ggccatacag atgcggaccc aagtagagct gctggatgag    4500
cacatctcca tagactgcga tattgttcgc gtgcaccctg acagcagctt ggcaggcaga    4560
aaaggataca gcaccacgga aggcgcactg tactcatatc tagaagggac ccgttttcat    4620
cagacggctg tggatatggc ggagatacat actatgtggc caaagcaaac agaggccaat    4680
gagcaagtct gcctatatgc cctgggggaa agtattgaat caatcaggca gaaatgcccg    4740
```

```
gtggatgatg cagacgcatc atctcccccc aaaactgtcc cgtgcctttg ccgttacgct   4800
atgactccag aacgcgtcac ccggcttcgc atgaaccacg tcacaagcat aattgtgtgt   4860
tcttcgtttc ccctcccaaa gtacaaaata gaaggagtgc aaaaagtcaa atgctctaag   4920
gtaatgctat ttgaccacaa cgtgccatcg cgcgtaagtc caagggaata tagatcttcc   4980
caggagtctg cacaggaggc gagtacaatc acgtcactga cgcatagtca attcgaccta   5040
agcgttgatg gcgagatact gcccgtcccg tcagacctgg atgctgacgc cccagccta    5100
gaaccagcac tagacgacgg ggcgacacac acgctgccat ccacaaccgg aaaccttgcg   5160
gccgtgtctg actgggtaat gagcactgta cctgtcgcgc cgcccagaag aaggcgaggg   5220
agaaacctga ctgtgacatg tgacgagaga gaaggaaata taacacccat ggctagcgtc   5280
cgattcttta gggcagagct gtgtccggtc gtacaagaaa cagcggagac gcgtgacaca   5340
gcaatgtctc ttcaggcacc accgagtacc gccacggaac cgaatcatcc gccgatctcc   5400
ttcggagcat caagcgagac gttccccatt acatttgggg acttcaacga aggagaaatc   5460
gaaagcttgt cttctgagct actaactttc ggagacttct taccaggaga agtggatgac   5520
ttgacagaca gcgactggtc cacgtgctca gacacggacg acgagttatg actagacagg   5580
gcaggtgggt atatattctc gtcggacacc ggtccaggtc atttacaaca gaagtcagta   5640
cgccagtcag tgctgccggt gaacaccctg gaggaagtcc acgaggagaa gtgttaccca   5700
cctaagctgg atgaagcaaa ggagcaacta ttacttaaga aactccagga gagtgcatcc   5760
atggccaaca gaagcaggta tcagtcgcgc aaagtagaaa acatgaaagc agcaatcatc   5820
cagagactaa agagaggctg tagactatac ttaatgtcag accccaaa agtccctact    5880
taccggacta catatccggc gcctgtgtac tcgcctccga tcaacgtccg attgtccaat   5940
cccgagtccg cagtggcagc atgcaatgag ttcttagcta gaaactatcc aactgtctca   6000
tcataccaaa ttaccgacga gtatgatgca tatctagaca tggtggacgg gtcggagagt   6060
tgcctggacc gagcgacatt caatccgtca aaactcagga gctacccgaa acagcacgct   6120
taccacgcgc cctccatcag aagcgctgta ccgtccccat tccagaacac actacagaat   6180
gtactggcag cagccacgaa aagaaactgc aacgtcacac agatgaggga attacccact   6240
ttggactcag cagtattcaa cgtggagtgt ttcaaaaaat tcgcatgcaa ccaagaatac   6300
tgggaagaat ttgctgccag ccctattagg ataacaactg agaatttagc aacctatgtt   6360
actaaactaa aagggccaaa agcagcagcg ctattcgcaa aaacccataa tctactgcca   6420
ctacaggaag taccaatgga taggttcaca gtagatatga aaagggacgt gaaggtgact   6480
cctggtacaa agcatacaga ggaaagacct aaggtgcagg ttatacaggc ggctgaaccc   6540
ttggcgacag catacctatg tgggattcac agagagctgg ttaggaggct gaacgccgtc   6600
ctcctaccca atgtacatac actatttgac atgtctgccg aggatttcga tgccatcata   6660
gccgcacact ttaagccagg agacactgtt ttggaaacgg acatagcctc ctttgataag   6720
agccaagatg attcacttgc gcttactgct ttgatgctgt tagaggattt aggggtggat   6780
cactccctgc tggacttgat agaggctgct ttcggagaga tttccagctg tcacctaccg   6840
acaggtacgc gcttcaagtt cggcgccatg atgaaatcag gtatgttcct aactctgttc   6900
gtcaacacat tgttaaacat caccatcgcc agccgagtgc tggaagatcg tctgacaaaa   6960
tccgcgtgcg cggccttcat cggcgacgac aacataatac atggagtcgt ctccgatgaa   7020
ttgatggcag ccagatgtgc cacttggatg aacatggaag tgaagatcat agatgcagtt   7080
```

```
gtatccttga aagcccctta cttttgtgga gggtttatac tgcacgatac tgtgacagga   7140
acagcttgca gagtggcaga cccgctaaaa aggcttttta aactgggcaa accgctagcg   7200
gcaggtgacg aacaagatga agatagaaga cgagcgctgg ctgacgaagt gatcagatgg   7260
caacgaacag ggctaattga tgagctgag aaagcggtat actctaggta cgaagtgcag    7320
ggtatatcag ttgtggtaat gtccatggcc acctttgcaa gctccagatc caacttcgag   7380
aagctcagag gacccgtcat aactttgtac ggcggtccta ataggtacg cactacagct    7440
acctattttg cagaagccga cagcaagtat ctaaacacta atcagctaca atggagttca   7500
tcccaaccca aacttttac aataggaggt accagcctcg accctggact ccgcgctcta    7560
ctatccaaat catcaggccc agaccgcgcc ctcagaggca agctgggcaa cttgcccagc   7620
tgatctcagc agttaataaa ctgacaatgc gcgcggtacc ccaacagaag ccacgcagga   7680
atcggaagaa taagaagcaa agcaaaaac aacaggcgcc acaaacaac acaaatcaaa     7740
agaagcagcc acctaaaaag aaaccggctc aaaagaaaaa gaagccgggc cgcagagaga   7800
ggatgtgcat gaaaatcgaa aatgattgta ttttcgaagt caagcacgaa ggtaaggtaa   7860
caggttacgc gtgcctggtg ggggacaaag taatgaaacc agcacacgta aagggaccca   7920
tcgataacgc ggacctggcc aaactggcct ttaagcggtc atctaagtat gaccttgaat   7980
gcgcgcagat acccgtgcac atgaagtccg acgcttcgaa gttcacccat gagaaaccgg   8040
aggggtacta caactggcac cacggagcag tacaatactc aggaggccgg ttcaccatcc   8100
ctacaggtgc tggcaaacca ggggacagcg gcagacctat cttcgacaac aagggacgcg   8160
tggtggccat agtcttagga ggagctaatg aaggagcccg tacagccctc tcggtggtga   8220
cctggaataa agacattgtc actaaaatca cccccgaggg ggccgaagag tggagtcttg   8280
ccatcccagt tatgtgcctg ttggcaaaca ccacgttccc ctgctcccag ccccttgca    8340
cgccctgctg ctacgaaaag gaaccggagg aaaccctacg catgcttgag gacaacgtca   8400
tgagacctgg gtactatcag ctgctacaag catccttaac atgttctccc caccgccagc   8460
gacgcagcac caaggacaac ttcaatgtct ataaagccac aagaccatac ttagctcact   8520
gtccccgactg tggagaaggg cactcgtgcc atagtcccgt agcactagaa cgcatcagaa   8580
atgaagcgac agacgggacg ctgaaaatcc aggtctcctt gcaaatcaga ataaagacgg   8640
atgacagcca cgattggacc aagctgcgtt atatggacaa ccacatgcca gcagacgcag   8700
agagggcggg gctatttgta agaacatcag caccgtgtac gattactgga acaatgggac   8760
acttcatcct ggcccgatgt ccaaaagggg aaactctgac ggtgggattc actgacagta   8820
ggaagattag tcattcatgt acgcacccat ttcaccacga ccctcctgtg ataggtcggg   8880
aaaaattcca ttcccgaccg cagcacggta aagagctacc ttgcagcacg tacgtgcaga   8940
gcaccgccgc aactaccgag gagatagagg tacacatgcc cccagacacc cctgatcgca   9000
cattaatgtc acaacagtcc ggcaacgtaa agatcacagt caatggccag acggtgcggt   9060
acaagtgtaa ttgcggtggc tcaaatgaag gactaacaac tacagacaaa gtgattaata   9120
actgcaaggt tgatcaatgt catgccgcgg tcaccaatca caaaaagtgg cagtataact   9180
cccctctggt cccgcgtaat gctgaacttg gggaccgaaa aggaaaaatt cacatcccgt   9240
ttccgctggc aaatgtaaca tgcagggtgc ctaaagcaag gaacccacc gtgacgtacg    9300
ggaaaaacca agtcatcatg ctactgtatc ctgaccaccc aacactcctg tcctaccgga   9360
atatgggaga agaaccaaac tatcaagaag agtgggtgat gcataagaag gaagtcgtgc   9420
taaccgtgcc gactgaaggg ctcgaggtca cgtggggcaa caacgagccg tataagtatt   9480
```

-continued ggccgcagtt atctacaaac ggtacagccc atggccaccc gcatgagata attctgtatt 9540
attatgagct gtaccctact atgactgtag tagttgtgtc agtggccacg ttcatactcc 9600
tgtcgatggt gggtatggca gcggggatgt gcatgtgtgc acgacgcaga tgcatcacac 9660
cgtatgaact gacaccagga gctaccgtcc ctttcctgct tagcctaata tgctgcatca 9720
gaacagctaa agcggccaca taccaagagg ctgcgatata cctgtggaac gagcagcaac 9780
ctttgttttg gctacaagcc cttattccgc tggcagccct gattgttcta tgcaactgtc 9840
tgagactctt accatgctgc tgtaaaacgt tggctttttt agccgtaatg agcgtcggtg 9900
cccacactgt gagcgcgtac gaacacgtaa cagtgatccc gaacacggtg ggagtaccgt 9960
ataagactct agtcaataga cctggctaca gccccatggt attggagatg gaactactgt 10020
cagtcacttt ggagccaaca ctatcgcttg attacatcac gtgcgagtac aaaaccgtca 10080
tcccgtctct gtacgtgaag tgctgcggta cagcagagtg caaggacaaa aacctacctg 10140
actacagctg taaggtcttc accggcgtct acccatttat gtggggcggc gcctactgct 10200
tctgcgacgc tgaaaacacg cagttgagcg aagcacatgt ggagaagtcc gaatcatgca 10260
aaacagaatt tgcatcagca tacagggctc ataccgcatc tgcatcagct aagctccgcg 10320
tcctttacca aggaaataac atcactgtaa ctgcctatgc aaacggcgac catgccgtca 10380
cagttaagga cgccaaattc attgtggggc caatgtcttc agcctggaca cctttcgaca 10440
acaaaattgt ggtgtacaaa ggtgacgtct ataacatgga ctacccgccc tttggcgcag 10500
gaagaccagg acaatttggc gatatccaaa gtcgcacacc tgagagtgaa gacgtctatg 10560
ctaatacaca actggtactg cagagaccgg ctgcgggtac ggtacacgtg ccatactctc 10620
aggcaccatc tggctttaag tattggctaa aagaacgcgg ggcgtcactg cagcacacag 10680
caccatttgg ctgccaaata gcaacaaacc cggtaagagc ggtgaactgc gccgtaggga 10740
acatgcccat ctccatcgac ataccggaag cggccttcac tagggtcgtc gacgcgccct 10800
ctttaacgga catgtcgtgc gaggtaccag cctgcaccca ttcctcagac tttgggggcg 10860
tcgccattat taaatatgca gccagcaaga aaggcaagtg tgcggtgcat tcgatgacta 10920
acgccgtcac tattcgggaa gctgagatag aagttgaagg gaattctcag ctgcaaatct 10980
ctttctcgac ggccttagcc agcgccgaat tccgcgtaca agtctgttct acacaagtac 11040
actgtgcagc tgagtgccac cccccgaagg accacatagt caactacccg gcgtcacata 11100
ccaccctcgg ggtccaggac atctccgcta cggcgatgtc atgggtgcag aagatcacgg 11160
gaggtgtggg actggttgtt gctgttgccg cactgattct aatcgtggtg ctatgcgtgt 11220
cgttcagcag gcac 11234

<210> SEQ ID NO 21
<211> LENGTH: 34
<212> TYPE: PRT
<213> ORGANISM: Artificial Sequence
<220> FEATURE:
<223> OTHER INFORMATION: CHKVCPFP primer

<400> SEQUENCE: 21

Ala Cys Ala Gly Ala Ala Thr Thr Cys Ala Thr Ala Thr Gly Gly Ala
1 5 10 15

Gly Thr Thr Cys Ala Thr Cys Cys Cys Ala Ala Cys Cys Cys Ala Ala
20 25 30

Ala Cys

```
<210> SEQ ID NO 22
<211> LENGTH: 41
<212> TYPE: PRT
<213> ORGANISM: artificial sequence
<220> FEATURE:
<223> OTHER INFORMATION: CHKVE1RP primer

<400> SEQUENCE: 22

Ala Ala Thr Thr Gly Gly Ala Thr Cys Cys Gly Cys Gly Cys Cys
1               5                   10                  15

Gly Cys Thr Thr Ala Gly Thr Gly Cys Cys Thr Gly Cys Thr Gly Ala
                20                  25                  30

Ala Cys Gly Ala Cys Ala Cys Gly Cys
                35                  40
```

INACTIVATED CHIKUNGUNYA VIRUSES (CHIKV) COMPRISING AN E1-K211E MUTATION

FIELD OF THE INVENTION

This application is a national phase application under 35 U.S.C. §371 of International Application No. PCT/IN2012/000432, filed Jun. 18, 2012, which claims priority to Indian Patent No. 2067/CHE/2011, filed on Jun. 17, 2011; the disclosures of which are all hereby incorporated by reference herein.

The invention relates to stable immunogenic compositions for prophylaxis and treatment against any infections caused by Chikungunya Virus. The present invention particularly relates to compositions of Chikungunya virus (henceforth termed as CHIKV) strains and use of the subunit antigens of the virus thereof, for prophylaxis, therapeutic treatment and diagnosis of Chikungunya infections in humans. More particularly, the invention relates to stable immunogenic vaccine compositions for prophylaxis and treatment against any genotypes or antigenic variants or mutants of Chikungunya virus conferring an antibody titer sufficient for the seroprotection for any genotypic variant or mutant for the Chikungunya virus. The invention also relates to vaccine compositions for immunization against Chikungunya virus in combination with other bacterial and viral infections selected from the following list that include but is not limited to vaccines for Japanese encephalitis virus, dengue vaccines, West Nile virus vaccine and Chandipura virus vaccine and rabies vaccines. Combinations with other viral vaccines are also within the scope of the invention.

BACKGROUND OF THE INVENTION

Chikungunya virus (CHIKV) is an alphavirus of the family Togaviridae. It is a positive strand RNA virus that causes a generally non-fatal infection characterized by high fever and sudden onset of polyarthralgia. Hemorrhagic and neurological manifestations including seizures, lymphadenopathy, fulminant hepatitis and conjunctivitis not hitherto associated with CHIKV infections were reported since the re-surgent infection in 2005 (Sourisseau et al., 2007; Kannan et al., 2007). Phylogenetic analyses based on the partial E1 structural glycoprotein sequences have identified three CHIKV lineages, the West African, Asian and the East, Central and South African (ECSA) (Powers et al., 2000). Asian lineage circulated in India and Southeast Asia until it was replaced by the ECSA genotype, which emerged during the 2005-2006 outbreak in the Indian Ocean islands (Yergolkar et al., 2006). Sub-lineages of ECSA strains that had established locally were spread by travellers from endemic areas to Africa, Asia and Europe and caused local outbreaks (Powers and Logue, 2007).

Nearly 1.39 million suspected cases of Chikungunya virus infection occurred in India in 2006. (National Vector Borne Disease Control Programme (NVBDCP), 2007) which was caused by the ECSA strain carrying the E1-226A (Arankalle et al., 2007). The E1-A226V adaptive mutation that increases transmissibility by *Aedes albopictus* is responsible for the wide geographical spread of the virus since then (de Lamballerie et al., 2008). Host immune pressure and resultant site specific mutations in the human leukocyte antigen (HLA) class-1 restricting elements of CHIKV genome are implicated in the explosive Chikungunya virus outbreaks since 2005 (Tong et al., 2010). Prior art known in the field do not include any vaccine candidate derived from the ECSA strain. Bharat Biotech International Limited has earlier developed (disclosed in WO 2008/026225) the 2006 ECSA strain with E1-226A and its use in the development of potential vaccines against Chikungunya virus infections.

Chikungunya virus strains of the urban (epidemic) transmission cycles show a higher evolutionary rate than that of the enzootic (sylvatic) cycle, and the difference in the evolutionary dynamics between the two transmission cycles are influenced by several factors that determine virus-host interactions such as vector diversity and abundance, vector larval habitats and herd immunity in the population (Volk et al., 2010). Arboviruses like Chikungunya interacts with both the arthropod and the vertebrate hosts, and the selection pressure on the envelope glycoproteins are driven by preferences for vector adaptation and by vertebrate host immune defense mechanisms. Viral evolution tends to select for mutations in the antigenic determinants involved in neutralization as well as those residues involved in vector/host adaptation.

The vaccines under development such as that disclosed in WO 2008030220 and in Akahata et al. 2010 make use of the West African genotype and the E1-A226V isolates. Another CHIKV vaccine development is a DNA vaccine (Mallilankaraman et al., 2011) which is different in scope from that disclosed in this invention. An earlier prototype vaccine which is a live attenuated vaccine used the Asian genotype of the virus (Edelman et al., 2001). DNA vaccines have not been successful in human prophylactic vaccination so far, and live attenuated CHIKV vaccine caused side effects in human subjects (Edelman et al., 2001) who received the vaccine. The CHIKV strain used in the earlier vaccine development (WO 2008/026225) was the 2006 ECSA strain with E1-226A. The strains isolated in 2009-2010 from India as disclosed in this invention belong to a distinct sub-lineage within the ECSA lineage and carry novel mutations in the E2 and E1 envelope glycoproteins. One of the mutations in the E1 glycoprotein in all the isolates reported in the study maps to a region that determines host vector specificity and is under significant positive selection for enhanced adaptation to *Adis. aegypti*, which is the most abundant mosquito vector in the region and indeed in the tropical countries where prevalence of Chikungunya virus infection is now endemic. Other novel mutations hitherto unreported are also disclosed. Thus it is desirable to make a vaccine composition which would confer immunity to the newly developed and distinct sublineages of the ECSA strain of the Chikungunya virus which would also confer immune protection to the other mutated strains of the ECSA strain propagated by the vector *Aedis aegypti*. Inventors in this application after prolonged research disclose such an effective vaccine in this application including other additional advantages over the earlier vaccine (WO 2008/026225) such as new methods of inactivation of the virus and improved formulations with novel adjuvants that enhance the immunogenicity of the inactivated viral vaccine and the recombinant subunit vaccines and virosomes which are also included herein this invention.

OBJECT OF THE INVENTION

One object of the present invention is to provide a stable vaccine composition that is capable to prevent as well as provide treatment from infections caused by Chikungunya virus. The said vaccine composition is applicable to any genotypic variants of the Chikungunya virus for prophylaxis and treatment thereof.

Another object of the invention is to provide for a stable vaccine composition that is capable to prevent as well as provide treatment from infections caused by Chikungunya virus propagated by any suitable vector which includes prevention and treatment of Chikungunya infections propagated by the vectors *Aedis albopictus* and *Aedis aegypit* which happens to be the most commonly adaptable vectors of the Chikungunya virus.

Yet another object of the invention is to provide for a stable vaccine composition which is effective against any genotypic variants of the Chikungunya virus particularly of the ECSA strain and its particular distinct and unique sublineages as applicable thereof.

One more object of the invention is to provide for a stable vaccine composition wherein the antigenic component of the vaccine includes the whole inactivated virion or the subunit antigens of the recombinant CHIKV viral strains that can be expressed as Virus Like particles (henceforth termed as VLPs) in combination of suitable pharmaceutically acceptable carriers, stabilizers, and adjuvants.

Yet another object of the invention is to provide a method for preparation of a stable vaccine composition that is capable to elicit an immune response sufficient to prevent as well as provide treatment from infections caused by any genotypic mutants or variants of Chikungunya virus including inactivation of the CHIKV virus and mixing with adjuvants in appropriate amounts.

Another object of the invention is to provide antibodies so generated against the Chikungunya virus strains or its subunit antigens useful for diagnosis of Chikungunya virus infections in humans.

One more object of the invention relates to provide major antigenic determinants of the Chikungunya virus which are suitable as effective vaccine candidates and nucleotide and protein sequences disclosed thereof.

Yet another object of the invention includes combined vaccine compositions which are effective for prophylaxis and treatment of infections caused by Chikungunya virus and other bacterial and viral infections selected from the following list that includes but is not limited to vaccines for Japanese encephalitis virus vaccines, dengue vaccines, West Nile virus vaccine and Chandipura virus vaccine and rabies vaccines.

SUMMARY OF THE INVENTION

According to one aspect of the invention, the invention includes vaccine compositions which specifically contain the whole inactivated virion or the subunit antigens of the CHIKV virus strains. The compositions of the present invention more particularly relate to vaccine capable of eliciting protective antibody and strong T cell responses against Chikungunya virus infection.

Another aspect of the invention is to provide inactivated recombinant CHIKV vaccines along with appropriate adjuvants that offer high protective efficacy.

Yet another aspect of the invention of the present invention more particularly relate to vaccine capable of eliciting protective antibody and strong T cell responses against Chikungunya virus infections.

One another aspect of the invention relate to methods of preparing and using Chikungunya virus (CHIKV) antigens of defined sequences expressed as recombinant proteins, virus like particles and as virosomes which are used to elicit protective immune response. The potency of such subunit vaccines are comparable to that elicited by the vaccine consisting of whole inactivated virion of CHIKV that are inactivated with reagents under conditions that confer high immunogenicity to the vaccine.

Another aspect of the invention relates to methods of inactivation of the virus which comprises heat, gamma irradiation, ultraviolet light or chemically inactivated whole virion of Chikungunya virus isolates in a stable formulation. A combination of two or more inactivating agents has also been used with similar effect. The virus isolates disclosed in the invention are used in vaccine development, and all the methods are applicable to any genotypes or genotypic variants/serotypes/strains/mutants of Chikungunya virus.

One another aspect of the invention is to provide vaccine compositions against Chikungunya virus that elicit strong immunological response when administered parenterally, preferably intradermally, intramuscularly or sub-cutaneously in mammals preferably in humans, and are effective when administered mucosally and by other routes such as oral routes.

Yet another object of the invention is to provide antibodies against Chikungunya virus or the subunit antigens thereof to be used for treatment and diagnosis of Chikungunya virus infections in mammals, preferably humans.

One another aspect of the invention is to provide a composition for eliciting protective antibody and strong T cell responses either singly or in combination with other vaccines included within the scope of the invention. The other vaccines in combination are but not limited to vaccines for Japanese encephalitis virus vaccines, dengue vaccines, West Nile virus vaccine and Chandipura virus vaccine and rabies vaccines.

BRIEF DESCRIPTION OF THE DRAWINGS

FIG. 1:

Figure 2:
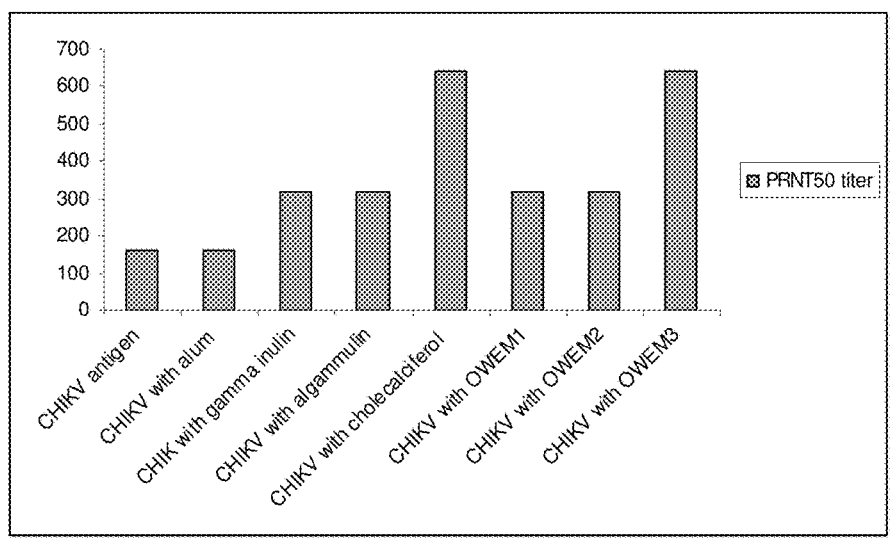

Immunogenicity of CHIKV whole virion antigen inactivated by several inactivation methods were tested for potency. The details of inactivation procedures are provided in Example 2. Potency of the 15 µg of the inactivated viral vaccine was tested in three intramuscular injections in 4-6 week old Balb/c mice (8 nos per group) at intervals of 0, 7 and 21 days and bled 7 days after the last dose administration. Only a single dose of the live virus was administered for comparison. The potency of the vaccine preparations were tested by estimating the titer of neutralizing antibodies by $PRNT_{50}$.

FIG. 2:

Immunogenicity of the CHIKV vaccine preparation with and without adjuvants was tested in three intramuscular injections in 4-6 week old Balb/c mice (8 nos per group) at intervals of 0, 7 and 21 days and bled 7 days after the last dose administration. The composition of the adjuvanted vaccine formulations are provided in Example 5. The potency of the vaccine preparations were tested by estimating the titer of neutralizing antibodies by $PRNT_{50}$.

DETAILED DESCRIPTION OF THE INVENTION

No detailed study on evolution of CHIKV serotypes due to sequence diversity has been reported. We report for the first time the adaptive evolution of ECSA strains of CHIKV to *Ae. aegypti* as found in the 2009-2010 virus isolates from India. Incidentally, *Ae. aegypti* is the most prevalent vector in India and indeed in several tropical countries. Despite unique mutations in isolates reported in the current invention, the virus strains cross neutralize the Asian genotypes and various ECSA sub-lineages of CHIKV indicating that they are good candidates for vaccine development. Using virus strains or antigens derived from such strains thereof, that are better adapted to the most prevalent vector in the region is important for vaccine development rather than using strains of West African or Asian genotype which are not so widely prevalent now than the ECSA genotype. Even among the ECSA genotype, using candidates such as LR2006 isolates from Reunion Island that carry E1-A226V mutation which is an adaptive mutation to increase transmissibility in Ae. albopictus is less advantageous as Ae. albopictus vector in India is prevalent widely only along the West coast of India such as in the states of Kerala and South coastal Karnataka, whereas the mosquito vector that is most abundant in the rest of the country is Ae. aegypti. The virus strains isolated and reported in this invention are unique in that they show adaptive evolution to Ae. aegypti and at the same time also infect Ae. albopictus. Apart from the unique mutations that increase adaptation to Aedes aegypti, the advantage of the invention is that the virus isolates cross neutralize the Asian genotypes and various ECSA variant strains and hence are good candidate vaccines. Hence, a subunit vaccine derived from the virus antigens or recombinant antigens of these isolates are good vaccine candidates as well, as the recombinant vaccine antisera also cross neutralizes the different genotypes and genotypic variants.

Hence, using the Indian virus strains that show unique adaptation to Ae. aegypti and also infects Ae. albopictus is advantageous than using the West African, Asian or ECSA E1-226A and other variant strains as Ae. aegypti is the most widely prevalent vector in the India which has the highest incidence of CHIKV infection in the world.

The Chikungunya virus isolates within the scope of the invention are those that belong to the ECSA (East, Central and South African) genotype whose structural polyprotein sequence comprises of the capsid, E3, E2, 6K and E1 (C-E3-E2-6K-E1) proteins. The isolates obtained from the Indian epidemic of 2009-2010 are unique in the sequence reported so far. The structural polyprotein sequence comprising the C-E3-E2-6K-E1 proteins have been deposited in the public sequence repository (GenBank) on 27 Apr. 2010 and have been assigned the accession numbers HM159385 to HM159390. The sequences were published in March 2012 after the date of filing the provisional patent. The unique nucleotide sequences reported in this invention are SEQ ID NO. 1 (isolate TN01610), SEQ ID NO. 2 (isolate TN15110) SEQ ID NO. 3 (isolate TN06210), SEQ ID NO. 4 (TN06310), SEQ ID NO. 5 (TN06410) and SEQ ID NO. 6 (AP0109), whose corresponding protein sequences when translated are SEQ ID NO. 8, SEQ ID NO. 9, SEQ ID NO. 10, SEQ ID NO. 11, SEQ ID NO. 12 and SEQ ID NO. 13 respectively. The CHIKV strain CHIKV/03/06 has structural polyprotein of SEQ ID NO. 7 and was isolated during the 2006 Indian epidemic, the corresponding protein sequence is SEQ ID NO. 14. The names of the virus isolates are provided in the brackets. The full length genomic RNA sequences of the above mentioned virus isolates of the current invention are provided in SEQ ID NO. 15 to SEQ ID NO. 20.

The sequence of the isolates disclosed in the invention have unique genetic signatures such as the combination of T1766C (E2-V264A)+A3058G (E1-K211E)+3104C (E1-226A) in the structural polyprotein sequence in addition to other amino acid changes when compared to the S27 African prototype (Gen Bank Acc No. AF369024). The position of nucleotide substitution in the structural polyprotein and the corresponding amino acid change in the individual proteins within the polyprotein is indicated in brackets. Other unique mutations that are being reported are Capsid-A232V in TN06310, E3-D40N in TN15110, E2-K47N in TN06210, E2-G55R in TN01610 and AP0109, E2-K66E in TN064110, E1-P58L in AP0109, and E1-G195R in TN15110 and TN06310. Codon by codon analyses by maximum likelihood estimates of 'ω' (the ratio of non-synonymous to synonymous substitutions) of the ECSA strains show that the amino acid mutation E1-K211E in the isolates reported in the invention (of SEQ ID NO. 8 to SEQ ID NO. 13) is under significant positive selection (posterior probability of ≥0.97; p<0.05) and is suggestive of adaptive mutation to increase infectivity in the Aedes mosquito vectors, particularly in Aedes aegypti. The amino acid residue E1-211E is conserved in the Asian genotypes of CHIKV which are circulated by Ae. aegypti. Additional mutations disclosed in this invention such as the three novel mutations E2-K47N, E2-G55R and E2-K66E also cluster in the same region of the E2 protein that are reported to increase the infectivity of the Sindbis virus in Aedes aegypti. The E2 aa 52-82 region is exposed at the top of the spike, which is the point of contact with cellular receptors. Codon by codon maximum likelihood estimates of 'ω' by SLAC (Single Likelihood Ancestor Counting), eFEL (Fixed Effects Likelihood), iFEL (internal Fixed Effects Likelihood) and REL (Random Effects Likelihood) identified amino acid sites across the capsid and the structural glycoproteins under significant purifying selection. Among the amino acid sites that were negatively selected, the E2-199Y residue was selected as the genetic loci under most significant purifying selection by all the four likelihood estimates (posterior probability >0.99 by REL, p<0.01 by iFEL, p=0.001 by SLAC and p=0.00 by eFEL). E2-199Y is an important residue in Chikungunya virus determining virus fitness in mosquitoes.

Viral evolution tends to select for mutations in the antigenic determinants involved in neutralization as well as those residues involved in vector/host adaptation. Because of its high immunological specificity, the serum neutralization test is often the gold standard against which the specificity of the other serological techniques is evaluated. The antisera raised against the virus isolates reported in the invention neutralized the virus isolates of Asian and ECSA lineages and several variant strains of ECSA genotype including the E1-A226V ECSA variant strain, indicating that they are good vaccine candidates as they have broad neutralizing activity.

The properties of Chikungunya virus particles as an immunogen, adaptation and propagation of the virus in host cell lines to a high titer, determination of the identity of the virus by RT-PCR, methods of purification and inactivation of the virus, preparation of stable vaccine formulation in a pharmaceutically acceptable carrier suitable for administration in humans, the viral assays and tests for vaccine potency in animal models are also within the scope of the invention. The virus particles obtained from infected patients or isolated from the vectors of the virus where the virus resides, are adapted in cell lines and propagated in vitro in cell culture in several passages.

The use of the CHIKV strains in the development of an inactivated whole virion vaccine is one aspect of the invention. The Chikungunya virus strains were infected in mammalian cell lines for production of the virions. The mammalian cells include but are not limited to Vero cells (ATCC CCL-81), MRC-5 or any other cell line suitable for vaccine production for human use.

The whole virions obtained from cell culture were inactivated with different inactivating agents. The optimum time, temperature and use of stabilizers such as sugars like sucrose, lactose, trehalose and other sugars and sugar combinations, and the addition of sugar alcohols such as mannitol or sorbitol either alone or in combination with different sugars, addition of human serum albumin either alone or in combination with sugars, amino acids and sugar alcohols during the inactivation process are within the scope of the invention. The virus was rendered non-infectious by inactivating either by heat, gamma irradiation or ultra violet light or by chemical means with formalin and beta-propiolactone (BPL) among others under conditions that retained high immunogenicity of the vaccine preparation. The conditions of virus inactivation were optimized and are presented in Example 2. Chemical inactivating agents are selected from the following list which includes but is not limited to: formalin, beta-propiolactone, glutaraldehyde, N-acetylethyleneimine, binary ethyleneimine, tertiary ethyleneimine, ascorbic acid, caprylic acid, psolarens, detergents including non-ionic detergents etc. is added to a virus suspension to inactivate the virus. The concentration of the sugars, sugar alcohols, human serum albumin and amino acids either when used alone or in various combinations were in the concentration range of 0.01% to 20%, preferably 0.1% to 10% and most preferably 0.1% to 5%. Time and temperature of inactivation in the presence of the stabilizers were optimized from 2-8° C. to 37° C. for varying period of time such as 30 min to 20 days. Such vaccine formulations were highly immunogenic and elicited protective neutralizing antibodies.

The structural glycoproteins C-E3-E2-6K-E1 of the Chikungunya virus are the major antigenic determinants. Hence, the structural glycoproteins are excellent vaccine candidates for subunit vaccine for prophylaxis of CHIKV infections. The sequence of the structural proteins as defined in SEQ ID NO. 8 to SEQ ID NO. 14. The recombinant non-structural proteins are also immunogenic and are good candidate vaccines. The eukaryotic expression system of choice includes mammalian cells, baculovirus in insect cells, and yeast cells of any species, most preferably *Pichia pastoris* or *Saccharomyces cerevisiae*. Genes encoding the subunit antigens were also expressed in prokaryotic cells such as *E. coli* using any of the suitable prokaryotic expression vectors. *Pichia pastoris* as recombinant expression host is advantageous at industrial scale as it is cost effective for large scale manufacture compared to other eukaryotic expression systems. Recombinant proteins derived from *Pichia pastoris* have been successfully commercialized and have been found safe for human use. The structural proteins such as C-E3-E2-6K-E1 of the sequences disclosed in this application are capable of assembling into 'virus like particles' (VLPs). Alternatively, the VLPs contain only the E3-E2-6K-E1 or E2-6K-E1 or only E2-E1 proteins and are immunogenic and elicited protective immune response when administered in animals. The subunit antigens comprising E3-E2-6K-E1 or E2-6K-E1 are also capable of assembling into virosomes as CHIKV is an enveloped virus. Virosomes comprising E3-E2-6K-E1 or E2-6K-E1 or only E2-E1 are also immunogenic. The liposomes and virosomes can contain different combination of lipid soluble substances which include but are not limited to cholecalciferol, cholesterol, phospholipids etc. and the viral envelope proteins. The methods for virosomes preparation such as solubilization of the virus particles with detergents or with short chain phospholipids and reconstitution of the envelope proteins after removal of the chaotropic agents and the non-envelope proteins and RNA that are applicable to any enveloped virus are also applicable to CHIKV.

Purification of the virus was achieved by physical or chemical means and preferably by a combination of both. Physical methods utilize the physical properties of the virus such as density, size, mass, sedimentation coefficient etc. and include any of the following techniques but are not limited to: ultracentrifugation, density gradient centrifugation, ultrafiltration etc. Purification through chemical means employs methods such as adsorption/desorption through chemical or physiochemical reactions such as ion exchange chromatography, affinity chromatography, hydrophobic interaction chromatography, gel filtration chromatography, hydroxyapatite matrix, salting with inorganic salts one such example being ammonium sulphate, and by the use of proprietary Himax™ technology, organic salts and organic compounds such as polyethylene glycol. Purification of the virus or the recombinant virus antigens was achieved by either one or a combination of two or more of the above mentioned methods.

The antigenic compositions of the above mentioned CHIKV candidate vaccines, such as the inactivated whole virion vaccines or the recombinant vaccines were formulated in pharmaceutically acceptable carrier for immunization in mammals, preferably humans. The Chikungunya virus vaccine formulation was adjuvanted and adjuvants were selected from the following list, which includes but is not limited to: alum; calcium phosphate; inulin of any polymorphic form, preferably gamma inulin; adjuvants containing inulin in combination with other organic and inorganic compounds such as aluminum hydroxide, aluminum phosphate, aluminum sulphate phosphate and calcium phosphate; liposomes, chitosan and complex carbohydrates such as dextran, dextrins, starch, inulin, mannans and glucomannans, galactomannans, beta-glucans, heparin, cellulose, pectins and pectinates, lectins and any other carbohydrates either synthetic or derived from any source, any biodegradable and biocompatible polymers, such as poly lactide and poly(lactide co-glycolides; PLG) or PLGA; any emulsions including but not limited to oil in water emulsions one such example being ASO3, other squalene based adjuvants such as MF59 etc., any water in oil emulsion; liposomes prepared with cholecalciferol as one of the ingredients along with other lipid soluble compounds; liposomes of other compositions; RIBI adjuvant systems, saponins including but not limited to QS-21, QuilA, tomatine, ISCOMs, ISCOMATRIX etc, lipopeptides, glycopeptides, lipopolysaccharides, muramyl dipeptides and any peptide based adjuvants, oligonucleotides, any TLR ligands as adjuvants, any cytokine, vitamins and non-toxic bacterial toxins etc. The most compatible and cost effective adjuvant was selected in the final vaccine formulation after testing for immunogenicity which was enhanced by the addition of adjuvants. In addition to the above, any other organic and inorganic substances that have good immunopotentiating activity can also be used as adjuvants either singly or in combinations to enhance the immunogenicity of Chikungunya virus vaccines. In addition to the inactivated whole virion vaccine, the aforementioned adjuvants or adjuvant combinations are also effective with recombinant Chikungunya virus vaccine using recombinant subunit antigens either when presented as virosome, virus like particles (VLPs) or when expressed, purified and formulated as individual recombinant proteins. The use of suitable adjuvants in the vaccine formulations reduces the amount of antigen required and helps in the manufacture of low-cost vaccines thus conferring economic advantage.

The buffer used in the formulations is phosphate or phosphate-citrate buffer or any other pharmaceutically acceptable buffer. The vaccines optionally contain preservative(s), stabilizer(s) etc. The excipients were selected from a list that includes but is not limited to reducing and non-reducing sugars, sugar alcohols such sorbitol and mannitol, glycerol, amino acids, human serum albumin, inulin, thiomerosol and a choice of adjuvant from the aforementioned list of adjuvants. The excipients are added in the range of 0.01% to 20% for the liquid formulation and upto 60% of the total solids for a lyophilized formulation. The vaccine formulations were also presented as emulsions, either as water in oil emulsion or as oil in water emulsion. Such emulsions of vaccine antigens contain preservatives and stabilizers and other adjuvants. Such a stable formulation of the immunogen either in a liquid or in a lyophilized form and after reconstitution in a pharmaceutically acceptable buffer or water is suitable for administration parenterally in human host and is also formulated for mucosal administration. The vaccine formulations were highly immunogenic and neutralized homologous and heterologous CHIKV strains.

For potency testing of the vaccine, the vaccine formulations were tested in Balb/c mice and rabbits. The resultant serum is assayed by in vitro neutralization tests and the antibody titer is determined by ELISA. Seroconversion was observed in the animals immunized with the vaccine formulations described in the present invention. Efficacy of the recombinant vaccine in offering a protective immune response was comparable with the whole virion vaccine and the titers of the neutralizing antibody responses were determined by either serum neutralization test (SNT), plaque reduction neutralization test ($PRNT_{50}$) and ELISA among other methods. Passive immunization of the vaccine antibody offered good protection against virus infection indicating therapeutic use of CHIKV antibodies. The presence of virus in infected patients samples were accurately determined using CHIKV antibodies. Chikungunya virus vaccine obtained by the methods included in the scope of the current invention elicits strong neutralizing antibodies in combination with other vaccines. The vaccines that can be included in the combination are selected from the following list that includes but is not limited to vaccines for Japanese encephalitis virus, Dengue vaccines, West Nile virus vaccine and Chandipura virus vaccine and rabies vaccines. Combinations with other viral vaccines are also within the scope of the invention. As known to those skilled in the art, a bivalent or polyvalent vaccine can be prepared by mixing vaccines produced from two or more CHIKV strains, and is mixed in a suitable ratio based on the antigen content. Such mixing provides a vaccine preparation having a broad antigenic spectrum for protection against the infection.

According to the present invention, the methods and compositions of CHIKV strains of the current invention is applicable to any CHIKV strain. The vaccines of this invention offered good immune protection against plural strains of CHIKV in addition to the virus strains used in production of the vaccine. The CHIKV isolates reported in the study have broad neutralizing activity as they cross neutralize different genotypes/genotypic variants/strains of CHIKV and are ideal vaccine candidates for development of whole inactivated virion vaccine or recombinant vaccines comprising the antigens derived from these virus isolates. The methods disclosed in the invention are applicable to any genotype/genotypic variants/serotype/strain of Chikungunya virus and as demonstrated offer good cross protection against multiple gentotypes/genotypic variants of the virus.

The invention is further described in the following examples. It should be noted that features, integers, characteristics, ranges, compounds, and/or groups described in conjunction with a particular aspect, embodiment or example of the invention are to be understood to be applicable to any other aspect, embodiment or example described herein unless incompatible therewith and should be considered within the scope of the invention.

Example 1

Isolation of Virus Strains

The virus strains were isolated from blood samples collected from febrile patients with their informed consent during an epidemic outbreak in India in 2009-2010. The blood samples were collected during the acute phase of Chikungunya virus infection when patients reported high fever, acute polyarthralgia and painful swelling in joints and rashes. The patients' sera samples were transported on dry ice to the laboratory. About 0.05 ml of the serum was used for infection of Vero cells (ATCC No. CCL-81) in $25^2$ cm flask in medium containing DMEM (Dulbecco's Modified Eagle Medium; Sigma—Aldrich Catalog #D5523) containing 1% fetal bovine serum (FBS). The flasks were incubated at 34° C. to 37° C. The virus was harvested 48 hours after infection. Scaled up cultures of the virus were made in cell stacks or in cell factories or in bioreactors in liquid culture All the blood samples were negative for Dengue infection by specific IgM ELISA (National Institute of Virology, Pune). The infectious titer of the virus increased more than 10 fold after the virus particles were passaged once in suckling mice brain or after passage in mosquito cell lines such as C6/36 cells, and also after repeated passage of the virus in cell culture in vitro.

Example 2

Purification and Inactivation of CHIKV Virus

The two virus isolates TN01610 and TN15110 were purified from the infected Vero cell monolayers from scaled up cultures by initial ultrafiltration to remove cellular debris, and by filtration and concentration through a 300 kD membrane followed by purification by ion exchange and gel filtration column chromatography. Heat inactivation of the virus was carried out at different temperatures ranging from 45° C. to 60° C. for 30 min to 4 hrs and optimally at 56° C. for 30 min. Inactivation by ultraviolet (UV) light was done at 254 nm for varying period of time from 30-120 min on ice, and optimally for 40 min. Chikungunya virus was inactivated effectively by formalin at ratios upto 1:3000 for formalin:virus at 2° C. -8° C. upto 7 days, and with beta propiolactone at 1:1000 to 1:2500 (beta propiolactone:virus) for upto 7 days at 2° C.-8° C. In both the cases, the time of inactivation was reduced to 24-48 hrs when carried out at ambient temperatures of +20-25° C. Formalin and beta propiolactone were removed by dialysis. During inactivation, use of additives such as glycine, mannitol, sorbitol and sugars and sugar combinations increased the stability of the vaccine preparation. The sugars used may be selected from sucrose, lactose, trehalose, maltose at varying concentrations from 0.5% to 5%. Inactivation of the virus by gamma irradiation was carried out by exposure of the virus samples to a dose of 10 kGy (Kilo Gray) to 25 kGy from a $^{60}Co$ source (Ms. Gamma Agro-Medical Processings Pvt. Ltd. Hyderabad) and optimally to 20 kGy. Complete inactivation of the virus samples by all of the above methods were confirmed by three serial passages in Vero cells for absence of virus cytopathic effect, and additionally by the absence of growth abnormalities and death when inoculated by intracerebral route in the brain of 2-day old mice. The inactivated virus antigens were tested for potency as candidate vaccines.

Example 3

Reverse Transcriptase—Polymerase Chain Reaction (RT-PCR) and Sequencing

Viral RNA was isolated using Absolutely RNA Miniprep kit (Stratagene, La Jolla, Calif.) from infected Vero cells (ATCC CCL-81), after a single passage. RT-PCR was carried out using the AccuScript High Fidelity 1$^{st}$ Strand cDNA Synthesis Kit (Stratagene) as per the kit protocols, and the 3,747 bp structural polyprotein gene was amplified with the PfuUltra High-Fidelity DNA polymerase (Stratagene). PCR primers were designed based on the consensus sequence of the S27-African prototype (AF369024) and the Indian 2006 isolate (HM159384), and used to amplify overlapping sequences of the structural polyprotein gene. PCR reaction consisted of initial denaturation at 95° C. for 1 min, followed by 32 thermal cycling steps at 94° C. for 40 sec, annealing at 52-65° C. (depending on the primer sets) for 30 sec and extension at 70° C. for 3 min, followed by final extension at 70° C. for 10 min. PCR products were purified by QIAquick gel extraction kit (QIAGEN, Hilden, Germany) after separation on 1% agarose gel and used for DNA sequencing. Nucleotide sequencing of CHIKV structural polyprotein gene gel purified PCR products were sequenced on both strands of DNA by BigDye terminator v3.1 reaction (Applied Biosystems, Foster City, Calif.) and the sequence data was analyzed using Sequencher v4.7 (GeneCodes, Ann Arbor, Mich.). The sequences were deposited in GenBank on 27 Apr. 2010 before filing the provisional patent and published by GenBank on 2 Mar. 2012. The unique nucleotide sequences reported in this invention are SEQ ID NO. 1 (isolate TN01610), SEQ ID NO. 2 (isolate TN15110) SEQ ID NO. 3 (isolate TN06210), SEQ ID NO. 4 (TN06310), SEQ ID NO. 5 (TN06410) and SEQ ID NO. 6 (AP0109), whose corresponding protein sequences when translated are SEQ ID NO. 8, SEQ ID NO. 9, SEQ ID NO. 10, SEQ ID NO. 11, SEQ ID NO. 12 and SEQ ID NO. 13 respectively. The CHIKV strain CHIKV/03/06 has structural polyprotein gene of sequence SEQ ID NO. 7 and was isolated during the 2006 Indian epidemic and its corresponding protein sequence is SEQ ID NO. 14. The names of the virus isolates are provided in the brackets. For complete genomic RNA sequences, the sequencing reactions were performed using sequencing by synthesis (SBS) technology on the Illumina GAIIx (Genotypic Technology Pvt. Ltd. Bangalore). The complete nucleotide sequences (in the form of cDNA) of the virus genomic RNA of the above mentioned virus strains are provided in SEQ ID NO. 15 to SEQ ID NO. 20. Mutations identified with reference to strain S27-African prototype (AF369024) were mapped to the individual structural proteins and are presented in Table 1.

TABLE I

| Unique mutations in the Chikungunya virus structural genes reported in this study. | | | | | | | | | | |
|---|---|---|---|---|---|---|---|---|---|---|
| Amino acid position | | Nucleotide | strain S27- | | | | | | | |
| Polypeptide | Protein | change in polypeptide | African prototype | CHIKV/03/06 | TN01610 | TN151100 | TN06210 | TN06310 | TN06410 | AP0109 |
| 232 | C-232 | c695t | A | . | . | . | . | . | V | . | . |
| 301 | E3-40 | g901a | D | . | . | . | N | . | . | . | . |
| 372 | E2-47 | a1116t | K | . | . | . | . | N | . | . | . |
| 380 | E2-55 | g1138a | G | . | R | . | . | . | . | . | R |
| 391 | E2-66 | a1171g | K | . | . | . | . | . | . | E | . |
| 589 | E2-264 | t1766c | V | . | A | A | A | A | A | . |
| 867 | E1-58 | c2600t | P | . | . | . | . | . | . | L |
| 1004 | E1-195 | g3010c | G | . | . | R | . | R | . | . |
| 1020 | E1-211 | a3058g | K | . | E | E | E | E | E | E |

Unique mutations identified in the capsid, E1, E2 and the E3 structural glycoproteins in the 2009-2010 CHIKV isolates from the States of Tamil Nadu and Andhra Pradesh.
"." Amino acids identical to the reference strain S27-African prototype (AF369024). The GenBank accession numbers of the isolates from Tamil Nadu are HM159385 (TN01610), HM159386 (TN15110), HM159387 (TN06210), HM159388 (TN06310), HM159389 (TN06410), and from Hyderabad, Andhra Pradesh are HM159384 (CHIKV/03/06) and HM159390 (AP0109).

Example 4

Phylogenetic Analyses and Inference of Selection Pressure

The sequences reported in this study and those retrieved from GenBank were screened for recombination by the Genetic Algorithm Recombination Detection (GARD) (Kosakovsky Pond et al. 2006) prior to phylogenetic analysis. Evolutionary analyses were performed in MEGA5 (Tamura et al. 2007) using Kimura-2 parameter model of nucleotide substitution with 1000 bootstrap replicates. Multiple sequence alignment was performed using ClustalW2.0.3. The ECSA structural polyprotein sequences from 2005-2010 retrieved from GenBank and those reported in the study were used in the inference of selection pressure on the ECSA lineage. About 52 unique sequences were short listed by Hyphy (Pond et al. 2005) from 58 sequences retrieved from GenBank for the analyses. Codon-based Maximum Likelihood estimates of $\omega$ or the dN/dS (the ratio of non-synonymous to synonymous substitutions) were inferred by Random Effects Likelihood (REL), Fixed Effects Likelihood (eFEL) and selection along the internal branches of phylogeny was tested using Internal Fixed Effects Likelihood (iFEL) method in HyPhy. In the likelihood methods, positive selection was inferred as significant if the p value of the likelihood ratio test (LRT) was less than 0.05 or when the Bayes factor was equal to or larger than 100 for a site. Statistical testing of positive selection operating on the entire protein was inferred by Single Likelihood Ancestor Counting (SLAC) method in HyPhy. Inference of $\omega$ by empirical Bayesian method using LRT (Likelihood Ratio Test) with the MEC (Mechanistic Empirical Combination) model for positive selection, and M8a model for purifying and neutral selection was carried out using Selection v2.2

(Stern et al. 2007). The amino acid sites of CHIKV structural proteins under significant positive and purifying selection is provided in accompanying Table II.

TABLE II

Amino acid sites of CHIKV structural proteins under significant positive and purifying selection

| Method | Codon no. in structural polyprotein | Positively selected amino acid | Negatively selected amino acid | p-value | Posterior probability | Bayes factor† |
|---|---|---|---|---|---|---|
| REL | 523 | E2-198R | | | 0.87 | 111.55 |
| | 524 | | E2-199Y | | 0.999 | 505.10 |
| | 645 | E2-320T | | | 0.86 | 100.71 |
| | 711 | E2-386A | | | 0.87 | 108.86 |
| | 1020 | E1-211K | | | 0.97 | 532.15 |
| | 1035 | E1-226A | | | 0.98 | 773.33 |
| | 1078 | E1-269V | | | 0.86 | 100.10 |
| | 1113 | E1-304P | | | 0.88 | 120.58 |
| iFEL | 28 | | C-28I | 0.034 | | |
| | 273 | | E3-12N | 0.008 | | |
| | 326 | | E2-1S | 0.036 | | |
| | 397 | | E2-72N | 0.008 | | |
| | 524 | | E2-199Y | 0.003 | | |
| | 834 | | E1-25S | 0.036 | | |
| | 909 | | E1-100N | 0.005 | | |
| | 916 | | E1-107H | 0.016 | | |
| | 1020 | E1-211K | | 0.040 | | |
| | 1035 | E1-226A | | 0.006 | | |
| | 1120 | | E1-311D | 0.042 | | |
| | 1245 | | E1-436F | 0.009 | | |

The amino acids under positive selection in the capsid (C) and in the E1, E2 and E3 glycoproteins in the 2009-2010 Indian CHIKV isolates were inferred by Random Effects Likelihood (REL) and by Internal Fixed Effects Likelihood (iFEL) methods using the HyPhy package. The amino acid sites under significant positive and purifying selection in the E1 and E2 proteins respectively (Bayes factor >500, posterior probability ≥0.97 and p<0.05) are indicated in boldface.
†Bayes factor is statistical estimation of posterior odds/prior odds for positive selection (dN>dS) at the site.

Example 5

Cloning and Expression of the Structural Polyprotein Sequences

The virus isolates reported in this patent was used as the source for cloning and expression of all viral antigens. The complete open reading frame of the Chikungunya virus structural polyprotein encoded by the SEQ ID NO.1 was amplified by RT-PCR of the viral genomic 15RNA using the primers CHKVCPFP as the forward primer and CHKVE1RP as the reverse primer to obtain a ~3747 bp PCR fragment. The sequence of the PCR primers used for PCR amplification is:

```
CHKVCPFP:
                                           (SEQ ID NO: 21)
55' ACAGAATTCATATGGAGTTCATCCCAACCCAAAC 3'

CHKVE1RP:
                                           (SEQ ID NO: 22)
5' AATTGGATCCGCGGCCGCTTAGTGCCTGCTGAACGACACGC 3'
```

The PCR fragment was digested with Nde1 and BamH1 and cloned into the Nde1 and BamH1 sites of the prokaryotic expression vector, pET-11B and the recombinant plasmid containing the insert was transformed in E.coli DH5a. The recombinant plasmid DNA isolated from DH5a was used to transform the E.coli strain BL21 (DE3). The PCR gene fragment was digested with EcoR1 and Not 1, gel purified by standard protocols and cloned into EcoR1 and Not1 sites of the yeast expression vector pPIC3.5K (Invitrogen Corporation, Carlsbad, USA) and transformed in E.coli DH5a. Recombinant plasmid DNA isolated from E.coli clone was linearized with Bg1II and was transformed into Pichia Pastoris GS115 as per the protocol from manufacturers (Invitrogen). The gene has been cloned into the AOX1 locus and expressed under the AOX1 promoter by methanol induction. The cloning, screening, isolation of the recombinant Pichia strains and induction of the cloned gene with methanol were carried out as per the User's manual "A Manual of Methods for Expression of Recombinant Proteins in Pichia pastoris" Version M Jan 2002, of Pichia Expression Kit, Catalog # K1710-01, Invitrogen Corporation, Carlsbad, USA).

Example 6

In Vivo Potency Testing of the Vaccine Formulations

The inactivated virus sample in vaccine formulations was tested with different adjuvants for potency. The adjuvants tested (at concentrations per single human dose) include a) aluminum hydroxide (0.5 mg aluminum content) b) aluminum phosphate (0.5 mg aluminum content) c) gamma inulin (10 mg), d) algammulin (a combination of aluminum hydroxide and gamma inulin) at 10 mg, e) cholecalciferol in oil at 0.75 mg per dose, f) an oil in water emulsion OWEM1, containing 4.3% squalene, 0.5% tween-80, and 0.5% Span-85 (Sigma Aldrich product # S7135) in 10 mM phosphate-citrate buffer, f) oil in water emulsion OWEM2 containing 9.5 mg squalene, 1 mg tween-80, 1 mg Span-85, 11 mg alpha tocopherol in phosphate-citrate buffer, g) an oil in water emulsion OWEM3 containing at the same concentration of excipients as in OWEM2 except that alpha tocopherol is replaced with 1-10 mg cholecalciferol. The formulated and adjuvanted vaccine preparations were injected intramuscularly in mice and booster doses were administered on day 7 and day 21 after administration of the first dose. Blood was collected at 28 days after the first dose was administered. Pooled sera from each test group were complement inactivated at 56° C. for about 30 min. All the formulations contained 15 µg viral antigen in 40 mM phosphate buffer, pH 6.8-7.2 containing 150 mM NaCl. Sera samples were used for estimation of neutralizing antibodies and for the estimation antibody titer by ELISA. Vaccinated animals offered complete protection against viremia with a virus challenge dose of $10^{4.5}$ pfu/ml when monitored over a period of 72 hours after intravenous/intraperitoneal administration of the challenge virus. In another experiment, passive immunization with rabbit antisera with $PRNT_{50}$ titer of 640 when administered intravenously in 4-6 week old Balb/c mice offered complete protection against viremia when challenged with $10^{4.5}$ pfu/ml of the challenge virus. For serotype analyses, antisera against CHIKV/03/06 neutralized heterotypic virus isolates of the Asian genotype (GenBank Acc No. EF027140, isolated in Kolkata in 1963), ECSA, (E1-A226V, E1-211K, GenBank Acc No. FJ000069, isolated in Kerala in 2007) and ECSA (E1-226A, E1-K211E, GenBank Acc No.

HM159386, obtained from Tamil Nadu in 2010 with neutralizing antibody titer ≥40 indicating heterotypic protection against genotypic variants, and also indicating that no distinct serotypes have evolved.

Example 7

Plaque Reduction Neutralization Assay

One day prior to the assay 6-well plates were seeded with $2.5 \times 10^3$ Vero cells (ATCC CCL-81) per well and the plates were incubated at 37° C. in a 5% $CO_2$ incubator. To 4-fold dilutions of the sera samples in MEM containing 2% fetal bovine serum, equal volume of the standardized virus ($10^5$ pfu/ml) was added and incubated at 37° C. with 5% $CO_2$ for 90 min. The cells were washed twice with 1×PBS pH 7.4 (10 mM phosphate with 150 mM NaCl) and 0.3 ml of each dilution of the serum-virus mixture was added to the corresponding well and incubated for 90 min at 37° C. in a 5% $CO_2$ incubator. Each assay was carried out in triplicates. The cells were overlaid with 2 ml of 0.85% methyl cellulose in MEM containing 10% fetal bovine serum, 1% penicillin-streptomycin and 1% L-glutamine. The plates were incubated at 37° C. in a 5% $CO_2$ incubator for 5 days. At the end of incubation, the plaques were fixed with 10% formalin, washed with 1×PBS, pH 7.4 and were visualized with 0.1% crystal violet. The highest dilution of serum causing 50% reduction in plaques formed by the control virus sample was estimated as the $PRNT_{50}$ titer. $PRNT_{50}$ assays were carried out to test the potency of the vaccine preparations by various inactivation methods, as well as for adjuvanted CHIKV vaccines and vaccine combination with JEV vaccine.

Example 8

Vaccine Combinations

A combination of CHIKV vaccine inactivated by beta-propiolactone was tested in combination with formalin inactivated vaccine for Japanese encephalitis virus (JEV). 15 µg of CHIKV vaccine antigen formulated in alum (0.5 mg aluminum/dose) was tested in combination with inactivated JE (JEV) virus vaccine containing 6 µg of Japanese encephalitis virus whole virion antigen also formulated in alum. The vaccine combination was injected in 8 nos of Balb/c mice with appropriate controls that included either of the antigens alone, and also control animals that received equivalent amount of alum. The animals were boosted at 7 and at 21 days after the first immunization. Blood was collected at 7 days after the last booster injection. Pooled sera from each group were complement inactivated at 56° C. for about 30 mM. The sera samples were used for estimation of neutralizing antibody by $PRNT_{50}$ for both CHIKV and JEV. The buffer used in all the formulations was 40 mM phosphate buffer, pH 6.8-7.2 containing 150 mM NaCl. All the methods disclosed above are applicable to any genotype/genotypic variants/serotypes and strains of Chikungunya virus.

REFERENCES

1. Kannan M, Rajendran R, Sunish I P, Balasubramaniam R, Arunachalam N, Paramsivan R, Tewari S C, Samuel P P, Tyagi B K. 2007. A study on Chikungunya outbreak during 2007 in Kerala, south India. Indian J Med Res 129:311-315
2. Sourisseau M, Schilte C, Casartelli N, Trouillet C, Guivel-Benhassine F, Rudnicka D, Sol-Foulon N, Le Roux K, Prevost M C, Fsihi H, Frenkiel M P, Blanchet F, Afonso P V, Ceccaldi P E, Ozden S, Gessain A, Schuffenecker I, Verhasselt B, Zamborlini A, Saïb A, Rey F A, Arenzana-Seisdedos F, Desprès P, Michault A, Albert M L, Schwartz O. 2007. Characterization of reemerging Chikungunya virus. PLoS Pathog 3:e89.
3. Powers A M, Brault A C, Tesh R B, Weaver S C. 2000. Re-emergence of Chikungunya and o'nyong-nyong viruses: evidence for distinct geographical lineages and distant evolutionary relationships. J Gen Virol 81:471-479.
4. Yergolkar P N, Tandale B V, Arankalle V A, Sathe P S, Sudeep A B, Gandhe S S, Gokhle M D, Jacob G P, Hundekar S L, Mishra A C. 2006. Chikungunya outbreaks caused by African genotype, India. Emerg Infect Dis 12:1580-1583.
5. Powers A M, Logue C H. 2007. Changing patterns of Chikungunya virus: re-emergence of a zoonotic arbovirus. J Gen Virol 88:2363-2377.
6. Arankalle V A, Shrivastava S, Cheman S, Gunjikar R S, Walimbe, A M, Jadhav, S M, Sudeep A B, Mishra A C. 2007. Genetic divergence of Chikungunya viruses in India (1963-2006) with special reference to the 2005-2006 explosive epidemic. J Gen Virol 88:1967-1976.
7. de Lamballerie X, Leroy E, Charrel R N, Tsetsarkin K, Higgs S, Gould E A. 2008. Chikungunya virus adapts to tiger mosquito via evolutionary convergence: a sign of things to come? Virol J 5:33.
8. Tong J C, Simarmata D, Lin R T, Rénia L, Ng L F. 2010. HLA Class I restriction as a possible driving force for Chikungunya evolution. PLoS One 5:e9291.
9. Volk S M, Chen R, Tsetsarkin K A, Adams A P, Garcia T I, Sall A A, Nasar F, Schuh A J, Holmes E C, Higgs S, Maharaj P D, Brault A C, Weaver S C. 2010. Genome-scale phylogenetic analyses of Chikungunya virus reveal independent emergences of recent epidemics and various evolutionary rates. J Virol 84:6497-6504.
10. Akahata W, Yang Z Y, Andersen H, Sun S, Holdaway H A, Kong W P, Lewis M G, Higgs S, Rossmann M G, Rao S, Nabel G J. 2010. A virus-like particle vaccine for epidemic Chikungunya virus protects nonhuman primates against infection. Nat. Med. 2010; 16(3):334-8.
11. Mallilankaraman K, Shedlock D J, Bao H, Kawalekar O U, Fagone P, Ramanathan A A, Ferraro B, Stabenow J, Vijayachari P, Sundaram S G, Muruganandam N, Sarangan G, Srikanth P, Khan A S, Lewis M G, Kim J J, Sardesai N Y, Muthumani K, Weiner D B. 2011: A DNA vaccine against Chikungunya virus is protective in mice and induces neutralizing antibodies in mice and nonhuman primates. PLoS Negl Trop Dis.; 5(1):e928.
12. Edelman R, Tacket C O, Wasserman S S, Bodison S A, Perry J G, Mangiafico J A. 2001: Phase II safety and immunogenicity study of live Chikungunya virus vaccine TSI-GSD-218. Am J Trop Med. Hyg. 2000; 62(6):681-5.

We claim:

1. A composition comprising inactivated Chikungunya virus strain wherein the Chikungunya virus strain has a non-synonymous mutation K1020E in the structural polyprotein corresponding to E1-K211E in the E1 structural glycoprotein either singly or in combination with other mutations selected from the group consisting of (i) K1020E of E1-211 protein in combination with, G380R of E2-55 protein, V589A of E2-264 protein in chikungunya virus strain TN01610; (ii) K1020E of E1-211 protein in combination with, D301N of E3-40 protein, V589A of E2-264 protein, G1004R of E1-195 protein in chikungunya virus strain TN151100; (iii) K1020E of E1-211 protein in combination with, K372N of E2-47 protein, V589A of E2-264 protein in chikungunya virus strain TN06210; (iv) K1020E of E1-211 protein in combination with, A232V of C-232 protein, V589A of E2-264 protein, G1004R of E1-195 protein in chikungunya virus strain TN06310; (v) K1020E of E1-211 protein in combination with, K391E of E2-66 protein, V589A of E2-264 protein in chikungunya virus strain TN06410; and (vi) K1020E of E1-211 protein in combination with, G380R of E2-55 protein, P867L of E1-58 protein, in chikungunya virus strain AP0109.

2. The composition of claim 1, wherein the inactivated Chikungunya virus strains contain nucleotide sequences disclosed in SEQ. ID. NO:1 to SEQ ID NO:7 and SEQ ID NO:15 to SEQ ID NO:20.

3. The composition of claim 1, wherein the composition further comprises an adjuvant selected from the group consisting of aluminum; hydroxide; aluminum phosphate; gamma inulin; algammulin; cholecalciferol in oil; an oil in water emulsion containing squalene, tween-80, and-Span-85 in 10 mM phosphate-citrate buffer; oil in water emulsion containing squalene, tween-80, Span-85, alpha tocopherol in phosphate-citrate buffer; an oil in water emulsion containing squalene, tween-80, Span-85 and cholecalciferol.

4. The composition of claim 1, wherein the inactivated Chikungunya virus strain has a non-synonymous mutation K1020E in the structural polyprotein corresponding to E1-K211E in the E1 structural glycoprotein in combination with other mutations selected from the group consisting of SEQ ID NO:1 to SEQ ID NO:7 and SEQ ID No:15 to SEQ ID No:20.

5. The composition of claim 1 further comprising an inactivated Japanese encephalitis antigen.

* * * * *